United States Patent
Darrah et al.

(10) Patent No.: US 12,429,473 B1
(45) Date of Patent: Sep. 30, 2025

(54) SYSTEMS AND METHODS FOR EVALUATING HYDROGEN GENERATION POTENTIAL FROM ROCKS IN NATURAL AND ENHANCED HYDROGEN PRODUCTION SYSTEMS USING GAS PROPERTIES

(71) Applicant: Koloma, Inc., Denver, CO (US)

(72) Inventors: Thomas Darrah, Westerville, OH (US); Colin Whyte, Grove City, OH (US); William Eymold, Columbus, OH (US); Christopher Gardner, Columbus, OH (US); Brent Lary, Columbus, OH (US)

(73) Assignee: Koloma, Inc., Denver, CO (US)

( * ) Notice: Subject to any disclaimer, the term of this patent is extended or adjusted under 35 U.S.C. 154(b) by 0 days.

(21) Appl. No.: 18/943,715

(22) Filed: Nov. 11, 2024

Related U.S. Application Data

(60) Provisional application No. 63/713,051, filed on Oct. 28, 2024.

(51) Int. Cl.
*G01N 33/24* (2006.01)

(52) U.S. Cl.
CPC .................. *G01N 33/24* (2013.01)

(58) Field of Classification Search
CPC ....................................................... G01N 33/24
See application file for complete search history.

(56) References Cited

U.S. PATENT DOCUMENTS

| | | | |
|---|---|---|---|
| 2021/0032987 A1* | 2/2021 | Seltzer | G01N 1/28 |
| 2021/0123344 A1* | 4/2021 | Westacott | G01N 33/0016 |
| 2022/0018737 A1* | 1/2022 | Thompson | G01N 1/2035 |
| 2023/0340850 A1* | 10/2023 | Montoya | E21B 25/08 |

FOREIGN PATENT DOCUMENTS

| | | | | |
|---|---|---|---|---|
| CN | 209559604 U | * | 10/2019 | |
| CN | 117451582 A | * | 1/2024 | G01N 13/00 |
| WO | WO-2015034463 A1 | * | 3/2015 | E21B 49/02 |

\* cited by examiner

*Primary Examiner* — Michael J Dalbo
*Assistant Examiner* — Kaleria Knox
(74) *Attorney, Agent, or Firm* — K&L Gates LLP

(57) ABSTRACT

Methods for identifying, evaluating, and high-grading rocks associated with past or future potential generation of hydrogen from geologic materials are provided. For example, a method for evaluating a hydrogen system within a geological source rock includes obtaining a geological sample of the geological source rock; extracting 'mobile' gases of the geological sample under a pressure gradient; evaluating the 'mobile' gases extracted from the geological sample; and quantifying a volume of hydrogen previously generated based on the 'mobile' gases.

20 Claims, 20 Drawing Sheets

| Mineral Classification Scheme | Description | Examples |
|---|---|---|
| $H_0$ | Primary minerals not directly involved in hydrogen generation | Quartz, Plagioclase, Calcite, Gypsum |
| $H_1$ | Primary (unaltered) minerals that potentially generate hydrogen | Olivine, Pyroxene |
| $H_2$ | Secondary (altered) minerals that generated hydrogen previously | Chlorite, Hematite, Magnetite |
| $H_{2a}$ $H_{2b}$ | Secondary (altered) minerals that can react to generate hydrogen again Secondary (altered) minerals that cannot generate hydrogen again | Magnetite Hematite, Lizardite |

Fig. 2

| Primary Mineral Assemblage (H₁) | Fe/Mg | Fe-rich Endmember |
|---|---|---|
| Augite | * | Pigeonite |
| Clinopyroxene | * | Hedenbergite |
| Orthopyroxene | * | Ferrosilite |
| Fe-Amphiboles | * | |
| Fe-Spinels | * | |
| Olivine | * | Fayalite |
| Ilmenite | | |

| Secondary Mineral Assemblage (H₂) | Fe/Mg | Fe²⁺/Fe³⁺ |
|---|---|---|
| Antigorite | * | |
| Celadonite | | * |
| Chrysotile | * | * |
| Clinochlore | * | * |
| Cordierite | * | * |
| Crostedtite | | |
| Epidote | * | * |
| Fe-Garnets | * | |
| Fe-Spinels | | |
| Glauconite | * | |
| Geothite | * | |
| Hematite | | |
| Kaolinite | * | * |
| Lizardite | * | * |
| Maghemite | | |
| Magnetite | * | * |
| Prehnite | * | * |
| Pumpellyite | | |
| Siderite | * | |
| Smectite/Nontronite | * | |
| Vermiculite | | |

Fig. 3

| Mineral | Mineral Phase | Serpentinization Reaction | Moles of Igneous Minerals | Moles of $H_2$ Generated | Moles of Magnetite Produced |
|---|---|---|---|---|---|
| Olivine | Fayalite | $3Fe_2SiO_4 + 2H_2O \rightarrow 2Fe_3O_4 + 3SiO_2 + 2H_2$ | 3 | 2 | 2 |
| Pyroxene | Ferrosilite | $3Fe_2Si_2O_6 + 2H_2O \rightarrow 2Fe_3O_4 + 6SiO_2 + 2H_2$ | 3 | 2 | 2 |

Fig. 5

| Source Rock Classification | Mineralogy | $H2_{EV}$ | $H2_{RPV}$ | Molar Predictions And Measurements | Comments |
|---|---|---|---|---|---|
| Non-source rock for hydrogen | Dominantly $H_0$ | Low | Low | $M_1, M_2 = 0$ | No evidence of past hydrogen generation or future hydrogen generating potential |
| Unconventional source rock-reservoir | Dominantly $H_{2a} + H_{2b}$ | High | Low | $H2_{EV} \sim M_2$ | Abundant hydrogen gas in samples, close to theoretical $M_2$ prediction |
| Accumulation in unconventional source rock-reservoir | $H_1$ or $H_{2a} + H_{2b}$ | High | Either | $H2_{EV} >> M_2$ | Abundant hydrogen gas in samples, greatly exceeds $M_2$ prediction |
| Source rock for conventional accumulations | Dominantly $H_{2a} + H_{2b}$ | Low | Low | $H2_{EV} << M_2$ | No hydrogen gas in samples despite abundant altered minerals |
| Unaltered source rock for EHP or mineralization | Dominantly $H_1$ | Low | High | $H2_{RPV} \sim M_1$ | No hydrogen gas in samples, abundant primary minerals generate hydrogen when exposed to ideal geologic conditions |

Fig. 7

SYSTEMS AND METHODS FOR EVALUATING HYDROGEN GENERATION POTENTIAL FROM ROCKS IN NATURAL AND ENHANCED HYDROGEN PRODUCTION SYSTEMS USING GAS PROPERTIES

CROSS-REFERENCE TO RELATED APPLICATIONS

This application claims benefit to U.S. Provisional Application No. 63/713,051, filed on Oct. 28, 2024, the entire disclosure of which is incorporated herein by reference.

FIELD OF THE INVENTION

Embodiments of the present disclosure relate generally to the fields of energy extraction, geology, geochemistry, mineralogy, geologic hydrogen exploration, geologic hydrogen extraction, or subsurface geologic hydrogen stimulation. The present disclosure relates to methods for extracting, measuring, quantifying, and evaluating the volumes and composition of chemical species contained within geologic material in order to assess the volume of hydrogen that was or can be generated from a given geologic material (e.g., hydrogen source rocks) for the purposes outlined above and below. More particularly, the present disclosure relates to methods for identifying, evaluating, and high-grading rocks associated with past or future potential generation of hydrogen from geologic materials.

BACKGROUND

This section is intended to introduce terminology and context associated with embodiments described in this disclosure. Thus, the following discussion in this section provides a framework for better understanding the disclosure, and is not to be viewed as an admission of prior art.

Hydrogen is a carbon-free energy carrier and chemical feedstock that can supplant carbon-based fossil fuels, especially when combined with other sources. Hydrogen can be generated using sustainable energy sources such as geothermal, solar, wind, and hydroelectric power. The disclosure herein relates to hydrogen produced from or generated within the Earth's subsurface and extracted by drilling, boring, mining, or various other means of penetrating the earth.

In the production of natural resources from formations within the earth, a well or borehole is drilled into the earth to the location where the natural resource is believed to be located. These natural resources may be hydrogen, helium, carbon dioxide, nitrogen, dihydrogen sulfide, methane, or other hydrocarbon gases; a dihydrogen sulfide reservoir, a hydrogen reservoir, a helium reservoir, a carbon dioxide reservoir, a natural gas reservoir, a reservoir rich in dihydrogen sulfide, a reservoir rich in hydrocarbons, a reservoir rich in hydrogen, a reservoir rich in helium; the natural resource may be fresh water, brackish water, or brine; it may be a heat source for geothermal energy; or it may be some other natural resource, ore deposit, mineral, metal, or gem that is located within the ground.

These resource-containing formations may be a few hundred feet, a few thousand feet, or tens of thousands of feet below the surface of the earth, including under the floor of a body of water (e.g., below the sea floor) or beneath other natural resources (e.g., below aquifers, lakes, mines). In addition to being at various depths within the earth, these formations may cover areas of differing sizes, shapes, and volumes.

Typically, and by way of general illustration, in drilling a well an initial borehole is made into the earth (e.g., the surface of land or seabed), and then subsequent and smaller diameter boreholes are drilled to extend the overall depth of the borehole. In this manner as the overall borehole gets deeper its diameter becomes smaller, resulting in what can be envisioned as a telescoping assembly of holes with the largest diameter hole being at the top of the borehole closest to the surface of the earth.

Thus, by way of example, the starting phases of a subsea drill process may be explained in general as follows. Once the drilling rig is positioned on the surface of the water over the area where drilling is to take place, an initial borehole is made by drilling a 36" hole in the earth to a depth of about 200-300 ft. below the seafloor. A 30" casing is inserted into this initial borehole. This 30" casing may also be called a conductor. The 30" conductor may or may not be cemented into place. During this drilling operation a riser is generally not used and the cuttings from the borehole (e.g., the earth and other material removed from the borehole by the drilling activity) are returned to the seafloor. Next, a 26" diameter borehole is drilled within the 30" casing, extending the depth of the borehole to about 1,000-1,500 ft. This drilling operation may also be conducted without using a riser. A 20" casing is then inserted into the 30" conductor and 26" borehole. This 20" casing is cemented into place. The 20" casing has a wellhead secured to it. (In other operations an additional smaller diameter borehole may be drilled, and a smaller diameter casing inserted into that borehole with the wellhead being secured to that smaller diameter casing.) A blow out preventer (BOP) is then secured to a riser and lowered by the riser to the sea floor, where the BOP is secured to the wellhead. From this point forward, all drilling activity in the borehole takes place through the riser and the BOP.

It should be noted that subsea drilling operations that do not employ a riser are also contemplated.

For a land-based drill process, the steps are similar, although the large diameter tubulars, 30"-20" are typically not used. Thus, and generally, there is a surface casing that is typically about 13⅜" diameter. This may extend from the surface, (e.g., wellhead and BOP) to depths of tens of feet to hundreds of feet. One of the purposes of the surface casing is to meet environmental requirements to protect groundwater by preventing surface casing ventflow to groundwater aquifers or prevent surface casing ventflow of greenhouse gases or flammable gases to groundwater aquifers or the atmosphere. The surface casing should have a sufficiently large diameter to allow the drill string, production equipment (e.g., electrical submersible pumps (ESPs)), and circulation mud to pass through. Below the casing, one or more different diameter intermediate casings may be used. (It is understood that sections of a borehole may not be cased and are referred to as open hole.) These can have diameters in the range of about 9" to about 7", although larger and smaller sizes may be used, and can extend to depths of thousands and tens of thousands of feet.

The section of the well located within the reservoir (i.e., the section of the formation containing the natural resources being targeted) can be called the pay zone. The production tubing is placed inside the casing and extends from a pay zone, or production zone of the borehole, up to and through the wellhead on the surface. There may be a single production tubing or multiple production tubings in a single borehole, with each of the production tubing endings being at different depths.

Fluid communication between the formation and the well or borehole can be greatly increased by the use of perforations, hydraulic fracturing, or other stimulation techniques. The first uses of hydraulic fracturing date back to the late 1940s and early 1950s. In general, hydraulic fracturing treatments involve forcing fluids down the well or borehole and into the formation, where the fluids enter the formation and crack, e.g., by forcing the layers of rock to break apart or fracture. These fractures create channels or flow paths that may have cross sections of a few microns, to a few millimeters, to several millimeters in size, and potentially larger. The fractures may also extend out from the well in all directions for a few feet, several feet, and tens of feet or further. The fractures may be kept open by using a proppant (e.g., various sized sand or other mineral grains) that is forced down the well with the fracturing fluid in a single operation. It should be remembered that the longitudinal axis of the well or borehole in the reservoir may not be vertical: it may be on an angle (either sloping up or down) or it may be horizontal.

During the drilling of wells or boreholes, drilling fluids (i.e., water-based mud, oil-based mud, water, foam, aerated mud, air, synthetic fluids, or other fluids), herein referred to as "drilling fluid," is often pumped down the borehole through the drill string and out into the borehole at the drill bit, then back up to the surface between the exterior of the drill string and the borehole wall. In some drilling operations, air or aerated fluid is injected through the drill string in a similar manner and can return formation fluids, including gases, to the surface. In the case where drilling fluid is used, it can lubricate the borehole, drill bit, and drill string, and prevent thermal degradation of the drill bit, as well as provide a medium through which to eject drilled rock (e.g., cuttings), sediment material, or formation fluids (e.g., gases) up the borehole to the surface.

Within the rock or sediment being drilled, fluids stored in pore spaces or fractures in the subsurface at the point of contact with or around the drill bit, or in shallower intervals that now are in contact with the borehole, can enter and mix with the circulating drilling fluid and return to the surface. Subsurface fluids, including gas, that enter the drilling fluid can remain dissolved in the circulating drilling fluid, migrate buoyantly as bubbles through the column of drilling fluid, or if sufficiently pressurized can flow as pulses of gas up the well or borehole.

At the surface, fluids, including gas, and the drilled rock or sediment material may be separated from the drilling fluid. The drilled rock or sediment material may be dropped onto a vibrating screen (shaker) to separate the solid material from drilling fluid, which may or may not be recycled and pumped back down the borehole during ongoing drilling of the borehole. During this time, formation fluids, including gas, may be separated from the drilling fluid, often using an agitating device, commonly termed the agitator, and the formation fluids (i.e., including gas) may be sampled directly using various sample devices (e.g., stainless steel cylinders, Isotubes®, Isobags®, Isoflasks®, copper tubes, etc.), plumbed to a gas buster or flaring device, or plumbed using piping or tubing (e.g., polyethylene, copper, or steel) to gas meters and/or various chemical instruments that can measure the bulk concentrations of various gas species separated from the drilling fluid.

In some examples, the subsurface rock formation from which gases are extracted can include at least one of sedimentary rocks (e.g., sandstone, limestone, shales, graywacke, evaporites), metamorphic rocks (e.g., gneisses, marbles), igneous rocks (e.g., dunite, pyroxenite, basalt, gabbros, granites, or other igneous rocks), or formations containing overly thermally mature hydrocarbon fluids, hydrocarbon source rocks, coal, or graphite. Other examples can include iron-rich rock, mafic igneous rock, metamorphosed or hydrothermally altered mafic igneous rock, olivine- or pyroxene-bearing igneous, metamorphic, or sedimentary rock or sediment, metamorphosed or hydrothermally altered olivine- or pyroxene-bearing igneous, metamorphic, or sedimentary rock or sediment, serpentine mineral-bearing rock or sediment, partially or completely serpentinized rock, serpentinite, pyrite, iron-rich sandstone, other iron-rich sedimentary rock, or iron-rich sediments.

In some examples, the source of hydrogen can include any of the sources described above (e.g., mafic or ultramafic rock) that is drilled, drilled and stimulated (e.g., hydraulic fracturing or perforation), drilled and stimulated (e.g., hydraulic fracturing or perforation) with the accompanying introduction of heat, chemicals, or fluids (e.g., water, carbon dioxide, dihydrogen sulfide, or combinations thereof), or fluids encountered while interacting with various subsurface reservoirs or geothermal systems, mining operations, water well drilling, formation waters, or any fluids exsolved from processes related to their exploration, characterization, or extraction.

Examples of geologic materials that can be collected to evaluate the past and future source rock potential to generate hydrogen, hydrogen derivatives (e.g., ammonia, dihydrogen sulfide, water vapor, hydrogen cyanide, or others), helium, hydrocarbons (e.g., $C_1$-$C_6$+), or other gases (e.g., carbon dioxide, nitrogen) include rock or sediment recovered from the drilling of a well or borehole (e.g., drill cuttings, whole core), or rock or sediment in contact with a drilled well or borehole (e.g., rock that comprises the well or borehole walls, such as rotary sidewall core), and rock or sediment collected from the surface.

Further, identifying the presence of high quality and mature hydrocarbon source rocks (i.e., rocks that have generated substantial amounts of oil or gas) is a necessary component of defining and developing exploration models for petroleum systems. Rock-Eval® pyrolysis is a commonly used method for evaluating the presence and quality of hydrocarbon source rocks. The Rock-Eval® process involves measuring various rock and fluid properties, including three distinct measurements: S1 (existing hydrocarbons present in the sample), S2 (remaining hydrocarbon generating potential), and S3 (the proportion of "spent" carbon not related to hydrocarbon generating potential). Using Rock-Eval®, the hydrocarbon source rock potential of a sample can be estimated by comparing S1 and S2 proportions to determine past and future hydrocarbon generation potential of a given petroleum system or to develop conceptual geologic models of where to explore for hydrocarbons in other parts of a geologic province, other geologic provinces, or to confirm that samples were collected from within an active petroleum system. However, Rock-Eval® and other currently available technologies are incapable of measuring key parameters of the geologic hydrogen system, including quantifying the volumes of existing hydrogen or the volumes of hydrogen generated in the geologic past, or evaluating hydrogen source rock potential.

It is necessary to evaluate and quantify hydrogen source rock presence and quality in order to develop robust models for hydrogen systems and exploration strategies for geologic hydrogen.

BRIEF SUMMARY

Embodiments of the present disclosure relate generally to the fields of energy extraction, geology, geochemistry, mineralogy, geologic hydrogen extraction, or subsurface geologic hydrogen stimulation. The present disclosure describes analytical systems and methods designed to extract, measure, and quantify the volumes and composition of the gaseous species contained within geologic materials to provide minimum estimates of the volume of hydrogen that has been generated by alteration of a geological sample (e.g., hydrogen source rock) throughout its geologic evolution. The systems and methods disclosed herein relate to measuring the hydrogen contained in samples of hydrogen source rocks and comparing this volume to predicted volumes of generated hydrogen based on the hydrogen source rock mineralogy in order to improve the development of natural geologic hydrogen exploration models, the strategies for enhanced hydrogen production and stimulation efforts, and the understanding of the geologic hydrogen system.

The present embodiment relates to systems for extracting, measuring, quantifying, and evaluating the volumes and composition of chemical species contained within geologic material in order to assess the volume of hydrogen that was produced from a given geologic sample for the purposes outlined above and below. These measurements can be obtained through field and laboratory analyses of drilled material (e.g., cuttings, whole core, rotary sidewall core either collected during drilling or retrieved from various sample repositories) or rocks or sediments collected at the surface. The results of these analyses will be used to evaluate past volumes of hydrogen (and other gases) generation from a given potential hydrogen source rock, relative permeability of hydrogen within a given source rock, and maturity of these source rocks relative to their remaining potential to generate hydrogen. These data and evaluations are essential for the purposes of exploring for naturally occurring geologic hydrogen, identifying targets for incipient or further stimulation of natural hydrogen by various means of enhanced hydrogen production, and the development of geologic hydrogen exploration workflows and models at various scales.

An embodiment develops the systems for measuring fluid properties of geologic materials (e.g., gas abundance, molecular and isotopic composition of hydrogen and other gas components) in order to quantify the existing volumes of hydrogen (e.g., volume of hydrogen per unit mass of rock) that are present within a given sample. This volume is termed $H2_{EV}$ and is analogous to the S1 metric determined by Rock-Eval®. Another embodiment involves the comparison of estimates of $H2_{EV}$ from different samples in order to identify: 1) other areas of the same geologic province that have likely generated similar volumes of hydrogen; 2) regions of the hydrogen system within the same geologic province that have likely generated the most significant volumes of hydrogen (i.e., "sweet spots"); 3) specific lithologic intervals within a given hydrogen system that have likely generated significant volumes of hydrogen; and/or 4) regions of geologic provinces that have generated less or no relevant quantities of hydrogen.

One embodiment utilizes the systems and methods for quantifying the $H2_{EV}$ in comparison to a predicted value based on evaluation of the mineral properties of a geologic sample. These properties include measuring the current mineral composition, estimating the original mineral content using modal or normative mineral models, and/or quantifying the proportion of altered minerals that would likely generate geologic hydrogen during their formation.

Another embodiment involves developing a quantitative algorithm that estimates the volume of hydrogen gas that has remained within hydrogen source rocks (i.e., either immobilized within or accumulated within prospective source rocks/unconventional source-reservoir pairs) and differentiates that from the volume of hydrogen that has migrated out of source rocks (i.e., by primary migration) and that can potentially migrate into and accumulate within other reservoirs and traps (i.e., by secondary hydrogen migration), or hydrogen that has been lost by other means. Example processes of other means that may remove hydrogen include chemical alteration (e.g., abiogenic methane formation, biogenic methane formation, dihydrogen sulfide formation, ammonia formation), abiogenic oxidation of hydrogen, or biodegradation of hydrogen (e.g., microbial oxidation)); the occurrence of these processes can be evaluated by other workflows and methods disclosed elsewhere. Importantly, the former quantifies the potential for "unconventional" hydrogen exploration that focuses on source-reservoir systems (e.g., analogous to "unconventional" hydrocarbon exploration), while the latter provides a critical metric that identifies targets for conventional hydrogen exploration.

Another embodiment involves determining the remaining potential volumes of hydrogen (e.g., volume of hydrogen per unit mass of rock) that can be generated from a geological sample under various idealized geologic conditions (e.g., temperature, pressure, fluid chemistry). The remaining potential volumes of hydrogen is termed $H2_{RPV}$ and is analogous to the S2 metric determined by Rock-Eval®.

Another embodiment utilizes results from these geochemical measurements to calibrate the chemistry (e.g., pH, oxygen fugacity, dissolved solutes) of the fluid placed in a reaction chamber that can then be used to optimize hydrogen generation from a specific potential hydrogen source rock under ideal geologic conditions (e.g., temperature, pressure). An alternative approach applies the same systems and methods described herein to evaluate the optimal pore fluid chemistry for hydrogen generation from various target lithologic formations.

Systems and methods to measure hydrogen involve placing samples of interest within a reaction chamber filled with known volumes of water with chemical properties that control for pH, oxygen fugacity, and dissolved solute composition that is then exposed to pressure and temperature conditions representative of the range of conditions in the geological province from which the samples were extracted and the pressure and temperature ranges relevant to hydrogen generation. For example, these sample-filled chambers may be exposed to various pressures (e.g., 15 to 15,000 psi) and heated to various temperatures (e.g., 20 to 500° C.), for various durations (e.g., 1 hour to 30+ days) in order to evaluate $H2_{RPV}$ in a given geologic sample.

Yet another embodiment involves developing a quantitative algorithm that estimates the $H2_{RPV}$ (using any of the approaches described herein) in order to: 1) determine the volumes of hydrogen that can be generated in other areas of the hydrogen system in the same geologic province where conditions are more favorable to hydrogen generation (e.g., at a different depth profile, in areas with different geothermal gradients, or in areas with different degrees of interaction between water and rock), 2) identify regions of the same geologic province with greater or less potential for hydrogen generation, and 3) identify regions of the hydrogen system in the same geologic province that are suitable for engineered/stimulated methods of enhanced hydrogen production or either carbon or sulfur mineralization, disclosed elsewhere.

These measurements can be obtained through field laboratory or traditional laboratory analyses of drilled material (e.g., cuttings, whole core, rotary sidewall core either collected during drilling or retrieved from various sample repositories) or rocks or sediments collected at the surface. The results of these analyses will be used to estimate the volumes of future generation of hydrogen from a given source rock and evaluate source rock potential of these materials regarding the generation of hydrogen for the purposes of exploration for geologic hydrogen, development of geologic hydrogen exploration models, the identification of targets for stimulated or enhanced hydrogen production (e.g., EHP, SEHP, SCHMEHP) disclosed elsewhere.

In another embodiment, the relative proportions of $H2_{EV}$ and $H2_{RPV}$ (i.e., the proportion of already generated hydrogen compared to its remaining potential) can be used to quantify the "maturity" of hydrogen generation in each hydrogen source rock sample and develop quantitative models of hydrogen generation to support natural hydrogen exploration strategies or engineered hydrogen production strategies as they pertain to the current geologic hydrogen system in a given geologic province. The systems and methods disclosed herein relate to the processes for identifying, evaluating, and high-grading source rocks by extracting, measuring, and quantifying the volumes of hydrogen generated via chemical reactions between geological samples and any combination of the following reactants: various gases or water with various chemistries and/or mixed with various chemicals. These chemical reactions may take place at various temperatures, for various durations, and/or at various pressures to optimize hydrogen generation or to assess the hydrogen generation potential of a source rock at higher pressures and temperatures given a fixed in situ chemistry. Results can be used to calibrate, integrate, and improve the development of geophysical or geochemical models and subsurface interpretations.

The systems and methods disclosed herein relate to the use of pressure and gas geochemical measurements to predict past or future generation of hydrogen from a rock on a molar or volumetric basis.

The systems and methods disclosed herein relate to systems and methods for evaluating the presence, quality (i.e., ability to generate hydrogen), and maturity (i.e., degree to which a sample has generated hydrogen) of a geological sample with respect to its suitability as a hydrogen source rock by detecting evidence of past hydrogen generation or accumulation, identifying targets for future hydrogen generation or various carbon or sulfur mineralization via injection/stimulation techniques disclosed elsewhere, or a combination of both.

The systems and methods disclosed herein relate to developing the processes and workflows to improve the identification of hydrogen source rocks and to determine where the same hydrogen source rock of various qualities may exist elsewhere within the same geologic province or other geologic provinces. This may involve the identification of rocks that are more suitable for hydrogen generation for natural hydrogen exploration (e.g., better temperature, pressure, water chemistry conditions, and/or lower preservation risks) or more appropriate for various forms of engineered hydrogen generation or carbon or sulfur mineralization based on measured mineralogy.

The systems and methods disclosed herein are built-for-purpose to be field portable devices designed to enable near-real time evaluation of a geologic sample obtained while actively drilling a well or borehole or conducting field sample collection of rocks or sediment at the surface.

Embodiments include the system and methods for identifying key rock formations where hydrogen has been generated or where hydrogen can be generated via engineered hydrogen production processes within a body of prospective source rock.

Currently available systems and methods are designed for petroleum systems and have limited capacity to accurately measure or quantify key chemical analytes related to hydrogen exploration. Specifically, currently available systems and methods are not able to robustly detect and/or quantify hydrogen, key hydrogen derivatives such as ammonia, water (or water vapor), hydrogen cyanide, or others. Further, analytical systems capable of measuring hydrogen, ammonia, water, and other hydrogen derivates can produce inaccurate results for molecules such as nitrogen, carbon dioxide, and other hydrocarbons based on the degree of analytical precision and accuracy that can be achieved in real time in the laboratory setting. Moreover, in some instances, the currently disclosed analytical methods do not utilize suitable sample extraction or preparation systems or methods capable of detecting and measuring these compounds within the analytical precision and accuracy tolerance of commercial chemical instruments.

In one example embodiment, a method is provided for enhanced measurement and quantification of the volumes and composition of gas species contained within geologic material. The method involves: 1) preparing a geological sample, 2) extracting the gas from the geological sample, 3) using a single gas stream or multiple gas streams from the fluid produced during gas extraction and separating gas species using one or multiple separation components to produce one or more processed gas streams, and 4) detecting the presence, pressure, and composition of gas species in the one or more processed gas streams by one or more mass spectrometers (FIG. 1).

In another embodiment of the present invention, a method for quantifying the future generation potential of geologic hydrogen from a geological sample involves: 1) analyzing a geological sample, 2) introducing a sample of the same raw geologic material into a reactor, 3) adding reactants to the same reactor to create a mixture of raw geologic material and reactants, 4) exposing the reactor to a single temperature, multiple temperatures, or incremental temperature changes over a period of time, 5) separating reacted solid materials from fluids, 6) analyzing reacted solids and the reacted gases and liquids from the reacted fluids, 7) comparing results of analyses of raw geologic material to results of analyses of reacted solids, liquids, or gases, 8) computing future hydrogen generation potential, and 9) appraising hydrogen source rock quality for either natural hydrogen exploration or enhanced hydrogen production targets.

In some embodiments, a method for quantifying hydrogen potential of a geological source rock includes: obtaining a geological sample of the geological source rock; placing the geological sample in a vessel and connecting the vessel to a vacuum chamber; applying a differential pressure to facilitate movement of 'mobile' gases out of the geological sample; removing one or more condensable gases from the 'mobile' gases through one or more cryogenic separation devices; evaluating one or more analyte gases using a mass spectrometer; quantifying a volume of hydrogen available for generation ($H2_{EV}$) based on the one or more analyte gases of the 'mobile' gases; determining a mineralogy of the geological sample; determining optimal conditions to induce mineral alteration to yield further potential hydrogen generation; quantifying a potential volume of generated hydrogen ($H2_{RPV}$) based on the mineralogy; and determining a source rock maturity ($H2_{maturity}$) accordingly:

In some aspects, the method further includes determining a mineralogy of the geological sample, wherein the mineralogy includes one or more of the following: primary minerals $H_1$ involved in hydrogen generation; secondary minerals $H_2$ that previously generated hydrogen, wherein the secondary minerals $H_2$ include a subset $H_{2a}$ of minerals capable of generating hydrogen and a subset $H_{2b}$ of minerals incapable of generating hydrogen; and one or more minerals $H_0$ unrelated to hydrogen generation.

In some aspects, quantifying the volume of hydrogen available for generation includes calculating the volume of hydrogen according to an equation wherein $M_1$ is calculated each mineral in a set of minerals i–P: where $m_{rock}$ is the mass of sample being analyzed, $\mu_i$ is the relative abundance of mineral i in the sample, $MW_i$ is the molecular weight of mineral i in kg/mol, and $\sigma_i$ is the stoichiometric ratio of moles of hydrogen generated from moles of mineral i, and wherein the equation $M_1$ is calculated for each mineral of the geological sample.

In some aspects, quantifying a volume of past hydrogen generation includes calculating the volume of hydrogen according to an equation wherein $M_2$ is calculated for each mineral in a set of minerals i–C: wherein $m_{rock}$ is the mass of sample being analyzed, $\mu i$ is the relative abundance of mineral i in the sample, $X_i$ is an iron concentration of each mineral i, $Z_i$ is the ratio of $Fe^{3+}/Fe_{total}$ of iron in mineral i, $MW_i$ is the molecular weight of mineral i in kg/mol, and $\sigma_i$ is the stoichiometric ratio of moles of hydrogen generated from moles of mineral i, and wherein the equation $M_2$ is calculated for each $H_{2a}$ and $H_{2b}$ mineral of the geological sample.

In some aspects, the method includes determining whether a geological source is a hydrogen rock source based on the $H2_{EV}$, the $H2_{RPV}$, the $M_1$, and the $M_2$. In some aspects, the method further includes measuring a rate of hydrogen release and calculating a relative permeability of hydrogen in the geological sample based on the rate of hydrogen release.

In some aspects, the quantifying step includes calculating a relative permeability of one or more permeating fluids in the geological source rock based on the relative permeability of the permeating fluids. In some aspects, the permeating fluids include one of hydrogen, helium, nitrogen, ammonia, water, methane, argon, hydrogen sulfide, krypton, xenon, oxygen, carbon dioxide, carbon monoxide, ethane, ethene, propane, butane, pentane, hexane, or hydrogen cyanide. In some aspects, quantifying includes calculating a relative permeability of the one or more permeating fluids in the geological source rock based on the rate of permeating fluid release.

In some aspects, a method of classifying geological source rock includes: determining a mineralogy of a geological sample of the geological source rock; quantifying a volume of hydrogen previously generated ($H2_{EV}$); quantifying a potential volume of hydrogen that may be generated ($H2_{RPV}$); quantifying a volume of hydrogen available for generation includes calculating the volume of hydrogen according to an equation wherein $M_1$ is calculated each mineral in a set of minerals i–P: where $m_{rock}$ is the mass of sample being analyzed, $\mu_i$ is the relative abundance of mineral i in the sample, $MW_i$ is the molecular weight of mineral i in kg/mol, and $\sigma_i$ is the stoichiometric ratio of moles of hydrogen generated from moles of mineral i, and wherein the equation $M_1$ is calculated for each mineral of the geological sample; quantifying a volume of past hydrogen generation includes calculating the volume of hydrogen according to an equation wherein $M_2$ is calculated for each mineral in a set of minerals i–C: wherein $m_{rock}$ is the mass of sample being analyzed, $\mu_i$ is the relative abundance of mineral i in the sample, $X_i$ is an iron concentration of each mineral i, $Z_i$ is the ratio of $Fe^{3+}/Fe_{total}$ of iron in mineral i, $MW_i$ is the molecular weight of mineral i in kg/mol, and $\sigma_i$ is the stoichiometric ratio of moles of hydrogen generated from moles of mineral i, and wherein the equation $M_2$ is calculated for each $H_{2a}$ and $H_{2b}$ mineral of the geological sample; classifying the geological source rock based on the volume of hydrogen previously generated ($H2_{EV}$), the potential volume of hydrogen that may be generated ($H2_{RPV}$), volume of hydrogen available for generation ($M_1$), and volume of past hydrogen generation ($M_2$).

In some aspects, a method of classifying geological source rock includes: obtaining a geological sample of the geological source rock; placing the geological sample in a vessel and connecting the vessel to a vacuum chamber; applying a differential pressure to facilitate movement of 'mobile' gases out of the geological sample; evaluating one or more analyte gases of the 'mobile' gases using a mass spectrometer; quantifying a volume of hydrogen previously generated ($H2_{EV}$) based on the one or more analyte gases of the 'mobile' gases; determining a mineralogy of the geological sample of the geological source rock, wherein the mineralogy includes one or more of the following: primary minerals $H_1$ involved in hydrogen generation; and secondary minerals $H_2$ that previously generated hydrogen, wherein the secondary minerals $H_2$ include a subset $H_{2a}$ of minerals capable of generating further hydrogen and a subset $H_{2b}$ of minerals incapable of generating hydrogen; quantifying a volume of past hydrogen generation includes calculating the volume of hydrogen according to an equation $M_2$ described herein, where $M_2$ is calculated for each mineral in a set of minerals i–C: wherein $m_{rock}$ is the mass of sample being analyzed, $\mu_i$ is the relative abundance of mineral i in the sample, $X_i$ is an iron concentration of each mineral i, $Z_i$ is the ratio of $Fe^{3+}/Fe_{total}$ of iron in mineral i, $MW_i$ is the molecular weight of mineral i in kg/mol, and $\sigma_i$ is the stoichiometric ratio of moles of hydrogen generated from moles of mineral i, and wherein the equation $M_2$ is calculated for each $H_{2a}$ and $H_{2b}$ mineral of the geological sample; classifying the geological source rock based on the volume of hydrogen previously generated ($H2_{EV}$) and volume of past hydrogen generation ($M_2$).

In further aspects, the method further includes adding a stimulant or a pore fluid composition to the geological sample; subjecting the geological sample to a range of temperatures or a range of pressures during a stimulation process; quantifying a volume of hydrogen produced by the stimulation process; quantifying a potential volume of hydrogen that may be generated ($H2_{RPV}$) based on the volume of hydrogen produced by the stimulation process; quantifying a volume of hydrogen available for generation comprises calculating the volume of hydrogen according to an equation $M_1$ described below, where $M_1$ is calculated each mineral in a set of minerals i–P, where $m_{rock}$ is the mass of sample being analyzed, $\mu_i$ is the relative abundance of mineral i in the sample, $MW_i$ is the molecular weight of mineral i in kg/mol, and $\sigma_i$ is the stoichiometric ratio of moles of hydrogen generated from moles of mineral i, and wherein the equation $M_1$ is calculated for each $H_1$ and $H_{2a}$ minerals of the geological sample; and classifying the geological source rock based on the volume of hydrogen previously generated ($H2_{EV}$), the potential volume of hydrogen that may be generated ($H2_{RPV}$), volume of hydrogen available for generation ($M_1$), and volume of past hydrogen generation ($M_2$).

In some aspects, classifying the geological rock source includes classifying the geological rock source as a non-source rock for hydrogen when the $M_1$ and $M_2$ are zero. In some aspects, determining the mineralogy includes determining if the geological sample includes an abundant volume of hydrogen previously generated ($H2_{EV}$) with limited potential volume of hydrogen that may be generated ($H2_{RPV}$). In some aspects, classifying the geological source rock includes classifying the geological source rock as hydrogen accumulation within the geological source rock when the volume of hydrogen previously generated ($H2_{EV}$) is greater than the volume of past hydrogen generation ($M_2$). In some aspects, classifying the geological source rock includes classifying the geological source rock as an unconventional source rock-reservoir within the geological source rock when the volume of hydrogen previously generated ($H2_{EV}$) is about equivalent to the volume of past hydrogen generation ($M_2$). In some aspects, the volume of hydrogen previously generated ($H2_{EV}$) is less than the volume of past hydrogen generation ($M_2$). In some aspects, the techniques described herein relate to a method, wherein classifying the geological rock source includes classifying the geological rock source as a source rock for conventional accumulations. In some aspects, the method further includes determining if the geological sample includes abundant altered minerals and no hydrogen gas.

In some aspects, a determination of abundant altered minerals and no hydrogen gas indicates that hydrogen gas has migrated to other lithologic formations or has been consumed through subsurface chemical or biological processes. In some aspects, classifying the geological rock source includes classifying the geological rock source as a source rock for a conventional hydrogen system with prospective accumulation in porous reservoirs.

In some aspects, the techniques described herein relate to a method, further including evaluating the mineralogy. In some aspects, evaluating the mineralogy includes determining whether the geological sample includes abundant primary minerals and no hydrogen gas. In some aspects, classifying the geological rock source includes classifying the geological rock source as an unaltered source rock suitable for enhanced hydrogen production (EHP), carbon mineralization, or sulfur mineralization.

In some aspects, the mineralogy includes one or more of the following: primary minerals $H_1$ involved in hydrogen generation; secondary minerals $H_2$ that previously generated hydrogen, wherein the secondary minerals $H_2$ include a subset $H_2a$ of minerals capable of generating further hydrogen and a subset $H_{2b}$ of minerals incapable of generating hydrogen; and one or more minerals $H_0$ unrelated to hydrogen generation. In some aspects, the geological source rock is classified as a non-source rock for hydrogen when the mineralogy is dominantly $H_0$, the $H2_{EV}$ is low, and the $H2_{RPV}$ is low. In some aspects, the geological source rock is classified as an unconventional source rock-reservoir when the mineralogy is predominantly $H_{2a}$ and $H_{2b}$, the $H2_{EV}$ is high, and the $H2_{RPV}$ is low. In some aspects, the geological source rock is classified as an accumulation in unconventional source rock-reservoir when the mineralogy is dominantly $H_1$ or dominantly $H_{2a}$ and $H_{2b}$ and the $H2_{EV}$ is high. In some aspects, the geological source rock is classified as a source rock for conventional accumulation when the mineralogy is dominantly $H_{2a}$ and $H_{2b}$, the $H2_{EV}$ is low, and the $H2_{RPV}$ is low. In some aspects, the geological source rock is classified as an unaltered source rock for EHP or mineralization when the mineralogy is dominantly $H_1$, the $H2_{EV}$ is low, and the $H2_{RPV}$ is high.

Features from any of the disclosed embodiments may be used in combination with one another, without limitation. In addition, other features and advantages of the present disclosure will become apparent to those of ordinary skill in the art through consideration of the following detailed description and the accompanying drawings.

The foregoing brief summary is provided merely for the purpose of summarizing some example embodiments described herein. Because the above-described embodiments are merely examples, they should not be construed to narrow the scope of this disclosure in any way. It will be appreciated that the scope of the present disclosure encompasses many potential embodiments in addition to those summarized above, some of which will be described in further detail below.

In further embodiments, any of the features, functionality and alternatives described in connection with any one or more of FIGS. 1 to 19 may be combined with any of the features, functionality, and alternatives described in connection with any other of FIGS. 1 to 19.

BRIEF DESCRIPTION OF THE FIGURES

The drawings illustrate several embodiments of the disclosure, wherein identical reference numerals refer to identical or similar elements or features in different views or embodiments shown in the drawings.

FIG. 2 is a table describing the primary ($H_1$), and secondary ($H_2$) hydrogen generating mineral assemblages. Minerals that are unrelated to hydrogen generation are referred to as $H_0$, and example minerals are provided for each category.

FIG. 3 is a table providing the names for the mineral assemblages associated with $H_1$, $H_{2a}$, and $H_{2b}$. Asterisks in the Fe/Mg and $Fe^{2+}/Fe^{3+}$ columns indicate that elemental and oxidation states need to be considered in stoichiometric predictions for those minerals.

FIG. 5 is a table of stoichiometrically balanced hydrogen generation reactions featuring fayalite and ferrosilite.

FIG. 7 is a table containing the ideal characteristics of various types of hydrogen source rocks (non-hydrogen source rock, unconventional source-reservoir pairs, hydrogen accumulation in an unconventional source rock-reservoir, source rock for conventional accumulations, or unaltered source rock for EHP or carbon/sulfur mineralization). The table contains the relative proportions of multiple parameters including the mineral assemblages ($H_0$, $H_1$, $H_2$, $H_{2a}$, $H_{2b}$), normative and modal predictive modeling of future hydrogen generating potential ($M_1$) or past hydrogen generation ($M_2$), and gas measurements of existing volumes of hydrogen and remaining hydrogen generating potential of a given hydrogen source rock sample. The unaltered source rock may be relevant to exploration for targets for various engineered stimulation processes to generate hydrogen or mineralize carbon or sulfur disclosed, or for identifying high-quality source rocks that did not generate hydrogen in one part of a geologic province but may generate hydrogen in other parts of the same geologic province if more favorable conditions exist in those areas.

FIG. 9A displays the sealed sample vessel prepared for gas extraction, and FIG. 9B shows the gas extraction process, where a needle attached to a static vacuum line pierces a pierceable seal or a valve is opened, allowing for the atmospheric gas and gas derived from the geologic material to expand into the vacuum line. This expansion increases the pressure gradient between the hydrogen source rock and the vacuum line, enhancing the release of gas from the hydrogen source rock. Single, multiple, sequential, and/or prolonged extractions may be completed to increase the pressure gradient between the hydrogen source rock and the vacuum line, further degassing the sample.

FIG. 13A displays a sealed sample vessel prepared for gas extraction and FIG. 13B shows the gas extraction process, where the portion of copper tube containing the geologic material is compressed with a hydraulic press, crushing the sample. The disintegration of the geologic sample creates new pathways for previously isolated 'immobile' gases (i.e., gases contained within the pore space and/or fluid inclusions) to be released, thus enhancing the rate of gas extraction.

DETAILED DESCRIPTION

Figure 1:
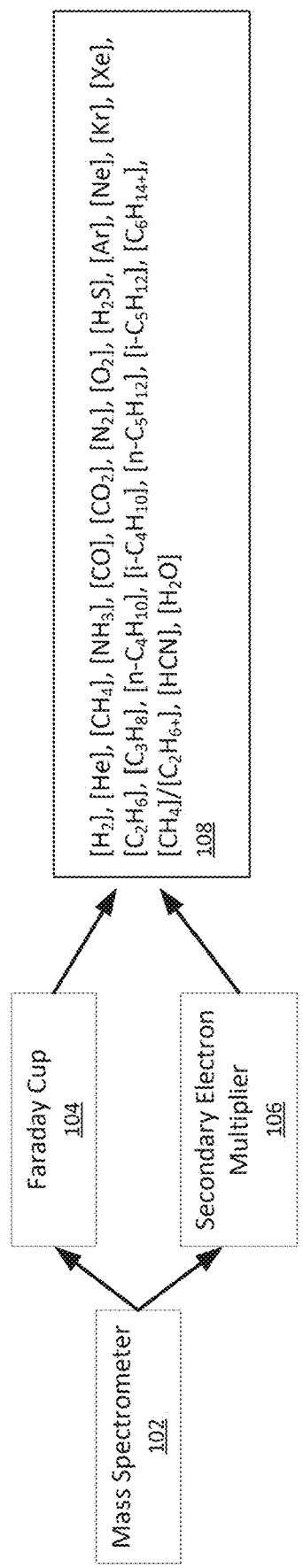
FIG. 1 is a block diagram of a system including one or more of a mass spectrometer 102, a faraday cup 104, a secondary electron multiplier 106 for measuring a series of components 108 that may include hydrogen ($H_2$), helium (He), ammonia ($NH_3$), hydrocarbon gases (e.g., $C_1$, $C_2$, $C_3$, $C_{4+}$), nitrogen ($N_2$), carbon dioxide ($CO_2$), various hydrogen-derived chemical species (e.g., dihydrogen sulfide ($H_2S$), hydrogen cyanide (HCN)), or other gases that: a) advect or diffuse into a gas-tight sample vessel based on pressure or concentration gradients from geologic material, b) are released from geologic material by crushing within a gas-tight sample vessel, or c) are generated within a reaction chamber containing the rock relevant to hydrogen generation and known volumes of water with chemical properties that control pH, oxygen fugacity, and dissolved solute composition that is exposed to pressure and temperature conditions representative of the range of conditions in the geological province from which they were extracted and relevant to conditions optimal for hydrogen generation. For example, these sample-filled chambers may be exposed to various pressures (e.g., 15 to 15,000 psi) and heated to various temperatures (e.g., 20 to 500° C.), for various durations (e.g., 1 hour to 30+ days) in order to evaluate the remaining potential volumes of hydrogen ($H2_{RPV}$) in a geologic sample.

Embodiments of the present disclosure relate generally to the fields of energy extraction, geology, geochemistry, mineralogy, geologic hydrogen exploration, geologic hydrogen extraction, or subsurface geologic hydrogen stimulation. The present embodiment discloses analytical systems that extract, measure, and quantify the volumes and composition of chemical species contained within geologic material in order to provide minimum estimates of past gas generation or accumulation within a given source rock. These measurements can be obtained through field and laboratory analyses of drilled material (e.g., cuttings, whole core, rotary sidewall core either collected during drilling or retrieved from various sample repositories) or rocks or sediments collected at the surface.

The results of these analyses will be used to evaluate past volumes of gas generation from a given source rock, relative permeability of hydrogen within a given source rock, and maturity of these source rocks relative to their remaining potential generation of hydrogen. These data and evaluations are essential for the purposes of exploring for geologic hydrogen and the development of geologic hydrogen exploration models.

An embodiment develops the systems for measuring fluid properties of geologic materials (e.g., gas abundance, molecular and isotopic composition of hydrogen and other gas components) in order to quantify the existing volumes of hydrogen (e.g., volume of hydrogen per unit mass of rock) that are present within a given sample. This volume is termed $H2_{EV}$ and is analogous to the S1 metric determined by Rock-Eval®. Another embodiment involves the comparison of estimates of $H2_{EV}$ from different samples in order to identify: 1) other areas of the same geologic province that have likely generated similar volumes of hydrogen, and 2) regions of the hydrogen system within the same geologic province that have likely generated the most significant volumes of hydrogen.

Other embodiments utilize the systems and methods described herein to evaluate the hydrogen potential under ideal geologic conditions (e.g., temperature, pressure, fluid chemistry). In other embodiments, measurements of potential hydrogen generation are made by placing samples of geologic material and known volumes of water with chemical properties that control for pH, oxygen fugacity, and dissolved solute composition into a reaction chamber and exposing it to pressure and temperature conditions representative of the range of conditions in the geological province from which the samples were extracted and the conditions optimal for hydrogen generation. For example, sample-filled chambers may be exposed to various pressures (e.g., 15 to 15,000 psi) and heated to various temperatures (e.g., 20 to 500° C.), for various durations (e.g., 1 hour to 30+ days) in order to evaluate the remaining potential volume of hydrogen (e.g., volume of hydrogen per unit mass of rock) that can be generated from a geological sample. This volume is termed $H2_{RPV}$ and is analogous to the S2 metric determined by Rock-Eval®. Algorithms are developed that evaluate results from these measurements to quantitatively assess the hydrogen generation potential of the source rock, place it in the context of the broader hydrogen system, and extrapolate results of these measurements to other locations within a geologic province that may generate hydrogen.

Although the present specification focuses on natural hydrogen exploration and target selection for stimulated hydrogen generation (i.e., termed herein enhanced hydrogen production (EHP)), it is understood that the techniques disclosed herein are not so limited and find application in the drilling for a variety of naturally occurring molecules, including hydrogen, dihydrogen sulfide, hydrogen derivatives, helium, other noble gases, hydrocarbons, nitrogen, and carbon dioxide. It is also understood that these techniques may include the stimulation and/or in situ generation or release of hydrogen or other hydrogen derivatives (e.g., EHP), or engineered processes of carbon or sulfur mineralization. Other examples may include processes related to the production, purification, or handling of those fluids, drilling for the recovery of other natural subsurface resources (e.g., geothermal heat, minerals/ores, groundwater), and the production, purification, or handling of those resources, drilling for the purpose of subsurface sequestration of fluids (e.g., carbon dioxide, dihydrogen sulfide), gas storage (e.g., hydrocarbons, hydrogen, or helium), brine or waste water disposal, enhanced geothermal, and other types of drilling into the subsurface where fluids may be detected, monitored, or quantified.

Overview and Limitations of Petroleum

Source Rock Analysis to Evaluate Hydrogen Systems

In the typical oil and gas exploration workflow, source rocks are evaluated to determine maturity, or the proportion of source rock that has already generated hydrocarbons. Methods that do this can include determining the vitrinite reflectance ($R_o$), the conodont alteration index (CAI), or using Rock-Eval® pyrolysis. In recent decades, the latter has become a standard practice for source rock evaluation. The Rock-Eval® process involves measuring various rock and fluid properties, including three distinct measurements: S1 (existing hydrocarbons present in the sample), S2 (remaining hydrocarbon generating potential in the sample), and S3 (the proportion of "spent" carbon not related to hydrocarbon generating potential in the sample). Using Rock-Eval®, the source rock potential of a sample of a petroleum system can be estimated by comparing S1 and S2 proportions to determine past and future hydrocarbon generation potential or to develop conceptual geologic models of where to explore for hydrocarbons in other parts of the geologic province, other geologic provinces, or to confirm that samples were collected from within an active hydrocarbon system.

The Rock-Eval® process developed for petroleum systems does not conceive of or consider key aspects of the natural hydrogen generation process, including methods, systems, or data acquisition and processing requirements to properly investigate the generation of hydrogen over geologic time or the potential for future hydrogen generation. The background, methods, and embodiments disclosed below document a series of novel methods to evaluate source rock quality for natural hydrogen systems and develop the capability to categorize, rank, and high-grade natural hydrogen source rocks for a variety of exploration approaches.

Systems and Methods to Evaluate the Fate of Generated Hydrogen

The systems and methods for quantifying hydrogen generation processes provide important constraints relevant to developing models and strategies for geologic hydrogen exploration. However, these methods do not directly: 1) quantify the volumes of hydrogen currently present in source rocks (but instead only provide models of total hydrogen generation), 2) provide estimates of the proportion of hydrogen that has migrated out of source rocks which potentially could have accumulated in conventional reservoirs or been degraded by other processes, or 3) inform models regarding the volumes of potentially extractable hydrogen in various source rocks.

For example, mineralogical methods that evaluate source rock material are incapable of determining whether the hydrogen that has been generated remains within the source rock or migrates out of the source rock and potentially accumulates within non-source-rock reservoirs. Similarly, mineralogical methods do not constrain the presence, volume, or composition of hydrogen within sample materials (e.g., the proportion of hydrogen relative to other components (e.g., helium, nitrogen, methane, carbon dioxide, or others) or the isotopic composition of hydrogen or other gases present) or the key properties of those rocks, such as fluid pressure or relative permeability within targeted geologic hydrogen systems. Each of these factors is critical to validating the presence, quality, and relative ranking of the source rock component of natural hydrogen systems (i.e., confirming the presence of an active hydrogen source rock that is currently generating hydrogen or has generated significant volumes of hydrogen in the geologic past), the development of exploration strategies to exploit natural hydrogen resources in a given area (e.g., exploration for conventional, unconventional, or enhanced hydrogen production targets), informing hydrogen exploration workflows, such as geophysical, geological, and geochemical field collection programs, and informing operational and business decision making during and after drilling, testing, and completion.

Once the volume of hydrogen that has been generated within a given rock sample has been quantified, other critical factors that must be addressed as part of the hydrogen exploration workflow include estimating the timing of hydrogen generation (i.e., the critical moment of hydrogen generation), determining the proportion of hydrogen that has been preserved (or alternatively degraded), and assessing the relative timing and configuration of the emplacement of reservoirs, traps, and seals.

Direct measurement of fluids in source rocks allows for quantification of the volumes of hydrogen currently present in these rocks. The comparison between the estimated volume that has been generated and currently measured in the rock provides essential geologic exploration context to evaluate the role and quality of hydrogen source rocks. The explicit comparison of the volumes of hydrogen generated over time to the volumes of hydrogen directly measured in rock samples enables the development of quantitative models that apportion: 1) the volume of hydrogen that has been generated and remains within source rocks, and 2) the volume of hydrogen that has either migrated from source rocks that may accumulate in other conventional reservoirs or that has been lost by other means; this latter portion can be evaluated by other methods not disclosed herein. From the proportions of generated hydrogen that migrated out of source rocks, volumes may accumulate in conventional reservoirs, be lost through chemical or biological processes that degrade hydrogen, or have degassed at the surface. The fate of these volumes must be considered by other exploration workflows. However, the methods disclosed herein constitute an important component of evaluating and quantifying hydrogen generation and existing hydrogen volumes in source rock.

As an example, hydrogen observed in hydrogen source rocks may be reasonably assumed to have been contained in the formation since its generation when there is an absence of conduits of fluid entry/escape (i.e., migration pathways) or other methods of hydrogen loss (e.g., chemical reactivity, microbial degradation). As a result, the volumes of hydrogen generated can be used to reduce uncertainty surrounding the critical moment of hydrogen generation (i.e., the moment of hydrogen generation when adequate reservoir and sealing lithologies are present and in a 3D configuration capable of trapping and accumulating hydrogen) if the measured volumes of hydrogen are in balance with anticipated volumes based on hydrogen generation models that use the present pressure and temperature conditions and mineral observations. Alternatively, significantly lower measured volumes of hydrogen compared to modeled volumes of hydrogen generation could indicate other scenarios, such as the migration of hydrogen from source rocks into other components of conventional hydrogen systems or other risks such as hydrogen degradation.

After gas generation, the volume of hydrogen measured in hydrogen source rock samples may represent the hydrogen generated and subsequently trapped, analogous to unconventional hydrocarbon-rich shales or carbonates. In this scenario, measurement of the bulk hydrogen source rock (e.g., collected from drilled material) and the fluids trapped within them provides a method of direct quantification of the moles of hydrogen retained in source rocks.

If there is sufficient diffusion or advection of hydrogen out of source rocks, hydrogen may migrate into overlying formations and potentially into overlying conventional sedimentary reservoirs. Gas may migrate buoyantly upwards through water-saturated rock formations along migration pathways that may include interconnected pore space (i.e., effective porosity), or along fractures or faults until reaching a formation (or interval of a fracture or fault) that is of sufficiently low porosity and low permeability to prevent further migration (i.e., a seal). Generally, porous and permeable rock formations underneath low porosity and low permeability seals may serve as reservoirs where geologic hydrogen or other natural gases (e.g., helium, $CO_2$, $H_2S$, hydrocarbons) can accumulate.

The proportion of hydrogen that may have accumulated can be evaluated by other workflows. One example of how the systems and methods developed here can benefit those workflows is described below. The difference between total hydrogen potential calculated through an evaluation of mineralogy, elemental composition, and iron oxidation state, and the volume of hydrogen measured directly allows for quantification of: 1) the total volume of hydrogen generated, as calculated based on the mineral models and 2) the volume of hydrogen measured using the systems and methods disclosed herein. The quantification of hydrogen and other gases (e.g., helium, nitrogen, $CO_2$, $H_2S$, hydrocarbons) trapped within the pore spaces in hydrogen source rocks or sedimentary rocks within a conventional system may provide valuable information related to: 1) identifying intervals or lithologies that currently serve as hydrogen reservoirs and seals, 2) quantifying permeability of hydrogen relative to the other gases present in the intervals or formations based on the ease with which the gases escape the pore space, and 3) the intrinsic pressure of hydrogen in the reservoir intervals or formations.

Geologic Hydrogen Systems Analysis

The exploration for active hydrogen systems involves the identification and mapping of suitable quality geologic hydrogen source rocks that contain elevated proportions of minerals involved in the generation of hydrogen in both unaltered (primary) and altered (secondary) mineral phases. Notably, an important aspect of natural hydrogen exploration (analogous to petroleum exploration) involves determining the parts of geologic provinces that contain the highest quality source rocks (i.e., where the highest rates of hydrogen generation on a moles of hydrogen per mass or volume of rock basis have occurred).

Figure 4:
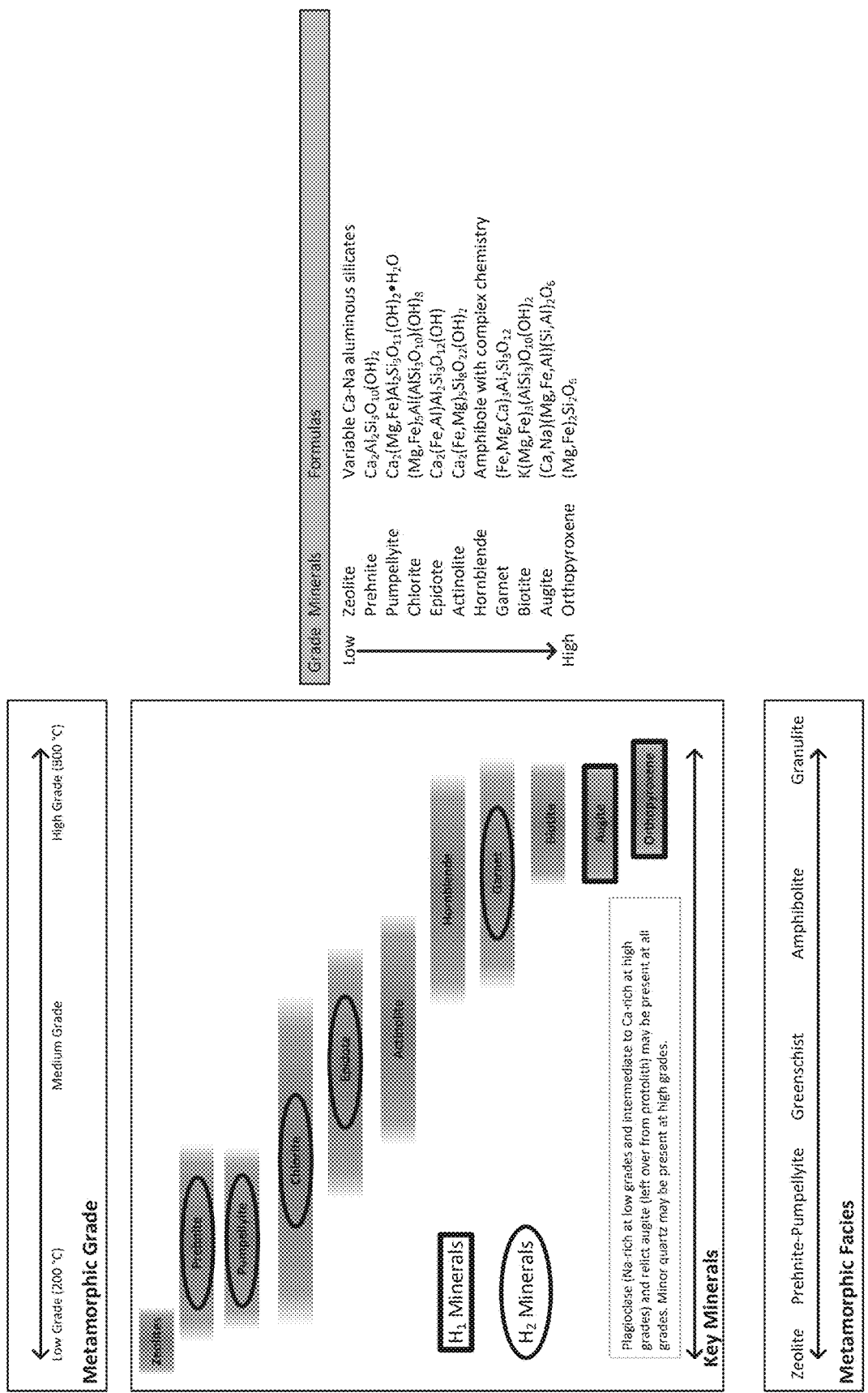
FIG. 4 is a diagram placing the altered minerals in the context of the pressure and temperature conditions associated with increasing metamorphic grade, with a table of chemical formulas for each mineral. $H_1$ minerals are outlined by a rectangle and $H_2$ minerals are outlined by an oval.

The primary mineral phases involved in hydrogen generation are termed $H_1$ minerals and include augite (pigeonite), clinopyroxene (hedenbergite), orthopyroxene (ferrosilite), Fe-amphiboles, Fe-spinels, olivine (fayalite), and ilmenite (see FIGS. 2 and 3). Similarly, the secondary mineral phases are termed $H_2$ minerals and include antigorite, celadonite, chrysotile, clinochlore, cordierite, cronstedtite, epidote, Fe-garnets, Fe-spinels, glauconite, goethite, hematite, kaolinite, lizardite, maghemite, magnetite, prehnite, pumpellyite, siderite, smectite/nontronite, or vermiculite (FIG. 4).

The $H_2$ mineral phases can be classified further into $H_{2a}$ if they generated hydrogen during their formation and can react again to generate more hydrogen (e.g., magnetite) or $H_{2b}$ if they generated hydrogen during formation but cannot generate more hydrogen through subsequent alteration (e.g., hematite). All other mineral phases that are not directly involved in the generation of hydrogen (e.g., quartz, calcite, plagioclase) as well as other alteration products that did not generate hydrogen during formation and cannot generate hydrogen by being altered further (e.g., biotite) are collectively referred to as $H_0$ minerals (FIG. 2).

Notably, an important aspect of geologic hydrogen exploration involves determining the parts of geologic provinces that contain the highest quality source rocks (i.e., rocks comprised of elevated amounts of $H_1$ and $H_2$ minerals associated with the highest volumes of past and/or future hydrogen generation on a moles of hydrogen per mass or volume of rock basis). Summation of the $H_1$ and $H_{2a}$ minerals enables an estimate of the moles of hydrogen that can be generated from further alteration of the rock (termed $M_1$) and likewise, summation of the moles of all $H_{2a}$ and $H_{2b}$ minerals enables an estimate of the moles of hydrogen that had been generated from past alteration of the rock (termed $M_2$).

Starting with the $M_1$ reactions, the simplest estimate of hydrogen generation uses the mineralogy of a sample to sum contributions from multiple stoichiometric equations that account for the moles of hydrogen generated from each mole of a given mineral:

$$M_1 = m_{rock} \cdot \sum_i^P \frac{\mu_i}{MW_i} \cdot \sigma_i$$

where $m_{rock}$ is the mass of sample being analyzed, $MW_i$ is the molecular weight of mineral i in kg/mol, and $\sigma_i$ is the stoichiometric ratio of moles of hydrogen generated from moles of mineral i. This equation is summed across all P minerals involved in the $M_1$ reactions, which for hydrogen source rock potential will include all $H_1$ and $H_{2a}$ minerals, to calculate the total moles that can potentially be generated for a given mass of rock if the rock is stimulated through natural or engineered processes.

This model can be improved through laboratory analysis (XRD, SEM/EDS) by accounting for the iron-rich phases of minerals (e.g., accurate proportions of fayalite vs. forsterite in olivine) to constrain the stoichiometry using iron concentration of each mineral i ($X_i$):

$$M_1 = m_{rock} \cdot \sum_i^P X_i \frac{\mu_i}{MW_i} \cdot \sigma_i$$

Furthermore, for phases which can contain both $Fe^{2+}$ and $Fe^{3+}$ iron in their mineral structure, Mössbauer mass spectrometry of secondary minerals (e.g., particularly in the case of clays and low temperature and pressure metamorphic facies) can measure the ratio of $Fe^{2+}/Fe_{total}$ of iron in mineral i ($Y_i$) which further constrains the molar output:

$$M_1 = m_{rock} \cdot \sum_i^P X_i \cdot Y_i \frac{\mu_i}{MW_i} \cdot \sigma_i$$

Finally, the kinetics of hydrogen generation reactions may preclude alteration of a mineral based on the rate of reaction for some minerals compared to others, rendering their reactions less relevant to engineered stimulation (e.g., EHP) that occurs on the minutes to weeks timescale. The kinetic rates of these reactions will strongly depend on geochemical and geophysical conditions (e.g., pressure, temperature, Eh, pH, salinity) of the system as well as the mineral itself (e.g., phase, reactive surface area, chemical composition). Through kinetic experiments, literature values, and/or computational simulations, kinetic factors ($k_i$) that describe how rapidly the alteration reaction proceeds can be determined for each mineral to make a comprehensive stoichiometric estimate of hydrogen generation:

$$M_1 = m_{rock} \cdot \sum_i^P k_i \cdot X_i \cdot Y_i \frac{\mu_i}{MW_i} \cdot \sigma_i$$

Similarly, the moles of hydrogen generated by completed reactions ($M_2$) can be calculated as:

$$M_2 = m_{rock} \cdot \sum_i^C X_i \cdot Z_i \frac{\mu_i}{MW_i} \cdot \sigma_i$$

where $m_{rock}$ is the mass of sample being analyzed, $X_i$ is the iron concentration of mineral i, $Z_i$ is the ratio of $Fe^{3+}/Fe_{total}$ of iron in mineral i, $MW_i$ is the molecular weight of mineral i in kg/mol, and $\sigma_i$ is the stoichiometric ratio of moles of hydrogen generated from moles of mineral i. This equation is summed across all C minerals involved in the $M_2$ reactions, which for hydrogen source rock potential will include all $H_{2a}$ and $H_{2b}$ minerals, to get the total moles generated for a given mass of rock from past alteration reactions. Note that kinetics are not considered in the $M_2$ calculation because the reactions have already completed.

The "optimal" characteristics of hydrogen source rock in a given geologic province depends upon the exploration strategy. "Conventional" exploration seeks to identify geologic hydrogen that formed in hydrogen source rocks and migrated to and accumulated within reservoir rocks contained by lithological seals with suitable trapping geometries. By comparison, "unconventional" exploration seeks to identify geologic hydrogen that formed and charged source-reservoir systems and is dominantly contained within the porosity of mature source rocks that was created through fracture generation or mineral alteration caused, for example, by the emplacement process.

Either of these exploration pathways requires the rigorous identification of mature source rocks that have generated significant volumes of hydrogen (e.g., rocks comprised of high concentrations of $H_2$ minerals). As detailed below, there are characteristics of optimal hydrogen systems from each strategy that can be differentiated by the systems, algorithms, and workflows disclosed herein. Alternatively, these systems, algorithms, and workflows may be used for the identification of exploration targets for enhanced hydrogen production (EHP) or carbon sequestration by carbon mineralization or sulfur sequestration by sulfur mineralization in prospective areas with high proportions of hydrogen source minerals without past episodes of hydrogen generation that depleted available $H_1$ minerals. Observation of high hydrogen potential can also identify other locations within the same geologic province where hydrogen generation rates may be more favorable (i.e., where the current geologic location is not favorable for hydrogen generation but the same rock in other parts of the same geologic province may be more favorable) through the identification of source rocks with high proportions of primary mineral species (e.g., olivine, pyroxenes, and other $H_1$ minerals) capable of generating hydrogen that have not yet been altered. Importantly, the mineralogy of the sample can be used to estimate remaining potential volumes of hydrogen generation in each scenario.

Standard "conventional" geologic hydrogen exploration workflows necessitate the development of a method to score and rank high-quality targets that incorporates the evaluation of multiple components including source rock quality, migration pathways, prospective reservoirs, prospective traps, and prospective sealing lithologies. Robust source rock evaluation tools are also required to rank prospective hydrogen systems at various scales such as globally, within a particular region, within a country, within a basin or system, or even within a borehole.

High-quality source rock targets for "conventional" geologic hydrogen exploration include iron-rich formations that have generated significant volumes of hydrogen that would have migrated through subsurface formations and potentially accumulated within reservoirs that are contained within structural or stratigraphic traps and sealed by a low permeability lithology that impedes further buoyant advective flow. In that scenario, the ideal geologic hydrogen source rock will have a present mineralogy dominated by secondary mineral phases (e.g., $H_2$ minerals such as magnetite and hematite) that have already generated hydrogen during the alteration of the initial composition that contained a high abundance of primary minerals involved in hydrogen generation (e.g., $H_1$ minerals such as olivine and pyroxene) and low proportions of other unrelated minerals (e.g., $H_0$ minerals such as quartz and plagioclase). In that ideal scenario, the gas extracted, measured, and quantified will show evidence of hydrogen generation, but absolute volumes of hydrogen may not be elevated if hydrogen has migrated out of formation and accumulated into an overlying reservoir or been lost by degradation or migration to the surface. Though some "conventional" hydrogen source rocks will not be completely altered, the optimal hydrogen source rocks for these systems will have significantly elevated ratios of $H2_{EV}/H2_{RPV}$ (i.e., maximum possible hydrogen generation has already occurred). As an analog to petroleum systems, ideal source rocks for hydrogen systems have high $H_2/H_1$ mineral ratios, elevated total iron ($Fe_{total}$), with significantly elevated $H2_{EV}$. Other successful source rocks in petroleum systems exhibit analogous characteristics regarding past hydrocarbon generation and remaining hydrocarbon generating potential but can still undergo further hydrocarbon generation. Thus, a sample with elevated $H2_{EV}$ and significant $H2_{RPV}$ may still represent a quality hydrogen source rock for conventional exploration.

"Unconventional" exploration would target hydrogen source rocks that serve as hydrogen source rock-reservoir combinations. This exploration method is in some ways analogous to exploration for some organic-rich shales or tight carbonates as observed in shale gas exploration. "Unconventional" geologic hydrogen exploration workflows involve identifying high-quality source rocks that have generated significant volumes of hydrogen that either have accumulated hydrogen within source rock-reservoirs or are actively generating hydrogen at economic rates and volumes. In either of these scenarios, the idealized hydrogen source rock will show evidence of hydrogen generation as demonstrated by high amounts of $H_2$ minerals (e.g., magnetite, hematite), and the gas extracted, measured, and quantified will contain elevated hydrogen that is similar in volume to the modeled hydrogen generated ($M_2$). This scenario would suggest that hydrogen generated by a hydrogen source rock was also retained within the source rock.

Standard "unconventional" hydrogen exploration workflows necessitate the development of a method to score and rank high-quality source rock targets. A method to meet that need is disclosed that incorporates a geochemical evaluation of source rock lithology, mineralogy, volumes of existing gas content, and extent (e.g., mapping areal coverage and thickness). Robust hydrogen source rock evaluation tools are also required to rank prospective "unconventional" hydrogen systems at various scales, such as globally, within a particular region, within a country, within a basin or system, or even within a borehole.

A method to score and rank high-quality source rocks must be developed in order to identify specific targets for stimulated or enhanced hydrogen production (EHP) or permanent carbon or sulfur sequestration through various mineralization scenarios. Exploration for various EHP or mineralization scenarios necessitates the identification of high-quality hydrogen source rocks that can be altered by engineering processes to cause active generation of significant volumes of hydrogen or mineralization of significant volumes of carbon or sulfur. Ideal target source rocks for various EHP or mineralization scenarios can be characterized by their mineralogic compositions that are nearly exclusively comprised of primary $H_1$ minerals (e.g., olivine and pyroxene) associated with future hydrogen generation. The optimal source rocks for various EHP or mineralization scenarios will contain a high concentration of iron ($Fe_{total}$) and show relatively high volumes of potential hydrogen gas with minimal to no evidence of alteration (low $H_2/H_1$ mineral ratio).

The methods described above and below detail the processes to assess the hydrogen generation capability (past or future) of a geological sample, place that data into the context of hydrogen systems based on its associated mineralogy and compare the volumetric estimations of past hydrogen generation with the volumes of hydrogen retained within prospective source rock targets. The background, methods, and embodiments disclosed below document a series of novel methods to evaluate source rock quality for geologic hydrogen systems and develop the capability to categorize, rank, and high-grade geologic hydrogen source rocks for a variety of exploration approaches.

Further, the systems disclosed herein may include a computing device having at least one processor and a memory storage storing data and one or more operational programs thereon for implementing certain steps of the methods disclosed throughout the present application. The memory storage (e.g., a non-transitory memory storage medium) is in electronic communication with the processor in electronic communication. The system includes a communication network in electronic communication with the computing device. The computing device may include one or more servers, one or more computers (e.g., desk-top computer, lap-top computer), or one or more mobile computing devices (e.g., smartphone, tablet, etc.). The processor of the computing device includes hardware for executing instructions (e.g., instructions for carrying out one or more portions of any of the methods disclosed herein), such as those making up an operational program. The processor is configured to read and execute operational programs stored in the memory storage.

The memory storage of the computing device may include one or more of volatile and non-volatile memories, such as Random Access Memory (RAM), Read Only Memory (ROM), a solid state disk (SSD), Flash, Phase Change Memory (PCM), or other types of data storage. The memory storage may be internal or distributed memory. The one or more operational programs stored in the memory storage may include machine readable and executable instructions for performing any of the portions of the methods disclosed herein. The memory storage also has a data storage therein for storing one or more sets of data, outputs of the methods disclosed herein, or any other digital information used in the methods disclosed herein.

Geologic Hydrogen Source and Hydrogen Generation Processes

The most prevalent high-quality source rocks for geologic hydrogen systems consist of iron-rich rock, iron-rich mafic, or ultramafic rock (e.g., basalt, gabbro, diabase, dolerite, peridotite, dunite) with large proportions of iron in the reduced form ($Fe^{2+}$, or less commonly $Fe^0$), or other rocks with large proportions of minerals containing iron in the reduced form ($Fe^{2+}$, or less commonly $Fe^0$). Example rock types include metamorphosed or hydrothermally altered mafic or ultramafic igneous rock, olivine- or pyroxene-bearing metamorphic or sedimentary rock or sediment, metamorphosed or hydrothermally altered olivine- or pyroxene-bearing metamorphic or sedimentary rock or sediment, serpentine mineral-bearing rock or sediment, partially or completely serpentinized rock, serpentinite, eclogites, prehnite-pumpellyites, amphibole-rich igneous or metamorphic rock, amphibolite, pyrite-bearing rock, or an iron-rich or other metalliferous ore deposit.

As these geologic hydrogen source rocks undergo alteration through water-rock interactions, hydration, hydrothermal alteration, or metamorphism, the reduced forms of ferrous iron ($Fe^{2+}$), or less commonly metallic iron ($Fe^0$), contained in various iron-rich mineral assemblages are oxidized to ferric iron ($Fe^{3+}$) and behave as an electron donor that can react with other chemical species in the subsurface. In most instances, the $Fe^{3+}$ generated by these processes is incorporated into secondary mineral products resulting from the alteration processes described above.

Figure 6:
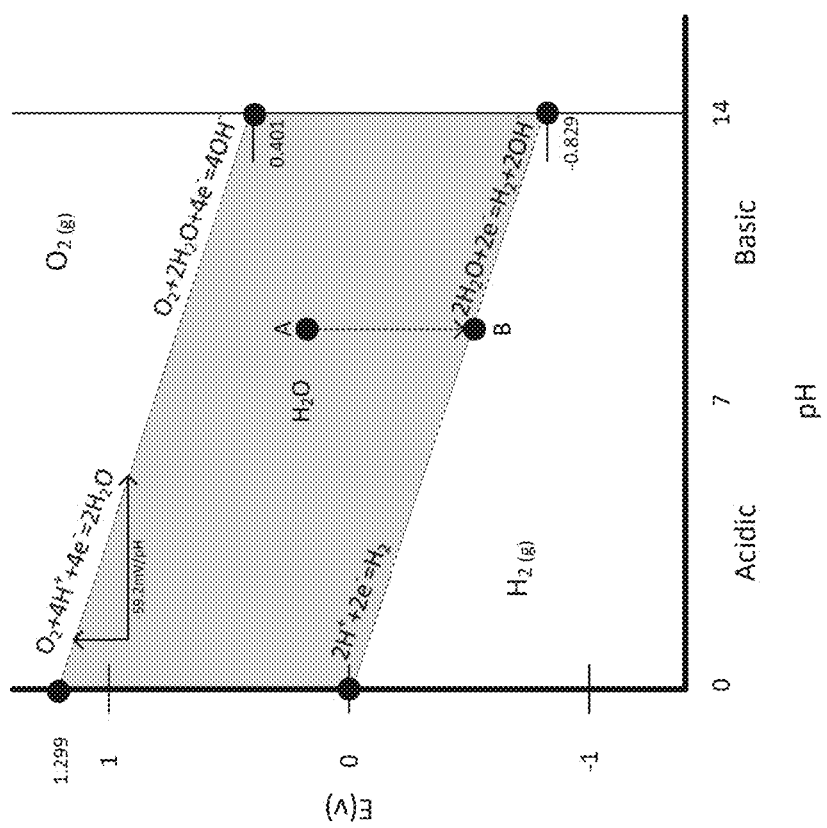
FIG. 6 is a Pourbaix diagram showing the water stability field based on oxygen fugacity and pH values.

In a variety of subsurface environments, the free electron created by this process (e.g., during serpentinization) can interact with and reduce water (i.e., lower the oxygen fugacity) to produce hydrogen gas ($H_2$), as shown in FIGS. 5 and 6.

The conditions under which mineral hydration alteration reactions capable of generating hydrogen occur are controlled by the molar abundance of various reduced forms of iron or other redox sensitive elements (e.g., manganese (Mn), chromium (Cr)) and the lack of alternative oxidizing species (e.g., $O_2(g)$, $SO_4^{2-}$, $HCO_3^-$) inside the stability field of water. When pore fluids are depleted in these electron acceptors during the alteration reactions described above, $Fe^{3+}$ will be incorporated into thermodynamically stable (or metastable) mineral phases and water will be reduced to form hydrogen gas.

In addition to variations in pore water chemistry, further complexity stems from the fact that $Fe^{2+}$ may be incorporated into several types of minerals, which have varying degrees of reactivity. For example, some minerals react quickly, while others have kinetic limitations to alteration. The mineral alteration products formed during water-rock interactions may also contain variable concentrations of iron with exclusively $Fe^{2+}$, exclusively $Fe^{3+}$, predictable proportions of $Fe^{2+}$ and $Fe^{3+}$, or variable proportions of $Fe^{2+}$ and $Fe^{3+}$. If $Fe^{2+}$ is incorporated into the mineral alteration phase without undergoing oxidation, it will not serve as an electron donor and thus will not participate in hydrogen generation. Because secondary minerals formed by various reactions may also have varying ratios of $Fe^{3+}/Fe^{2+}$ and degrees of reactivity that have the potential to generate additional hydrogen, it is critical to evaluate the remaining hydrogen generation potential through laboratory measurements.

The alteration products formed by earlier episodes of hydrogen generation that do contain $Fe^{2+}$ (e.g., magnetite) may alter further to form additional hydrogen or, alternatively, these mineral phases may be fully stable and incapable of forming additional hydrogen. As such, a comprehensive data set that includes bulk elemental composition (often expressed as major oxides), the mineral assemblage (i.e., relative proportions of each mineral in a given rock, also termed "modal mineralogy"), the iron content of each iron-bearing mineral phase, and the oxidation state of that iron in each mineral phase (i.e., $Fe^{3+}/Fe_{total}$ or $Fe^{2+}/Fe_{total}$) is needed to fully quantitatively evaluate hydrogen source rocks. Measurements of the hydrogen gas in rock samples provide further constraint on the suitability of a sample to serve as a hydrogen source rock.

Gas Measurements of Existing Volumes of Hydrogen ($H2_{EV}$)

Gas contained within samples of hydrogen source rock can include hydrogen sourced from volumes already generated via alteration reactions and/or hydrogen and other gases generated elsewhere that migrated into source rocks and accumulated over geologic time (i.e., from external sources). The volumes of gas generated can be associated with hydrogen source rock maturity. The existing volumes of hydrogen ($H2_{EV}$) can be measured from these samples and quantified (on a per mass or per volume basis) as part of a comprehensive evaluation of the source rock.

The mineral properties of the rock sample (e.g., current mineral composition, estimates of the original mineral content using modal or normative mineral models, and/or quantitative assessments of the altered minerals that were likely formed during past episodes of geologic hydrogen formation) can be used to predict theoretical volumes of hydrogen generation (either past or future) that are compared to the measured $H2_{EV}$ for the same rock. This allows for estimates of the volume of hydrogen gas that has remained within hydrogen source rocks (i.e., accumulated in prospective unconventional source rock-reservoir) and differentiates that from the volume of hydrogen that was liberated from the source rock and possibly migrated to overlying conventional hydrogen reservoirs into trapping geometries sealed by low permeability formations.

Loss of hydrogen from a hydrogen source rock can be due to primary migration (i.e., migration within and out of source rock). Hydrogen that migrates out of the source rock can migrate by secondary migration as a buoyant gas phase, dissolved in water, or be carried by another gas phase. After hydrogen gas migrates out of source rocks, it can accumulate within reservoirs and be contained by seal-capped traps or diffuse or advect and eventually be discharged to the atmosphere without accumulating. The ability to quantify the volumes of hydrogen that enter the conventional reservoir-trap-seal systems is critical to developing robust hydrogen systems exploration models and has important economic implications for the exploration of "conventional" geologic hydrogen systems that have accumulated hydrogen in reservoirs. By comparison, the amount of hydrogen that is retained within a hydrogen source rock quantifies the potential for natural hydrogen production from unconventional reservoirs, either from production in source rock-reservoirs or hydrogen that has migrated into and accumulated in source rocks.

Holistic analysis of a source rock includes assessing the sample's mineralogy to predict (molar) volumes of past hydrogen generation by formation of secondary minerals ($M_2$) based on normative or modal mineralogy methods. These theoretical predictions can then be compared to the $H2_{EV}$ of the same sample to investigate the fate of hydrogen generated in the system. For example, if hydrogen measured from the sample exceeds the amount predicted by mineralogy ($H2_{EV} \gg M_2$), hydrogen was likely generated elsewhere in the system and the sample likely represents a lithologic unit that has realized hydrogen accumulation (i.e., an example of an accumulation in an unconventional source rock reservoir; FIG. 7). If the hydrogen measured from the sample closely matches the amount predicted by mineralogy ($H2_{EV} \approx M_2$), it is likely that the hydrogen was generated and remained accumulated/trapped within the unit of the source formation that was sampled (i.e., an example of an unconventional source rock-reservoir; FIG. 7). If instead the hydrogen measured from the sample is much less than the amount anticipated based on its mineralogy ($H2_{EV} \ll M_2$), the rock represents a zone of significant hydrogen removal from source rocks which could be the source for accumulation in overlying conventional or unconventional reservoirs (i.e., an example of a source rock for conventional or unconventional accumulations; FIG. 7) or evidence for hydrogen degradation by chemical or biological consumption; additional workflows described elsewhere are capable of differentiating among these possibilities. Several methods are described below that measure hydrogen from source rock samples to estimate $H2_{EV}$ and place the rock into the context of the hydrogen system.

Without physically altering (e.g., pulverizing) geologic material, 'mobile' gases may be manually extracted by advection or diffusion along pressure or concentration gradients and measured in the laboratory. For example, methods of 'mobile' gas extraction may involve placing geologic sample material within a gas-tight vessel and exposing the vessel to a static vacuum, allowing advection and diffusion to release gas from the geologic sample. Gas extraction may be facilitated by methods that include heating by a band heater, laser, external heating jacket, or other means. All systems and devices for expediting the rate of gas release are considered. An example of our preferred embodiment involves exposing the geologic sample contained within a gas-tight vessel to a static vacuum and using the differential pressure between gas trapped in the material and the pressure of the vacuum to facilitate movement of gas out of the geologic material. Once extracted, the gas sample can then be injected into an instrument system.

The 'mobile' gases will then be analyzed by various analytical methods, which are discussed in detail below. When using gas extraction particularly by way of pressure and concentration gradient, gas extraction out of the geologic material and into the system disclosed herein may be used to quantify 1) the pressure of the sample, which can be used to calculate the initial total pressure (or at least a minimum total pressure) of gas in the subsurface system and hence better estimate the total volume of hydrogen gas in place prior to drilling; 2) the proportion of 'mobile' hydrogen or other gases; 3) the total volume of hydrogen which can be used to calculate $H2_{EV}$; and 4) the relative permeability of hydrogen and other individual gas species in the rock sample by measuring the rates of hydrogen release (i.e., measured by pressure changes over time and evaluating the rate or slope of pressure change) over time; these measurements can be used to calculate the relative permeability of hydrogen for a specific rock-fluid pair in subsurface conditions.

Using alternative methods, the geologic sample (e.g., drill cuttings, mineral grains, sediment) may be physically altered (i.e., through crushing) to determine hydrogen (including 'mobile' and 'immobile' hydrogen) and other gas phases. The total hydrogen released when using pulverization or crushing methods can be compared to the 'mobile' proportion to evaluate hydrogen behavior, represent the prospective $H2_{EV}$, and allow for quick quantification of hydrogen volumes in a given sample. Alternatively, after a sample is allowed to degas completely, the 'immobile' gases previously trapped in isolated pore spaces or fluid inclusions within geologic material can be released through the new migration pathways formed by crushing and similarly analyzed using high-vacuum extraction and mass spectrometry methods described above and below. In so doing, analyzing the volume calculated from the pressure of a known volume change and chemistry of the fluid released during crushing or pulverization of fresh geologic material allows for the quantification of $H2_{EV}$. However, because migration pathways are being created, this technique cannot quantify total hydrogen mobility or relative permeability out of a geologic material and may overestimate the relative contribution of fluid inclusions.

Methods of Estimating Remaining Potential Volumes of Hydrogen ($H2_{RPV}$)

In addition to past hydrogen generation, hydrogen source rocks have the potential to generate additional hydrogen proportional to the mass of primary $H_1$ minerals (minerals with hydrogen generating potential that remain unaltered by water-rock interactions) and some secondary $H_{2a}$ minerals (altered minerals that can react again to generate hydrogen). One method to predict remaining hydrogen generating potential involves using normative or modal mineralogy models. Laboratory measurements can be performed to determine the optimal conditions (e.g., pressure, temperature) that induce complete mineral alteration and yield full hydrogen gas generation. If the source rock material is subjected to pressure, temperature, and fluids that can generate hydrogen in the laboratory, the resulting hydrogen gas volumes can be measured to estimate and quantify the remaining potential volumes of hydrogen ($H2_{RPV}$, on a per mass or per volume basis). These measured $H2_{RPV}$ values of rock samples can then be compared to the potential volumes of hydrogen predicted by mineralogy.

The present embodiment involves exposing samples of geologic materials to a range of temperature or pressure conditions, or multiple stages of temperature increases at a constant pressure, or a range of pressure and temperature conditions that are stepwise increased: 1) in the presence of idealized fluid composition or 2) in the presence of pore fluid composition consistent with the subsurface conditions from which the sample was collected. In so doing, the differing temperature, pressure, and fluid composition conditions may represent changes in the geologic environment within which the hydrogen source rock existed through its evolutionary history or idealized conditions that yield the maximum volume of hydrogen generation. As another example, this embodiment may be used to simulate the increase in temperature or pressure related to increased burial in the subsurface.

Another embodiment may be used to simulate the decrease in temperature related to cooling of an igneous body after the magma was emplaced and began to cool, during decreasing geothermal gradients following cooling of geothermal systems, or following obduction or uplift and denudation. Or alternatively, one embodiment simulates decreasing temperature due to erosion and denudation of material that may have been overlying the hydrogen source rock at some time in the geologic past or following obduction of hydrogen source rocks.

One embodiment involves performing laboratory experiments that mimic in situ temperature, pressure, and formation fluid chemistry conditions by matching those with the geologic province in which the hydrogen source rock exists. These experiments may involve the use of present temperature or pressure conditions (e.g., by using depth data, bottom hole temperature data, or geothermal gradient data), elevated pressure or temperature conditions that exceed the current geologic conditions, or pressure and temperature conditions determined from geologic reconstruction to simulate past episodes of hydrogen generation.

In an example of this embodiment, experiments that utilize current pressure or temperature conditions or formation fluid chemistry may be used to quantify how much hydrogen a source rock may generate in its current state. Alternatively, in another example of this embodiment, elevated (or lower) pressure or elevated (or lower) temperature conditions may be used in laboratory experiments to identify the ideal reaction conditions for a specific hydrogen source rock that had higher pressure or temperature conditions during previous episodes of hydrogen generation. Results from these measurements can be incorporated into estimates of hydrogen generation and hydrogen systems models to reconstruct the volume and timing of hydrogen generation.

In another embodiment, laboratory experiments may use modified pressure or temperatures conditions, or synthetic formation fluid chemistries representative of the conditions that hydrogen source rock had been subjected to at some time in the geologic past (e.g., deeper (or shallower) in the subsurface or at higher (or lower) temperatures such as during basin formation, magma intrusion, a volcanic eruptive period, a period of obduction, uplift, and denudation, or during a period of more extensive water-rock interactions). In this manner, the temperature or pressure conditions or fluid chemistry used during the laboratory experiments may represent in situ conditions in the geologic past, which may be used to quantify the rate of hydrogen generation and the volume of hydrogen that may have been generated during specific periods in the geologic past.

Alternatively, in this embodiment, the laboratory experiments may use synthetic fluids that are representative of the natural fluids that exist in or around the hydrogen source rock formation in its geologic environment (e.g., based on pH, oxygen fugacity, or dissolved solute composition). In this embodiment, the fluids used to develop synthetic analogs for the reactants used during the laboratory experiments may be: 1) collected during drilling or during a drill stem test (DST), formation test, flow test, production test, or other test meant to test specific intervals in the subsurface, or from a producing well, monitoring well, groundwater well, geothermal well, or other well that may produce liquids, 2) measured directly from wireline logging, or measurement while drilling (MWD) tools, or 3) estimated based on available regional subsurface data and geologic history.

These methods enable calculation of the hydrogen generation potential for hydrogen source rocks. Comparison of the experiment results from the two reaction methods (optimized fluid chemistry determined from an experiment matrix of synthetic rocks versus natural fluid chemistry collected in the field) provides information about optimal hydrogen generation and the favorability of hydrogen generation for a hydrogen source rock in a given geologic province, or suggest the hydrogen source rock has greater potential for hydrogen generation if the hydrogen source rock is present in other areas of a geologic province where the conditions (e.g., temperature, depth, pore fluid composition) are more favorable for hydrogen generation (e.g., an igneous intrusive complex where a deeper intrusive hydrogen source rock is in a more favorable location for hydrogen generation than a shallow intrusive hydrogen source rock of similar mineralogy).

In this embodiment, the current mineral composition and calculations of the original mineral content performed using modal or normative mineral models of the rock sample can be used to predict theoretical volumes of future hydrogen generation from alteration of primary minerals ($M_1$). These results can then be compared to the measured $H2_{RPV}$ for the same rock. In this embodiment, these values may be compared to one another and be combined with kinetic models of hydrogen generating reactions to validate the hydrogen yield based on source rock mineralogy. Additionally, in this embodiment, by comparing the actual hydrogen yield to the theoretical value, the reaction efficiency can be determined. The reaction efficiency is used to estimate kinetic rates of alteration for bulk material (or specific mineralogy) to determine how much of the rock (or which mineral phases) can react quickly enough to be relevant to hydrogen generation via engineered processes (e.g., EHP). These models will be used to design stimulation and drilling processes to maximize hydrogen generation. Rocks where the current (observed) mineralogy differs only slightly from the original mineralogy (e.g., predicted via normative mineralogy calculations based on oxide content) have experienced minimal hydrogen generating alteration but may release hydrogen in economic quantities if conditions (e.g., pressure, temperature, water chemistry) change, which can occur elsewhere in the natural system or by altering the conditions through the engineered EHP processes.

In this embodiment, these theoretical predictions may be compared to the measured $H2_{RPV}$ of the same sample to investigate the suitability of the rock to generate hydrogen in the future and to evaluate the source rock potential of the sample. If for example the amount of hydrogen generated from the sample during laboratory stimulation processes closely matches the amount predicted by mineralogy ($H2_{RPV} \approx M_1$) and greatly exceeds the existing volumes of hydrogen ($H2_RPV \gg H2_{EV}$), the source rock has undergone minimal alteration in its current location but could serve as a source rock that generates hydrogen either: 1) naturally elsewhere in the system (i.e., in another portion of the geologic province where the same formation is at a different depth or geothermal gradient profile with temperature and pressure more suitable for hydrogen generation) or 2) as a target for engineered stimulation techniques (e.g., EHP). Several methods that measure hydrogen from source rock samples to estimate $H2_{RPV}$ and place the rock into the context of the hydrogen system are described below.

Review of Systems for Hydrogen Source Rock Evaluation

Quality geologic hydrogen source rocks are defined by a set of typical characteristics depending on their suitability as "conventional," "unconventional," or EHP targets/"provincial" targets.

Ideal natural hydrogen source rocks for "conventional" natural hydrogen exploration will exhibit a high score for hydrogen source relevance (i.e., elevated iron content and high $H_2/H_1$ mineral ratio), an elevated mafic alteration index (i.e., elevated magnetic susceptibility related to hydrogen generation and production of $H_2$ minerals such as magnetite and hematite), an elevated source rock maturity index (i.e., mineralogy dominantly $H_{2a}$ and $H_{2b}$), high iron content with moderate to low silica, and other indications of hydrogen-generating alteration (e.g., high HAI score) described elsewhere [Eymold et al., 2024]. Similarly, the highest quality source rocks for "unconventional" natural hydrogen exploration will exhibit a high score for hydrogen source relevance, an elevated mafic alteration index, elevated magnetic susceptibility, an elevated source rock maturity index, and a high HAI score.

In contrast, quality source rocks for enhanced hydrogen production (e.g. zones within the geologic province containing the same hydrogen source rock, but in an environment that has not yielded as excessive hydrogen generation) should have a composition dominated by $H_1$ mineral assemblages. The highest quality source rocks for enhanced hydrogen production targets will exhibit a high total iron content, a low $H_2/H_1$ mineral ratio, an intermediate mafic alteration index/magnetic susceptibility, a low source rock maturity index and a high source rock potential index (i.e., high $H_1$ content with minimal to no $H_0$ and $H_2$ minerals), and a low HAI score.

Determining the volume of hydrogen trapped within samples of geologic material as well as the remaining volumes of hydrogen generating potential can therefore be used in conjunction with these other methods to evaluate the quality of a source rock. Different methods described below estimate the amount of hydrogen already generated and compare that volume with the amount of hydrogen that can be generated if a rock is stimulated further (e.g., via EHP) or was previously generated in areas where the same hydrogen source rock has been, or is currently, exposed to more preferable geologic conditions for hydrogen generation (e.g., provincial targets). Laboratory analysis provides metrics to first assess the hydrogen generation that already occurred and then estimate the volume of hydrogen that can potentially be generated, while also constraining the temperature, pressure, and fluid conditions that would produce the highest yield. This series of novel methods presented in this disclosure evaluates source rock quality for natural hydrogen systems and develops the capability to categorize, rank, and high-grade natural hydrogen source rocks for a variety of exploration approaches.

If the past hydrogen generation ($M_2$) predicted from current mineralogy is considered a maximum yield on a per volume of rock basis, the amount of directly measured hydrogen ($H2_{EV}$) can be considered a minimum. Moreover, the $H2_{EV}$ can be compared to $M_2$ to estimate hydrogen generation efficiency (or local retention within the source formation) and rectify the discrepancy between the two values. Missing volumes of hydrogen (e.g., $V=M_2-H2_{EV}$) can be absent in the source rock for a number of reasons: 1) hydrogen can migrate out of the source rock to accumulate (or degas from the surface), 2) hydrogen can react with other chemical constituents (e.g., $O_2$, $SO_4^2$, $CO_2$) and be lost from the gas phase, or 3) hydrogen can be metabolized by biologic processes (e.g., microbial sulfate reduction or methanogenesis). The fate of these lost volumes of hydrogen must be considered by other exploration workflows but may constrain the volumes of hydrogen in source rocks that may have migrated into and accumulated in conventional reservoirs.

When exploring for conventional geologic hydrogen targets, the ideal geologic hydrogen source rock will have a high initial proportion of $H_1$ and $H_2$ minerals (i.e., minerals rich in iron and other mafic components) and a low proportion of $H_0$ minerals. In contrast, geologic materials that do not possess relevant proportions of $H_1$ or $H_2$ minerals are classified as non-hydrogen source rocks. Specifically, non-hydrogen source rocks are dominated by $H_0$ minerals, with scarce $H_1$ and $H_2$ minerals ($H_0 \gg H_1+H_2$). Likewise, the calculated moles of remaining hydrogen generation potential ($M_1$) are low, as are volumes of past hydrogen generation ($M_2$). Lastly, the measured $H2_{EV}$ and $H2_{RPV}$ are both minimal, indicating that the rock possesses no past or remaining future hydrogen generating potential, respectively. In this scenario, the non-hydrogen source rock should not be considered as a source within a hydrogen system.

In an embodiment, when evaluating hydrogen source rocks within the context of the broader hydrogen system, considerations of the present mineralogy (i.e., relative amounts of $H_0$, $H_1$, and $H_2$ minerals), predictions of past or future hydrogen generation ($M_1$, $M_2$), and gas measurements of existing volumes ($H2_{EV}$) and remaining potential volumes ($H2_{RPV}$) of hydrogen can be used in conjunction to categorize geologic material as: 1) non-source rock for hydrogen or 2) hydrogen source rock that a) serves as an unconventional source rock-reservoir, b) represents accumulation in unconventional source rock-reservoirs, c) has characteristics of source rock for conventional accumulations, or d) is an unaltered source rock for EHP, mineralization, or 'provincial' targets (FIG. 7).

Using the methods disclosed herein for evaluating geologic hydrogen source rocks, geological samples can be scored based on both source rock maturity and source rock potential (FIG. 7). From this output, other hydrogen exploration workflows (e.g., source rock mapping, reservoir mapping, basin analyses) can be used to develop hydrogen systems models that consider migration, reservoir, trap, seal, and preservation.

"Unconventional" geologic hydrogen exploration involves identifying high-quality source rocks that have generated significant volumes of hydrogen that has accumulated within source rock-reservoirs or that are actively generating hydrogen at economic rates and volumes. The ideal unconventional hydrogen source rock would serve as a combined hydrogen source rock-reservoir and will contain a large volume of hydrogen. In this scenario, the mineralogy would be dominated by $H_{2a}$ and $H_{2b}$ minerals ($H_{2a}+H_{2b} \gg H_0+H_1$), and the measured moles of hydrogen would be comparable to the predicted moles of hydrogen generated based on mineralogy ($H2_{EV} \approx M_2$), suggesting that generated hydrogen has been retained by the producing formation. Additional scenarios where $H2_{EV} > M_2$ would suggest accumulation of hydrogen and the source rock may represent a productive unconventional hydrogen reservoir.

Other example scenarios where hydrogen source rocks may be targeted for conventional or unconventional hydrogen exploration involve identifying larger volumes of hydrogen within hydrogen source rocks than what is the estimated volume of past generation ($M_2$) based on the geologic material's mineralogy and elemental composition. In this scenario, source rocks may serve as a reservoir and/or seal for hydrogen gas that was generated in underlying formations and migrated (i.e., the hydrogen source rock is fractured enough to serve as an unconventional reservoir with zones of impermeable seals). This may occur, for example, where multiple layers of mafic rock are deposited or stacked intrusive igneous bodies exist.

In another example scenario where the hydrogen source rock is particularly massive (e.g., hundreds or thousands of feet thick), hydrogen may have been generated in specific intervals of the hydrogen source rock body (e.g., where water was able to migrate into or where the mineralogy and geologic conditions were particularly favorable for hydrogen generation) and migrated along internal migration pathways (e.g., fracture networks) and accumulated within porosity (e.g., open fractures, fault zones, microporosity within altered minerals) that is capped by a low permeability, sealing interval (e.g., unfractured or unaltered zones or low permeability marine evaporites or shales). In each of these scenarios, the predicted volumes of hydrogen generated may be less than the volumes of hydrogen measured from the source rock ($M_2 \ll H2_{EV}$), especially if the measured source rock containing the hydrogen has less favorable mineralogy and/or geologic conditions than the actual hydrogen source rock or interval of the hydrogen source rock body from which the hydrogen was generated. Importantly, this embodiment can be used to rank prospective hydrogen systems at various scales. For illustrative purposes, this can include on global scales, within a particular region, within a country, within a basin or system, or even within a borehole.

While ideal unconventional hydrogen source rocks will have values of $H2_{EV}$ and $M_2$ that are nearly equal, formations may still be considered as an unconventional target if the $H2_{EV}$ is elevated but not in agreement with the predicted volume ($M_2$) based on the geologic material's mineralogy and elemental composition (i.e., the measured hydrogen is less than what was predicted). This would suggest some (but not complete) loss of generated hydrogen, in an analogous manner to hydrocarbon source rocks that have already lost some of their hydrocarbons but are still targeted for unconventional exploitation. Additional exploration workflows developed elsewhere would be required to identify specific targets for unconventional geologic hydrogen exploration in the hydrogen system with these characteristics. Importantly, this embodiment can be used to rank prospective hydrogen systems at various scales. For illustrative purposes, these various scales can include global scales, within a particular region, within a country, within a basin or system, or even within a borehole.

High-quality hydrogen source rock targets for "conventional" geologic hydrogen exploration include iron-rich formations that have generated significant volumes of hydrogen that would have migrated through subsurface formations and potentially accumulated within reservoirs that are contained within structural or stratigraphic traps and sealed by a low permeability lithology that impedes further buoyant advective flow or extensive diffusive loss. In conventional geologic hydrogen systems, if the hydrogen source rock contains minerals suggesting hydrogen has been generated ($H_{2a}$, $H_{2b}$), but the measured hydrogen is much less than the amount anticipated based on its mineralogy and elemental composition ($H2_{EV} \ll M_2$), the rock represents a loss zone (e.g., gas has migrated away from the hydrogen source rock or was otherwise consumed by biological or chemical processes; these two processes can be differentiated by other workflows disclosed elsewhere), which could be promising for the potential for accumulation in overlying conventional reservoirs.

In the case of an idealized conventional hydrogen exploration system, the hydrogen source rock would display an elevated $H_2/H_1$ mineral ratio, reduced $M_1/M_2$, depleted $H2_{EV}$ and $H2_{RPV}$, and elevated total iron content or retain residual hydrogen generating potential and be in the conditions of active hydrogen generation (i.e., relatively high $H_2/H_1$ mineral ratio with active generation and hence potential for active reservoir charging).

Less altered source rock (lower $H_2/H_1$ mineral ratio) can still provide important context for "conventional" geologic hydrogen system targets if the measured hydrogen is depleted relative to the predicted volumes ($H2_{EV} \ll M_2$), suggesting hydrogen has migrated away from the source rock or was otherwise consumed by biological or chemical processes; these two processes can be differentiated by other workflows disclosed elsewhere. Additional and standard exploration workflows are required to identify specific targets for conventional geologic hydrogen exploration in these geologic settings based on assessing potential migration pathways, evaluating the relative risk of hydrogen degradation, and mapping the location and evaluating the properties of prospective reservoirs, traps, and seals. Importantly, the outputs of this embodiment can be used to score and rank prospective hydrogen systems at various scales. For illustrative purposes, these various scales can include global scales, within a particular region, within a country, within a basin or system, or even within a borehole.

Hydrogen source rocks that do not presently have an abundance of existing hydrogen but possess a high potential for future hydrogen generation represent targets for EHP, mineralization, or "provincial" targets, where the same source rock is located elsewhere in the same geologic province but in areas with geologic conditions more favorable for hydrogen generation. Provincial targets may also include regions where the same source rock had been exposed to more favorable conditions for hydrogen generation throughout geologic history. Source rocks may exist in other locations within the same geologic province with more optimal temperature, pressure, water chemistry, and/or lower preservation risks. In either scenario, the idealized hydrogen source rock would contain a high proportion of $H_1$ minerals ($H_1 \gg H_0+H_{2a}+H_{2b}$), and similarly elevated predicted and measured remaining hydrogen generating potential ($M_1 \approx H2_{RPV}$).

While an ideal hydrogen source rock for EHP, mineralization, or provincial targets would show little to no alteration with significant hydrogen generating potential remaining (elevated concentrations of $H_1$ minerals), altered source rock may still be considered for EHP, mineralization, or provincial hydrogen targets if elevated generation potential remains (e.g., high iron, low $H_2/H_1$). Additional and standard exploration workflows are required to identify specific targets for EHP, mineralization, or provincial target exploration in these settings. Importantly, this embodiment can be used to score and rank prospective hydrogen systems at various scales. For illustrative purposes, these various scales can include global scales, within a particular region, within a country, within a basin or system, or even within a borehole.

High-Vacuum Extraction Methods to Estimate $H2_{EV}$ in Source Rocks

A key component of hydrogen system analyses is the careful evaluation of the presence and quality of hydrogen source rocks, as well as the quantitative assessment of the volumes of hydrogen that have been generated from those source rocks. Novel systems and methods must be developed in order to quantify the existing volumes of hydrogen (i.e., $H2_{EV}$) that are present within a given sample of hydrogen source rock. The approach disclosed herein produces a metric that is conceptually analogous to estimating the S1 component of petroleum source rocks using Rock-Eval® pyrolysis methods developed for petroleum exploration. However, unlike the Rock-Eval® pyrolysis methods, which are incapable of being applied to geologic hydrogen or geologic hydrogen systems, the disclosed apparatus is specifically capable of measuring hydrogen and other relevant analytes in order to evaluate hydrogen systems.

Figure 8:
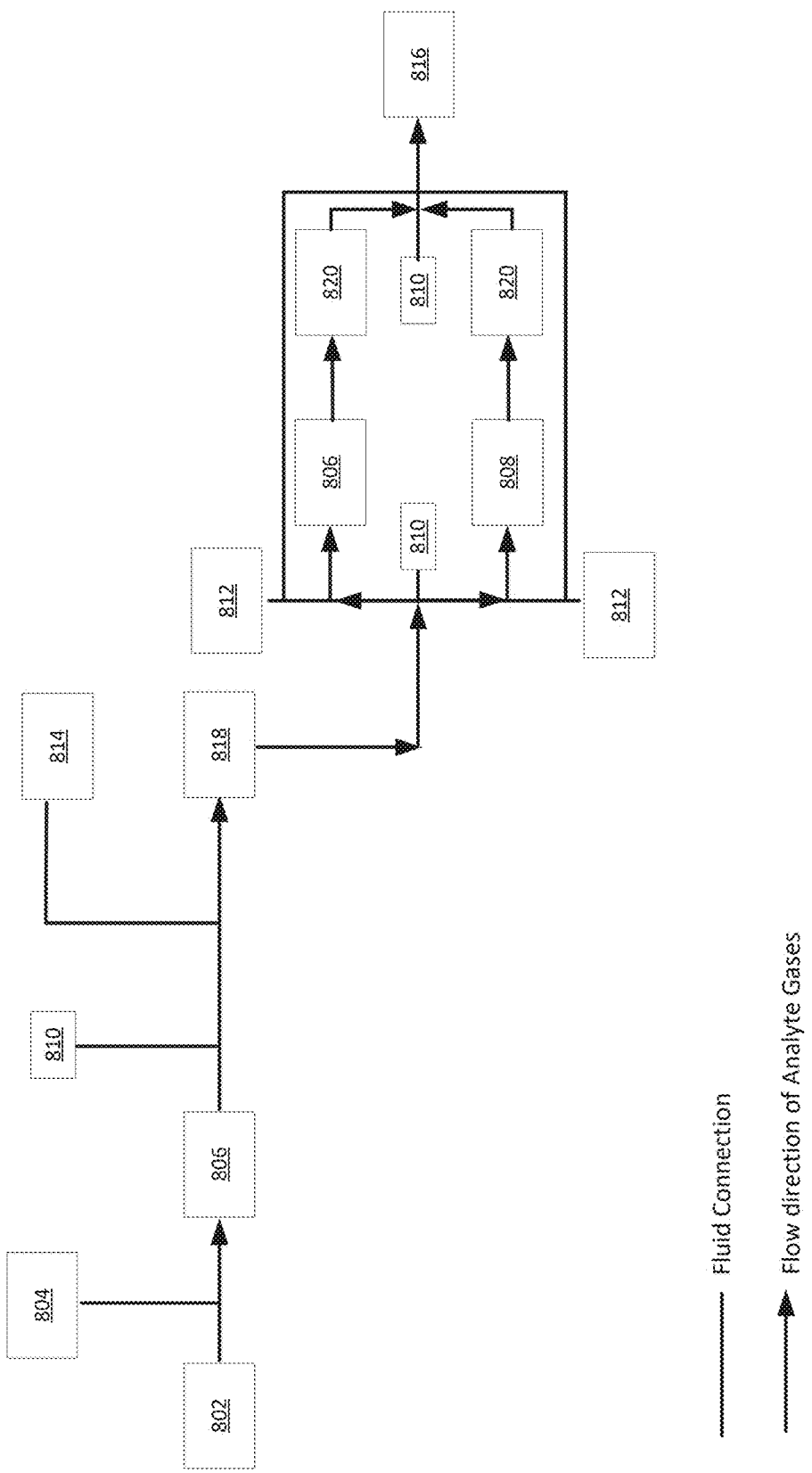
FIG. 8 is an annotated schematic of an example vacuum extraction and analytical system used to extract and detect hydrogen ($H_2$), helium (He), ammonia ($NH_3$), hydrocarbon gases (e.g., $C_1$, $C_2$, $C_3$, $C_{4+}$), nitrogen ($N_2$), carbon dioxide ($CO_2$), various hydrogen-derived chemical species (e.g., dihydrogen sulfide ($H_2S$), hydrogen cyanide (HCN)), or other gases that advect or diffuse out into a gas-tight sample vessel based on changes in pressure or concentration gradients from geologic material, termed 'mobile' gases.

One embodiment discloses systems and methods for sample collection and the analytical device and associated methods designed to extract, detect, and quantify existing volumes of hydrogen ($H_2$), helium (He), ammonia ($NH_3$), various hydrogen-derived chemical species (e.g., dihydrogen sulfide ($H_2S$), hydrogen cyanide (HCN)), hydrocarbon gases (i.e., $C_1$, $C_2$, $C_3$, $C_4+$), nitrogen ($N_2$), carbon dioxide ($CO_2$), or other gases that advect or diffuse from geologic material into a gas-tight sample vessel, for subsequent analyses as shown in FIG. 8.

An embodiment of the present disclosure involves the use of known volumes of geologic sample material that are then placed into gas-tight sample vessels of known volumes. The absolute volume of sample may change depending on the size of the sample vessel used, but by using known volumes of both the sample and sample chamber, one can estimate important parameters, such as volumes of atmospheric contamination and initial pressure can be accurately quantified. If the geologic material is wet or covered with mud (e.g., drilled with water, water-based mud, oil-based mud), such as drill cuttings collected quickly after entering mud circulation while drilling a well or borehole, coring, or other, the material may be sampled immediately or first dried completely or partially before sampling. The unconsolidated geologic material may be loaded directly into the sample vessel without further sample preparation. Other geologic materials, such as core collected while drilling a well or borehole, or rock sample collected at the surface may be placed in sampling vessels designed to match the sample volume or if analysis of these samples requires disintegration (i.e., mortar and pestle) and/or sieving to prepare adequate size materials for the extraction system prior to loading into the gas-tight sample vessel. Our preferred embodiment uses sample material with minimal alteration after drilling.

In this embodiment, the gas-tight sample vessel may be made of gas-tight material (e.g., borosilicate glass vial, copper tube, steel tube, Tedlar® bag) and sealed with a cap with rubber or silicon septum, gas-tight valve, or other material with the purpose of preventing gas leakage and later allowing for reliable sample extraction. Sample gas is then extracted by piercing the septum with a needle attached to a gas-tight syringe, opening the valve, or using a similar device that is plumbed to an instrument. The borosilicate or glass sample vessels may include screw cap vials, headspace vials, BD Vacutainers®, or similar containers. In this embodiment, a cylindrical insert (e.g., made of glass or other material) may be used for a known volume in which to fill geologic sample material, which then gets placed into the sample vessel. In another embodiment the sample vessel may be capped by a valve (e.g., needle valve, ball valve, bellows-sealed valve, or other) capable of operating with above atmospheric pressure on one side and below atmospheric pressure on the other side, which may then be opened to allow sample gases that migrated from the sample into the sample vessel to be introduced into a chemical analytical instrument system. (FIG. 9).

Figures 9A, 9B:
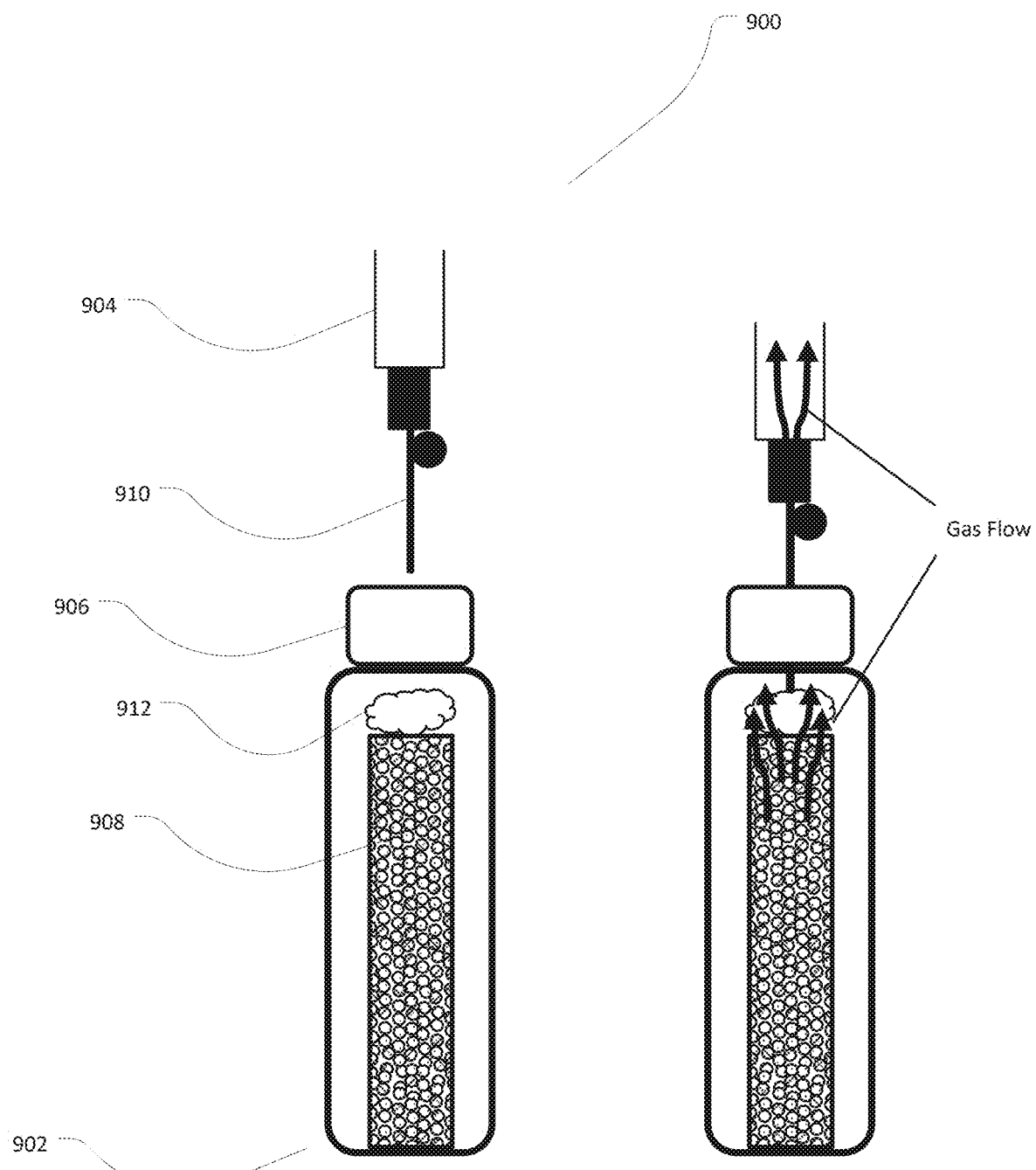
FIGS. 9A and 9B are example annotated schematics of a high-vacuum gas extraction process, using a gas-tight sample vessel loaded with a geological sample as one example for the sample vessel.

FIG. 9 is an example annotated schematic of a high-vacuum gas extraction process, using an apparatus 900 comprising a gas-tight sample vessel 902 loaded with geologic material as one example for the sample vessel. FIG. 9A displays the sealed apparatus 900 prepared for gas extraction, and FIG. 9B shows the gas extraction process, where a needle 910 attached to a static vacuum line 904 pierces a pierceable seal 906 (e.g., a septum cap) or a valve is opened, allowing for the atmospheric gas and gas derived from the geologic material 908 to expand into the vacuum line. The geologic material 908 may be separated from the pierceable seal 906 by additional packing material 912 (e.g., cotton pellets). This expansion increases the pressure gradient between the hydrogen source rock and the vacuum line, enhancing the release of gas from the hydrogen source rock. Single, multiple, sequential, and/or prolonged extractions may be completed to increase the pressure gradient between the hydrogen source rock and the vacuum line, further degassing the sample.

In an embodiment, the sample vessel will contain geologic material, with or without any residual liquid, gas derived from the geologic material, and the remaining volume being filled with atmospheric gas (from the environment within which the vessel was located just prior to the vessel being closed off), impregnated with an inert gas (e.g., noble gases) to prevent hydrogen oxidation, water with a preservative (e.g., biocide), water that has been deoxygenated to decrease the risk of hydrogen oxidation or degradation within the sample vessel with or without a preservative, or other gases or liquids with the purpose of minimizing hydrogen loss in the sample vessel.

In one embodiment the remaining volume not filled by sample material within the vessel will be filled with atmospheric gas. Because the system places a known volume of sample geologic material into a sample vessel with known volume, the amount of atmospheric gases that make up the remaining non-sample filled volume in the sample vessel is quantifiable, and the moles of atmospheric gas can be calculated with negligible errors. The volume of the remaining non-sample filled volume is determined by subtracting the volume of geologic material from the total volume of the gas-tight sealed vessel. At the time of sealing, the volume of air contamination within the gas-tight vessel can be reliably assumed to be pure atmospheric gas (i.e., approximately 78.08% nitrogen, 20.95% oxygen, 0.934% argon, 0.042% carbon dioxide, 18.2 ppm neon, 5.23 ppm helium, 1.5 ppm methane with slight differences depending on the altitude and temperature of the sampling location with a pressure of approximately 1 atm, with slight but measurable variations due to elevation and the ambient pressure, temperature, and humidity in the environment within which the vessel was located just prior to the vessel being closed off). These assumptions and appropriate adjustments will later be used to calculate and remove the atmospheric component of the gas mixture, leaving only the composition and moles of gas derived from the geologic material.

An embodiment of the present disclosure relates to gas being extracted from the geologic material and gas preparation for analysis, referred to herein as the high-vacuum extraction system. As an example, the following process description utilizes a gas-tight vessel that is capped by a screw cap which has a septum in the middle. Additionally, in this example, a gas-tight syringe is used to pierce the septum and introduce gas into the high-vacuum extraction system. Other methods that control the introduction of gas into the high-vacuum extraction system (such as the use of a valve instead of a screw cap and septum or other systems as described above) are also considered.

An embodiment of the present disclosure relates to use of a hydrogen gas preservative in the sample vessel, as it is critical to limit chemical reactions within the sample vessel that change the composition of the gas mixture released from the hydrogen source rock. Biological or chemical reactions that may reduce the amount of hydrogen measured may include microbial (hydrogen degradation during sulfate reduction, or biogenic methane formation, or hydrogen respiration), abiotic methane and ammonia generation, or hydrogen reduction of minerals (such as hematite to magnetite or pyrrhotite to pyrite). Therefore, an embodiment of the present disclosure relates to the use of a gas preservative or a combination of multiple gas preservatives which are non-reactive phases that may or may not contain biocide to completely fill the remaining non-sample filled volume contained within the sample vessel. The preservative(s) and geologic material are added to the sample vessel concurrently and the sample vessel is then sealed, minimizing the potential for hydrogen to be degraded within the sample vessel in the time frame between sample collection and gas extraction and analysis. Some examples of preservatives that can be added to displace oxygen-bearing atmospheric gas from the sample vessel and minimize oxygen reactivity with sample gas include: 1) air-saturated water, 2) air-saturated water with a biocide, 3) nitrogen or other inert gas sparged air-saturated water, 4) de-oxygenated water (i.e., water that contains no dissolved oxygen that may react with present hydrogen), 5) biocide in de-oxygenated water (which inhibits hydrogen-consuming microbes from metabolizing gases in the sample vessel), and/or 6) inert gas at atmospheric pressure.

Once the sample is collected and sealed in the gas-tight vessel, fluids that were previously trapped in the geologic material, will be released from within the material (and transferred to the sample vessel where it can mix with the background fluid in the sample vessel (e.g., atmospheric gas); these fluids can be extracted by the methods described above. To introduce the sample vessel fluids into the instrument system, the septum cap is first pierced with a needle or by opening the valve. Gas tubing is attached to the back end of the needle or valve so that upon piercing the septum cap or opening the valve, the sample gas mixture of subsurface fluids and atmospheric gases originally in the chamber can be extracted from the sample vessel and introduced into the high-vacuum extraction system. In this example, the gas tubing on the back end of the needle or valve is plumbed to a vacuum line with known volume that contains a static vacuum (i.e., a closed volume such as a chamber or tubing that has been previously evacuated to less than atmospheric pressure) that is monitored for pressure (e.g., using a capacitance monometer, Penning gauge, Pirani gauge, or other pressure gauge).

After the needle pierces the septum cap or the valve is opened, the pressure differential between gas trapped in the sample vessel and the volume containing a static vacuum causes gases to continue to transfer from the interior of the geologic material to the known volume containing a static vacuum. The transfer of the headspace gas in the sample vessel into the known volume containing a static vacuum may be relatively rapid because the gas exists as free gas at relatively elevated pressure (based on prior periods of higher hydrostatic and lithostatic pressure in situ) that is then expanded into a larger volume previously evacuated to a lower pressure. Gas still contained within the interior of the geologic material may continue to transfer to the volume containing a static vacuum more slowly due to decreasing pressure gradients until pressure equilibrium is achieved. The amount of time for pressure equilibrium to be achieved depends on: 1) the volume and pressure of gas stored in the geologic material compared to the known volume and pressure of the volume containing a static vacuum; 2) the ease at which fluid may escape the geologic material (i.e., porosity, permeability, and relative permeability of the geologic material); and 3) the composition of gas species in the gas mixture of the sample fluid (e.g., helium and hydrogen may take less time to equilibrate compared to larger gas molecules such as ethane or larger hydrocarbons, $CO_2$, krypton, or xenon). Therefore, in an embodiment, the sample vessel may be exposed to a static vacuum for specified amounts of time (e.g., minutes, hours) in order to allow adequate gas transfer from the sample vessel to the high-vacuum extraction system. Further, in this embodiment, the pressure of the static vacuum may be varied to optimize the extraction process based on, for example, the porosity and permeability of the sample material (e.g., samples with low porosity and permeability may require larger pressure differentials or more time to facilitate gas extraction). Pressure differentials can be achieved by increasing the level of vacuum in the extraction line to which the sample vessel may be exposed. Vacuum intensity (i.e., progressively lower pressure) increases from rotary vane or diaphragm pumps to turbomolecular pumps to ion getter pumps, each of which can be augmented using chemical sorbents, cryogenic chambers, and other methods.

To remove liquid water, water vapor, chemical agents used to prevent hydrogen degradation (e.g., biocide), or various other chemical species, the extracted gas stream can be exposed to traps chilled to sufficiently low temperatures (e.g., −20 to −78° C.), such as a nude trap (i.e., empty metal vacuum container), a series of nude traps, a vacuum chamber filled with various high surface area sorbent materials (e.g., charcoal, carbon black, zeolites, or other molecular sieve compounds), or a series of vacuum chambers filled with various high surface area sorbent material to separate individual or multiple gas species within a gas mixture based on their mass, chemical behavior, solubility, or known phase states at differing temperature and pressure regimes (e.g., gas, liquid, solid, supercritical). After some duration (e.g., 2 to 10 minutes), the vacuum line can then be isolated from the sample vessel and the pressure is recorded on a capacitance monometer or other means of pressure measurement with a pressure range of ~1×10$^{-9}$ to 20 torr. The separation of water vapor and/or liquid water from the gas stream may be enhanced by introducing the gas stream to a gas permeable membrane (e.g., silicon diffusion membrane, fused silica capillary membrane, thin-walled Polytetrafluoroethylene (PTFE) tubing) (FIG. 8).

Following previously disclosed methods, the gas stream may be split into equivalent gas streams. Each gas stream may undergo chemical or cryogenic separation steps to remove specific gas species or water from the bulk gas stream. Specifically, each gas stream may then be exposed to a cold trap for some duration (e.g., 2 to 10 minutes). Gas stream 1 may then be exposed to a cold trap (−20 to −78° C.) to condense/freeze any remaining water vapor, while most other species (e.g., hydrogen, ammonia, helium, methane, heavier hydrocarbons, nitrogen, oxygen, argon, dihydrogen sulfide, carbon dioxide, other noble gases) remain in the gas phase. Gas stream 2 may then be exposed to a cold trap chilled to liquid nitrogen temperatures (−196° C.) to cryogenically condense/freeze any remaining water, ammonia, dihydrogen sulfide, carbon dioxide, or argon, while other gases (e.g., hydrogen, helium, neon, methane, nitrogen, argon) remain in the gas phase. Simultaneously, each gas stream is introduced to separate mass spectrometers for measurements of specific gas compounds separated by mass to charge ratio (m/z).

The methods described above may be performed using an apparatus comprising components 802-820. Gases may first flow through inlet 802, which may comprise a valve, an injection port, an automatic sample injector, or the like. Following the sample extraction, compressed air or other gases may be flown through inlet 804 and vent through a gas-tight needle in 802 to eject any septa that may become lodged during septum piercing. The apparatus includes one or more moderate cold traps 806, with temperatures ranging between −20° C. and −78° C., and one or more LN2 cold traps 808, with temperatures about −196° C. The apparatus also includes pressure detectors 810, expansion volumes 812, high-vacuum pump 814, backing pump 816 (which functions as an additional, assisting vacuum pump), gas permeable membrane 818, and mass spectrometers 820.

The processing of the raw m/z data produced by and extracted from each quadrupole mass spectrometer to generate relative gas concentration data of targeted species may be conducted by computer programming routines. The data processing, reconciliation, interference corrections, and final abundance calculations may include multiple interference corrections and/or multiple stages of interference corrections as necessary to improve or make possible the detection of certain gas species, to include hydrogen, ammonia, helium, and other key analytes relevant to evaluating hydrogen systems based on the methods of chemical separation and/or condensation/cryogenic separation used in the measurement process. This may also involve multiple stages of data reconciliation depending on the abundances of gas species within the mixture and the methods used to quantify those gas species. For example, mass spectral interferences may exist not only due to variable ionization efficiencies of different analytes but also due to overlap from multiply substituted isotopologues of individual gas species, which may be quantified separately with other techniques and instrumentation such as gas chromatography systems or isotope ratio mass spectrometers. In some embodiments, the proportion of each isotopologue in an analyte gas mixture may be used to classify the source of each constituent analyte gas as biogenic, abiogenic, or catagenic. The raw data processing and data reconciliation yields the bulk gas composition (i.e., partial pressures) of the atmospheric gas and gas derived from geologic material mixture.

An embodiment of the present disclosure relates to determining the moles of specific gas species generated and/or accumulated in a geologic material (specifically, moles of each targeted gas species on a per mass or volume of rock basis that can be released following the methods described above). An example method to achieve this final product requires first calculating the total moles of bulk gas extracted from the gas-tight sample vessel (Moles$_{total}$) by following the calculation below:

$$\text{Moles}_{total} = P_b \times (V_l + V_{rs}) \times \frac{1}{760} \times \frac{1}{22,400}$$

where $P_b$ is the pressure of the bulk gas measured in the vacuum line after extraction (in torr), $V_l$ is the volume of the vacuum line (cm$^3$), and $V_{rs}$ is the volume of remaining non-sample/preservative filled volume within the sample vessel (cm$^3$). The non-sample filled volume correction can be calculated by estimating the sample density and pairing this with the mass of the sample, which can be measured by calculating the differences between the mass of the sample vessel before and after sample collection, or estimated based on the mineralogical composition and mass of the sample (e.g., ~2 to 6 grams). Depending on the embodiments used, the $V_{rs}$ could include either atmosphere or inert gas preservative. If a liquid preservative is used (e.g., de-oxygenated water, biocide), then no remaining non-sample filled volume remains and $V_{rs}$ will be 0, 760 is the torr per 1 atmosphere of pressure (STP unit), and 22,400 is the number of cubic centimeters in 22.4 L (one mole of gas at STP). Moles of atmosphere or inert gas preservative (at 1 atm) contained within the $V_{rs}$ at time of sealing can be calculated as:

$$\text{Moles}_{rs} = \frac{V_{rs}}{22,400}$$

Next, the pressure of gas derived from the geologic material contained within the remaining non-sample filled volume of the gas-tight sample vessel ($P_{gm}$, in torr) is determined by:

$$P_{gm} = \frac{P_b \times (V_l + V_{rs})}{V_{rs}} - P_{rs}$$

where $P_{rs}$ is the pressure of the atmosphere or inert gas preservative that originally occupied all remaining non-sample filled volume immediately after sample collection. Next, $P_{gm}$ (in torr) is converted to total moles of gas released by the geologic material (Moles$_{gm}$):

$$\text{Moles}_{gm} = P_{gm} \times V_{rs} \times \frac{1}{760} \times \frac{1}{22,400}$$

To yield the moles of each gas species released from the geologic material, moles of each gas species measured in the bulk gas are calculated and the moles of gas from the remaining non-sample filled volume and not from the geologic material (e.g., from headspace atmospheric gas or inert gas, Moles$_{rs}$) are removed:

$$Moles_{analyte}=(Moles_{total} \times PP_{measured})-(Moles_{rs} \times PP_{rs})$$

where PP$_{measured}$ is the partial pressure of a specific analyte measured from the bulk gas sample, and PP$_{rs}$ is the partial pressure of a specific analyte in standard atmospheric composition or the inert gas preservative. Lastly, the Moles$_{analyte}$ is divided by the mass of rock contained within the sample vessel to evaluate the volume of past hydrogen generation and/or accumulation of hydrogen and other gas species within a mass of given source rock.

The example system presented above focuses on a single phase of extracting, detecting, and quantifying gases contained within a hydrogen source rock. However, an embodiment relates to extended extraction times and/or multiple episodes of extraction, detection, and quantification that may be used to evaluate H2$_{EV}$. Extractions may continue until no changes in pressure are measured during the extraction period, suggesting that the hydrogen source rock has been near-fully degassed of its 'mobile' gas phases. When near-fully degassed, the moles of 'mobile' hydrogen detected and quantified for each extraction step are summed to evaluate H2$_{EV}$.

Figure 10:
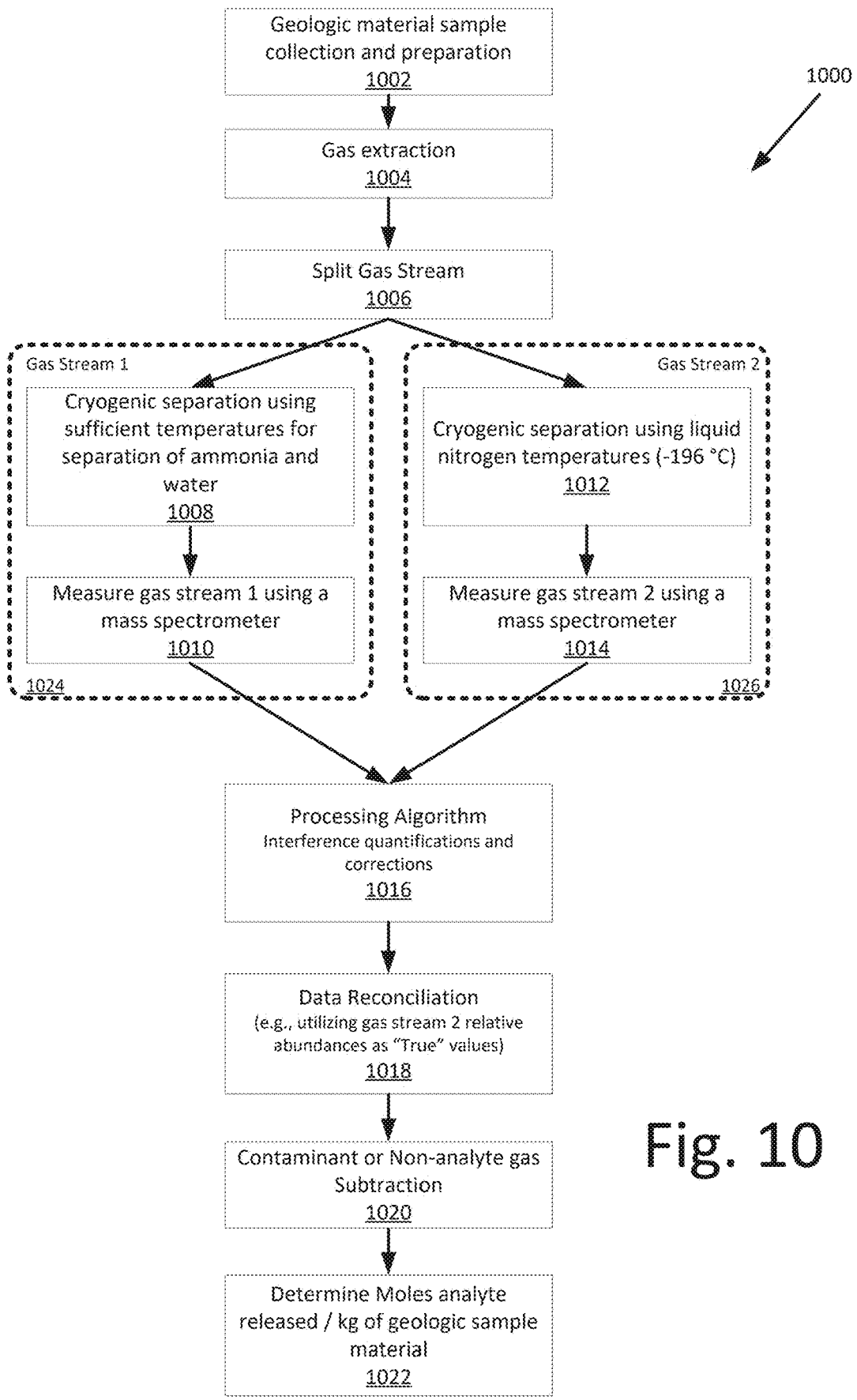
FIG. 10 is an example flow chart of a method for using the disclosed systems for the extraction, detection, and quantification of hydrogen ($H_2$), helium (He), ammonia ($NH_3$), hydrocarbon gases (e.g., $C_1$, $C_2$, $C_3$, $C_{4+}$), nitrogen ($N_2$), carbon dioxide ($CO_2$), various hydrogen-derived chemical species (e.g., dihydrogen sulfide ($H_2S$), hydrogen cyanide (HCN)), or other gases that advect or diffuse from geologic material into a gas-tight sample vessel based on pressure or concentration gradients.

Turning to FIG. 10, procedure 1000 illustrates example embodiments for extracting and analyzing analyte gases from a geologic material sample collection. Using the methods disclosed herein, the composition of gases contained in or bound to individual samples can be assessed quantitatively, allowing for the accurate determination of H2$_{EV}$.

As shown in operation 1002, the method includes collecting and preparing a geologic material sample. In some embodiments, the geological samples are collected from a borehole, a drill site, or other location of interest. In some embodiments, the geological material samples may be procured from a repository of samples which have been previously collected and stored. The sample may be prepared using any of the methods specified herein. The step of preparing the sample may comprise placing it in a gas-tight vessel with or without preservative fluids and sealed (e.g., with a septum cap or valve).

As shown in operation 1004, gas is then extracted from the geological sample. In some embodiments, samples may be used as-is for experimentation or may be processed in some way, such as by crushing, comminuting, and/or powdering. In some embodiments, mineral phases of the geological sample may be separated from one another before or after analysis. In some embodiments, samples may be subjected to one or more forms of analysis before and/or after the samples are processed or subjected to one or more additional analyses. In some embodiments, the geologic material sample is placed into an inert, gas-tight container and sealed. In some embodiments, the container may hold additional packing materials (e.g., cotton pellets). In some embodiments, the container may also contain atmospheric gases and/or gas preservatives. In some embodiments, the total volume of gas extracted may be measured.

As shown in operation 1006, the gas stream is split into two like gas streams, each including the same constituents. In the illustrated embodiment, the gas stream is split into a first gas stream 1024 and a second gas stream 1026. In some embodiments, the gas stream may be split by removing an aliquot of the total amount of gas using a syringe, vacutainer, or similar device. In some embodiments, the gas stream may be split by flowing the gas through a split-flow valve or similar device. In still further embodiments, the gas streams 1024, 1026 may be aliquoted into smaller containers for subsequent use in the remainder of the method depicted in FIG. 10.

As shown in operation 1008, sufficient temperatures for separation of ammonia and water are used for cryogenic separation. In some embodiments, cryogenic separation may be accomplished using a cold finger device, a trap submerged in cryogenic fluids, or other devices known in the art. In some embodiments, the ammonia and water are separated by condensing them within the cold trap and removed from the device at the completion of the method shown in FIG. 10.

As shown in operation 1010, gas stream 1 1024 is measured using a mass spectrometer. In some embodiments, gases may be flowed into a mass spectrometer without further separation. In some embodiments, gases may be further separated (e.g. chromatographically) prior to entering the mass spectrometer. In some embodiments, the mass spectrometer may be a quadrupole mass spectrometer. In some embodiments, the mass spectrometer may additionally include an ion trap. In some embodiments, data is collected from the mass spectrometer for determining the mass to charge ratio (m/z) of an analyte gas which can be further used to determine the species of the analyte gas, the species of the analyte gas comprising the elemental identity or isotopic identity of the analyte gas.

As shown in operation 1012, example embodiments include using liquid nitrogen temperatures for cryogenic separation. In some embodiments, liquid nitrogen temperature may refer to the boiling point of liquid nitrogen, or −196° C. In some embodiments, cryogenic separation may be accomplished using a cold finger device, a trap submerged in cryogenic fluids, or other devices known in the art. In some embodiments, gases in gas stream 2 1026 may be separated by condensing and removed from the device at the completion of the method shown in FIG. 10.

As shown in operation 1014, gas stream 2 1026 may be measured using a mass spectrometer. In some embodiments, gases may be flowed into a mass spectrometer without further separation. In some embodiments, gases may be further separated (e.g. chromatographically) prior to entering the mass spectrometer. In some embodiments, the mass spectrometer may be a quadrupole mass spectrometer. In some embodiments, the mass spectrometer may additionally include an ion trap. In some embodiments, data is collected from the mass spectrometer for determining the mass to charge ratio (m/z) of an analyte gas which can be further used to determine the species of the analyte gas, the species of the analyte gas comprising the elemental identity or isotopic identity of the analyte gas.

As shown in operation 1016, a processing algorithm is used for interference quantifications and corrections. In some embodiments, the data collected in operations 1010 and 1014 may be combined. In some embodiments, mass spectral interferences may occur due to variable ionization efficiencies of different analytes or due to overlap from multiply substituted isotopologues of individual gas species. In some embodiments, gases present in gas streams 1 1024 and 2 1026 may only be those present in or bound to the geological material sample (e.g., atmospheric gas contamination, preservative gases) and, as such, must be corrected for in the data set. In some embodiments, a processing algorithm comprises an algorithm designed to discriminate between non-analyte gasses (e.g., atmospheric gas contamination, preservative gases) and analyte gases (e.g., hydrogen, methane, carbon dioxide, dihydrogen sulfide, helium, argon).

As shown in operation 1018, example embodiments include data reconciliation. In some embodiments, data reconciliation may be performed between the processed data sets to yield the bulk composition of the gases extracted from the geological material sample. In some embodiments, the bulk composition of the gases may comprise the partial pressures of each individual constituent gas species (e.g., hydrogen, helium) of the bulk gas. In some example embodiments, gas stream 2 1026 may be used as the reference (e.g., "True") values for data reconciliation purposes.

As shown in operation 1020, the data collected over the course of operations 1002-1018, are used to subtract the contributions of contaminant or non-analyte gases. In some embodiments, atmospheric gases may have contaminated the gas sample (e.g., by being sealed in the sample container with the geologic material sample). In some embodiments, other non-analyte gases (e.g., preservatives) may have been introduced to the sample container. In some embodiments, the contribution of the atmospheric or non-analyte gases may be subtracted from the bulk gas composition to separate it from the analyte gas composition.

As shown in operation 1022, the values obtained in operation 1020 are used to determine the number of moles of analyte gas released per kg of geologic sample material. In some embodiments, determining the number of moles of analyte gas released comprises calculating the number of moles of each constituent analyte gas from the bulk analyte gas based on the determined partial pressure of each constituent analyte gas and the total volume of gases extracted from the geological sample material.

An embodiment of the present disclosure relates to the quantification of total hydrogen present ($H2_{EV}$) within a hydrogen source rock. Extraction may continue until no changes in pressure are measured during the extraction period, suggesting that the hydrogen source rock has been near-fully degassed. When near-fully degassed, the moles of hydrogen detected and quantified for each extraction step are summed to evaluate the $H2_{EV}$ based on the 'mobile' gas content. The 'mobile' $H2_{EV}$ can be compared to the expected moles of hydrogen generated in the past ($M_2$) as part of the workflow described above.

Figure 11A:
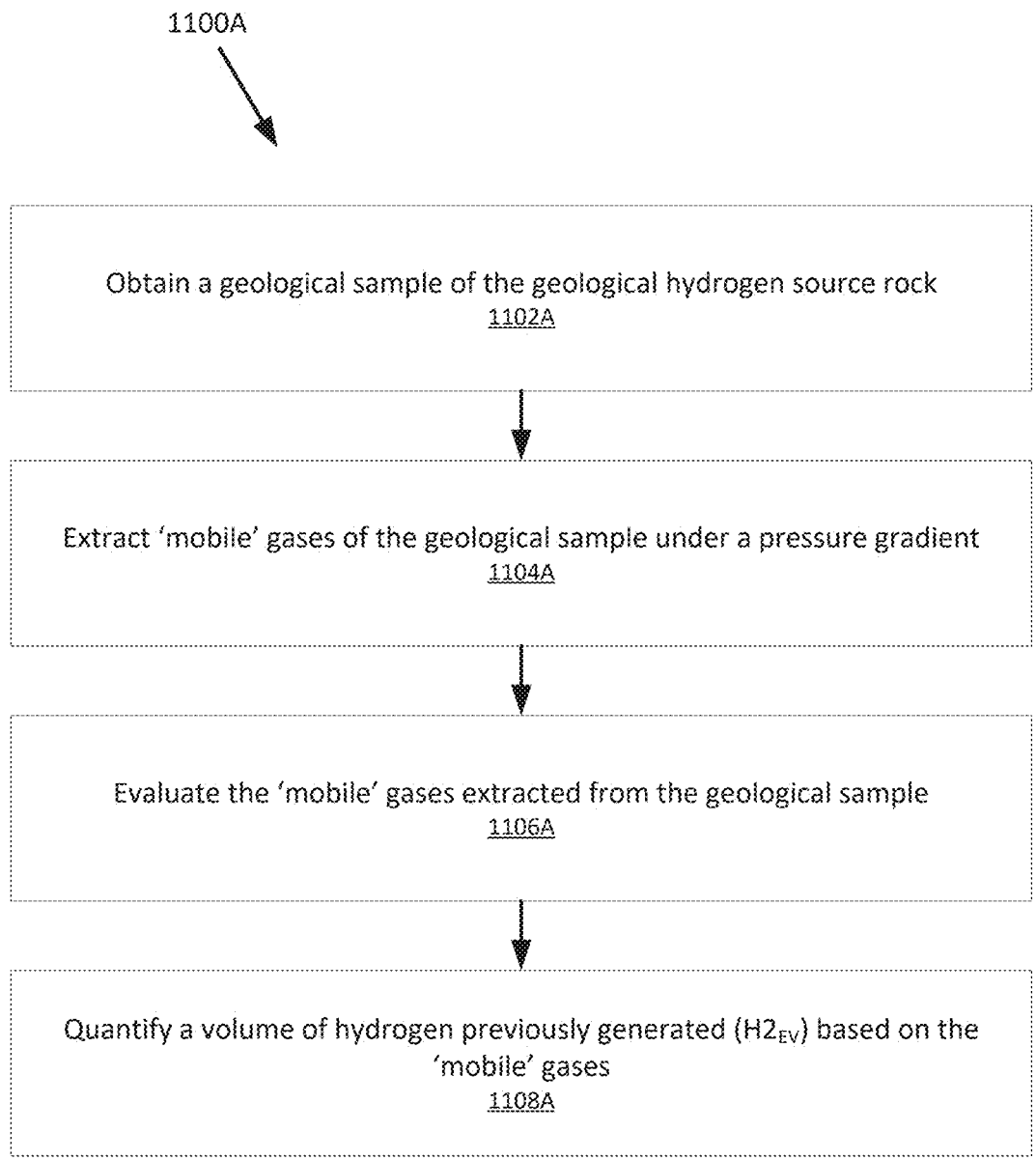
FIG. 11A shows example operations for quantifying $H2_{EV}$ of a geological source rock, in accordance with some example embodiments described herein.

Turning now to FIG. 11A, example embodiments include a method 1100A for evaluating the total existing hydrogen ($H2_{EV}$) within a geological source rock by evaluating the gas content. The methods disclosed herein allow for the determination of the identities, amounts, and compositions of gases which may be contained within or bound the surface of pores or other exposed surfaces of a geological sample. Accurately determining these qualities of gases associated with a geological sample is imperative for the task geological hydrogen exploration.

As shown in operation 1102A, the method includes using a drill, borehole, sample repository or the like to obtain a geological sample of the geological source rock. In some embodiments, the geological sample obtained could be obtained from a drilling site in the form of core samples, rock cuttings, or other standard sample varieties known in the art. In some embodiments, the geological sample obtained could be obtained from a repository of samples from known locations.

As shown in operation 1104A, the method includes using a pressure gradient to extract 'mobile' gases of the geological sample. In some example embodiments, a pressure gradient may be established by sealing the geological sample in an inert, compressible, container with a pierceable seal or valve, which may additionally contain atmospheric gases, preservatives, or other components which are not part of the analyte gases (e.g., gases contained within or bound to a geological sample), fluidly connecting (e.g., plumbing) the container to an chamber held at a lower pressure that the pressure of gases in the container, and allowing gases from the container to flow into the chamber until an equilibrium pressure is reached between the container and the chamber such that the 'mobile' gases in the container, which were associated with the geological sample, are a part of the bulk gas in the chamber. In some embodiments, geological samples may be subject to extraction of their 'mobile' gases multiple times with or without alteration of the sample. In some embodiments, 'immobile' gases (e.g., gases contained in sealed chambers of the geological sample) may be first mobilized by crushing, comminuting, powdering, or other standard methods known in the art, and then extracted from the geological sample. In some embodiments, the volume of gases extracted may be measured. In some embodiments, the container may be compressed (e.g., with a hydraulic press).

As shown in operation 1106A, the method includes using analytical methods to evaluate the 'mobile' gases extracted from the geological sample. In some embodiments, evaluating the 'mobile' gases may comprise selectively removing constituent gases from the bulk gases. In some embodiments, selectively removing constituent gases may comprise subjecting the bulk gas to cryogenic temperatures, flowing the bulk gas through a membrane, chromatographic separation, or other gas separation methods known in the art. In some embodiments, evaluating the 'mobil'e gases may comprise the use of a mass spectrometer to determine concentrations, elemental identities, isotopic identities, isotopologues, partial pressures, or other qualities of the constituent components of a mixture of gases. In some embodiments, evaluating the 'mobile' gases may comprise processing the data from mass spectrometry measurements to remove contributions from interferences, contaminations, or atmospheric components, such that the composition of the analyte gases is known, including the partial pressures of each constituent gas in the mixture of analyte gases.

As shown in operation 1108A, the data collected in operation 1106A is used to quantify a volume of hydrogen previously generated ($H2_{EV}$) based on the 'mobile' gases. In some embodiments, the volume of hydrogen previously generated ($H2_{EV}$) may be calculated based on the volume of gases extracted from the geological sample and the partial pressure of each constituent gas in the mixture of analyte gases. In some embodiments, the volume of hydrogen previously generated ($H2_{EV}$) may be quantified after multiple rounds of operations 1302-1306 have been performed on a single geological sample.

Figure 11B:
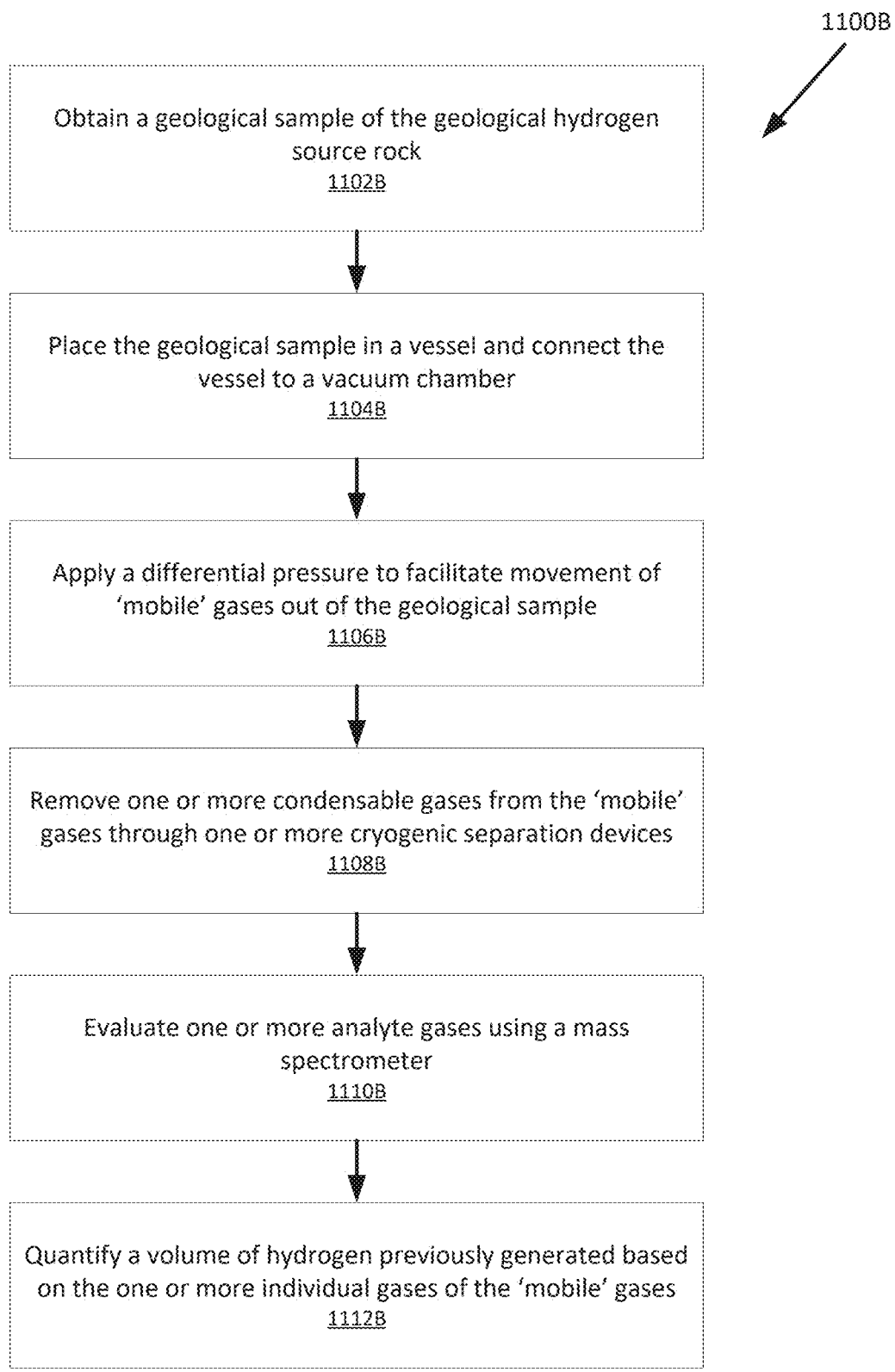
FIG. 11B shows example operations for quantifying $H2_{EV}$ of a hydrogen source rock using laboratory-based methods to evaluate the 'mobile' gas content, in accordance with some example embodiments described herein.

Looking to FIG. 11B, example embodiments are shown for extracting and analyzing analyte gases from a geologic material sample collection. Using the methods 1100B disclosed herein, the composition of gases contained in or bound to individual samples can be assessed quantitatively, allowing for the accurate determination of $H2_{EV}$ based on the 'mobile' gas content.

As shown in operation 1102B, the method includes collecting and preparing a geologic material sample. In some embodiments, the geological material samples are collected from a borehole, a drill site, or other location of interest. In some embodiments, the geological material samples may be procured from a repository of samples which have been previously collected and stored. The sample may be prepared using any of the methods specified herein. The step of preparing the sample may comprise placing it in an inert sample container with or without gas preservation fluids.

As shown in operation 1104B, the geological sample is placed in a vessel and the vessel is connected to a vacuum chamber. In some embodiments, the vessel may be sealed with a pierceable seal or other sealing component. In some embodiments, the vessel may be a container which is inert, non-reactive with hydrogen, and/or compressible. In some embodiments, the vessel may be fluidly connected to the vacuum chamber through plumbing, by piercing the seal of the vessel with a needle connected to the vacuum chamber, or by any other standard means.

As shown in operation 1106B, a differential pressure is applied to facilitate movement of 'mobile' gases out of the geological sample. In some example embodiments, a pressure gradient may be established by sealing the geological sample in an inert, container with a pierceable seal, which may additionally contain atmospheric gases, preservatives, or other components which are not part of the analyte gases (e.g., gases contained within or bound to a geological sample), fluidly connecting (e.g., plumbing) the container to a chamber held at a lower pressure that the pressure of gases in the container, and allowing gases from the container to flow into the chamber until an equilibrium pressure is reached between the container and the chamber such that the 'mobile' gases in the container, which were associated with the geological sample, are a part of the bulk gas in the chamber. In some embodiments, geological samples may be subject to extraction of their 'mobile' gases multiple times with or without alteration of the sample. In some embodiments, 'immobile' gases (e.g., gases contained in sealed chambers of the geological sample) may be first mobilized by crushing, comminuting, powdering, or other standard methods known in the art, and then extracted from the geological sample. In some embodiments, the volume of gases extracted may be measured. In some embodiments, the container may be compressed (e.g., with a hydraulic press).

As shown in operation 1108B, one or more condensable gases are removed from the 'mobile' gases through one or more cryogenic separation devices. In some embodiments, cryogenic separation may be accomplished using a cold finger device, a trap submerged in cryogenic fluids, or other devices known in the art. In some embodiments, the ammonia and water are separated by condensing and removed from the device at the completion of the method shown in FIG. 11B.

As shown in operation 1110B, one or more analyte gases are evaluated using a mass spectrometer. In some embodiments, gases may be flowed into a mass spectrometer without further separation. In some embodiments, gases may be further separated (e.g. chromatographically) prior to entering the mass spectrometer. In some embodiments, the mass spectrometer may be a quadrupole mass spectrometer. In some embodiments, the mass spectrometer may additionally include an ion trap. In some embodiments, data is collected from the mass spectrometer for determining the mass to charge ratio (m/z) of an analyte gas which can be further used to determine the species of the analyte gas, the species of the analyte gas comprising the elemental identity or isotopic identity of the analyte gas.

As shown in operation 1112B, a volume of 'mobile' hydrogen previously generated ($H2_{EV}$) is quantified based on the 'mobile' gases. In some embodiments, the volume of hydrogen previously generated ($H2_{EV}$) may be calculated based on the volume of gases extracted from the geological sample and the partial pressure of each constituent gas in the mixture of analyte gases. In some embodiments, the volume of hydrogen previously generated ($H2_{EV}$) may be quantified after multiple rounds of operations 1102B-1110B have been performed on a single geological sample.

The example system presented above focuses on measuring the pressure and gas content of a rock sample by extracting, detecting, and quantifying 'mobile' gases contained within a hydrogen source rock. An embodiment involves the use of extended extraction times and/or multiple episodes of extraction, detection, and quantification to evaluate $H2_{EV}$, the intrinsic pressure of hydrogen in the source rock, and the relative permeability of the gas species. Specifically, prolonged extraction times (e.g., 10 to 120 minutes or more) result in equilibration between the gas contained within the geologic material and the static vacuum line that approaches an asymptotic value defined herein as the pressure equilibrium asymptote. If incremental extraction stages are used where aliquots of the pressure and composition of extracted gases are analyzed at each stage. During the degassing period the pressure is continuously monitored and recorded to quantify the volume of hydrogen released over time.

An embodiment of the present disclosure relates to a quantitative model to determine the intrinsic pressure of hydrogen within the hydrogen source rock at the subsurface conditions from which it was extracted. An example quantitative model will back-calculate the in-situ pressure by regressing the pressure equilibrium asymptote measured during the prolonged extraction(s) and analyzing the porosity of the geologic source rock (through Helium Porosimetry, Nuclear Magnetic Resonance (NMR), X-ray Computed Tomography (XCT), or similar method). Pairing this in-situ pressure and porosity with the quantified gas composition yields the in-situ pressure of hydrogen (or other gas species) within the primary porosity at the subsurface conditions from which the sample was extracted.

In the present context, relative permeability relates to the ability for a given rock sample (i.e., in this case a hydrogen source rock) to allow for hydrogen (or other gas) advection in the presence of other geologic fluids (i.e., other gases, water, brine, oil). Explicitly, relative permeability varies based on rock properties (e.g., porosity, permeability, pore throat size, fracture intensity and characteristics), the degree of water saturation, and the gas composition. An embodiment of the present disclosure relates to a quantitative model to determine the in-situ relative permeability of hydrogen within a hydrogen source rock by evaluating the rate of hydrogen release per unit time and specifically the slope of moles of gas released per unit time, which can be used then to back calculate the rate of hydrogen advection through a given rock sample by fitting equations of Darcy's Law and/or other fluid flow equations.

In an example of the quantitative model, the first step is to pair the measured gas compositions with the pressures recorded during the extraction stage(s) to calculate the rate of degassing for each analyte of interest. In this embodiment, this may be achieved by conducting multiple pressure and gas compositional analyses during an extended gas extraction period, where the concentrations of gases of interest (e.g., hydrogen, helium, nitrogen, $CO_2$, methane) are measured at stages and the change in individual species concentrations are monitored over time. While the pressure of the overall sample may drop as you perform multiple analyses of the same fluid, the concentrations of individual gas species will change as the individual gas species equilibrate with the static vacuum pressure at different rates. During the degassing phase, the individual gas species within the gas mixture will elute (i.e., advect or diffuse out of the sample) at different rates (i.e., with a different slope of moles released per unit time) and reach an asymptotic value at different times based on the rate of the gas species' transport from the geologic material to the sample chamber. The relative permeability of the hydrogen source rock at the conditions from which it was extracted can then be calculated by regressing the rate of degassing back to the in-situ conditions.

Crushing Extraction Methods to Estimate $H2_{EV}$ in Source Rocks

In unaltered samples, the 'mobile' gases slowly advect and diffuse out of sample materials over time. By augmenting the porosity and permeability of a given rock sample, the rate of gas release can be greatly enhanced. For example, if the geologic material is physically altered (i.e., pulverized through crushing), the 'mobile' gas phases will be released nearly instantaneously from the sample at rates greatly exceeding those expected through the otherwise unaltered natural pore throats and fractures. Similarly, the 'immobile' gases previously trapped in isolated pore spaces or fluid inclusions within geologic material can be rapidly released and then analyzed using mass spectrometry methods. Disintegration of geologic material can be achieved using a ball mill, shatter box, laser ablation system, drill, auger, or crushing by a manual, hydraulic, or other form of press. The example within the present embodiment is related to the latter. The present disclosure relates to additional novel systems and methods developed in order to quantify the existing volumes of hydrogen (i.e., $H2_{EV}$) that are present within a given sample of hydrogen source rock.

The present embodiment discloses a sample collection and analytical method to extract, detect, and quantify existing volumes of hydrogen ($H_2$), helium (He), ammonia ($NH_3$), various hydrogen-derived chemical species (e.g., dihydrogen sulfide ($H_2S$), hydrogen cyanide (HCN)), hydrocarbon gases (i.e., $C_1$, $C_2$, $C_3$, $C_4+$), nitrogen ($N_2$), carbon dioxide ($CO_2$), other noble gases, or other gases that are released from crushed geologic material within a gas-tight sample vessel (FIGS. 11A and 11B).

An embodiment of the present disclosure involves the use of known volumes of geologic sample material that are then placed into gas-tight sample vessels with a known volume. The geologic material may be collected as wet or dry material. The absolute volume of sample may change depending on the size of the sample vessel used but known volumes of both allow important parameters (e.g., atmospheric contamination, intrinsic pressure) to be accurately quantified. If the geologic material is wet (i.e., water, water-based mud, oil-based mud), such as drill cuttings collected quickly after drilling (e.g., at the possum belly while drilling a well or borehole), the material may first be dried completely or partially.

When collecting freshly exposed samples (e.g., drill cuttings collected during drilling), sealing the sample in a gas-tight sample vessel should occur rapidly after sample collection, as existing 'mobile' gas phases will actively degas from the hydrogen source rock and/or start to oxidize by interactions with oxygen in the atmosphere from the time the materials are broken away from the lithologic formations during drilling and while being transported up the borehole to the surface. The pulverization of samples rapidly collected and sealed after liberation from the hydrogen source formation (e.g., drill cuttings collected at the possum belly) provide the best estimates of $H2_{EV}$, as both 'mobile' and 'immobile' gases are captured and can be extracted from the gas-tight sample vessel. Specifically, the 'mobile' gases that are escaping the geologic material are contained within the gas-tight sample vessel and are readily extractable. 'Immobile' gases are liberated through the pulverization of the sample. Therefore, the gas extracted from rapidly collected and sealed samples that are then pulverized will be a mixture of both the 'mobile' and 'immobile' gases. The relative proportions of the 'mobile' and 'immobile' gas phases can be distinguished by comparing gas released over time from a non-physically altered sample to that released from crushed residual material or by evaluating the freshly crushed sample, allowing it to degas and measuring the residual gas component.

In comparison, in an embodiment, archived drill cuttings, core, or other geological material collected from historical wells, or samples collected at or near the surface, may also be used as samples to identify existing hydrogen source rocks or identify active hydrogen systems by quantifying hydrogen that has been adequately trapped in geologic materials at near atmospheric pressure for extended periods of time. Depending on a variety of factors (e.g., lithology, porosity, permeability, total fluid content, fluid composition, time elapsed since collection, etc.), these samples will have lost varying degrees of their 'mobile' gas content prior to analysis. However, sample pulverization induces new fractures through potentially previously isolated volumes within the geologic material (e.g., pore spaces, fluid inclusions), which may release existing volumes of 'immobile' gas. Detection and quantification of the 'immobile' gas species of archived drilled cuttings or samples of geologic material collected at or near the surface can be used to identify active hydrogen source rocks (i.e., without drilling a well or borehole) as well as evaluate the degree of 'immobile' gas contained within isolated volumes (e.g., pore space, fluid inclusions). Verification of active hydrogen systems can be an important part of derisking hydrogen systems and enabling natural hydrogen exploration.

In this embodiment, samples may be of potential hydrogen source rocks or geologic materials targeted for possible conventional hydrogen system formations (e.g., reservoirs or seals) to identify active hydrogen systems. For example, hydrogen measured in samples from sedimentary formations that overlie potential hydrogen source rocks may provide information relating to hydrogen generation (i.e., hydrogen has been generated by some hydrogen source rock in the geologic past), migration (i.e., inflow of hydrogen into the sedimentary formation(s) in which the hydrogen was measured), or accumulation/seal, which depends on the tightness of the geologic material as to whether hydrogen will remain trapped for periods of time after the material is removed from the subsurface.

An embodiment of the present disclosure relates to using copper tubing as the sample vessel for the geologic material. Copper is a malleable, easily manipulated but relatively impermeable metal, that allows for compression without puncturing or fracturing which would eliminate the gas-tight integrity of the sample vessel. Prior to sample collection, a length of copper tubing (e.g., ⅜" OD refrigeration grade copper tubing) is cut (e.g., ~5" long) and plugged at one end with a gas-tight fitting (e.g., Swagelok® compression fitting plug). The mass of the geologic material is recorded, and the sample is placed within the tube (e.g., FIG. 13A).

Figure 12:
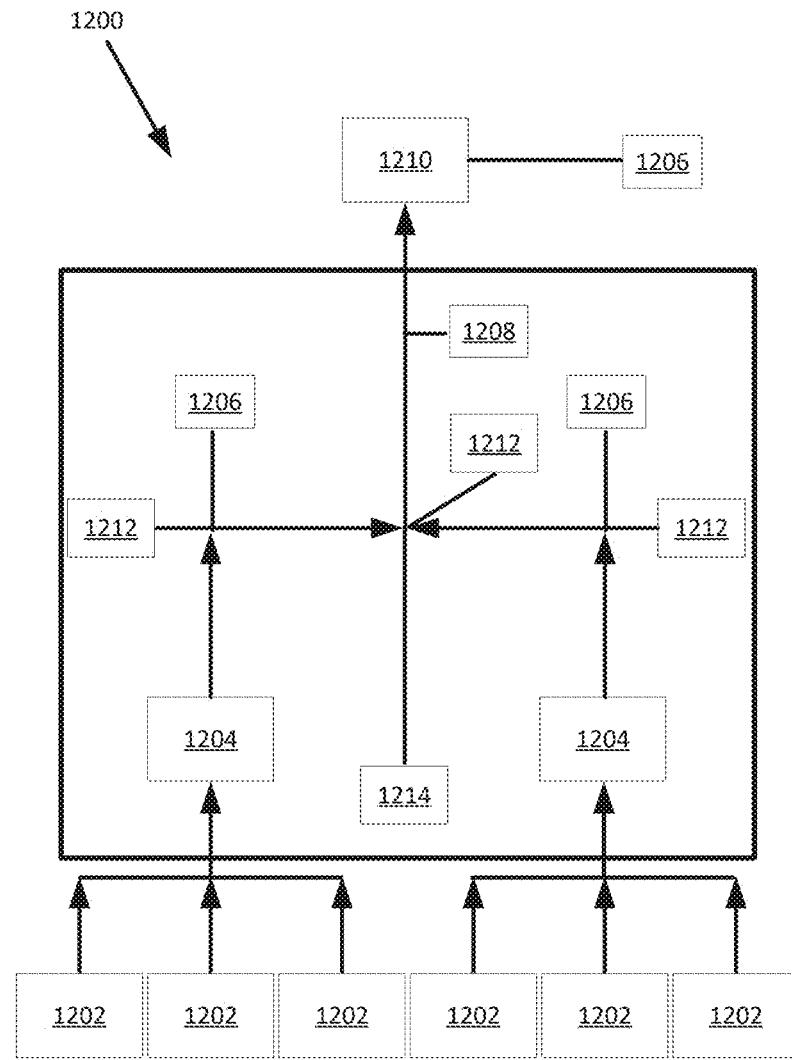
FIG. 12 is an annotated schematic of an example sample extraction and analytical system used to extract and detect hydrogen ($H_2$), helium (He), ammonia ($NH_3$), hydrocarbon gases (e.g., $C_1$, $C_2$, $C_3$, $C_{4+}$), nitrogen ($N_2$), carbon dioxide ($CO_2$), various hydrogen-derived chemical species (e.g., dihydrogen sulfide ($H_2S$), hydrogen cyanide (HCN)), or other gases that are trapped in pore spaces and fluid inclusions (termed 'immobile' gases) of geologic material (e.g., whole core, sidewall core, drill cuttings) and released from the geologic materials into the gas-tight sample vessel based on advection or diffusion from existing pressure or concentration gradients or by crushing the geologic material.

FIG. 12 is an annotated schematic of an apparatus 1200, which is a sample extraction and analytical system designed to extract and detect gas species from geologic material contained within sealed sample vessel 1202 (e.g., gas-tight copper tube vessel). Apparatus 1200 further comprises cold traps 1204, vacuum pumps 1206, bleed valve 1208, mass spectrometer 1210, pressure detectors 1212 and expansion volumes 1214.

Figure 13A:
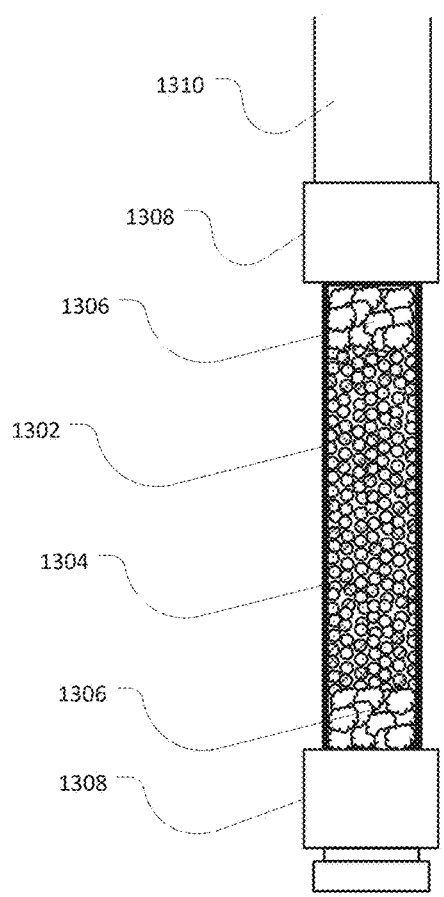
FIGS. 13A and 13B are annotated schematics of a sample extraction system designed to extract gas from geologic material using a gas-tight vessel.
Figure 13B:
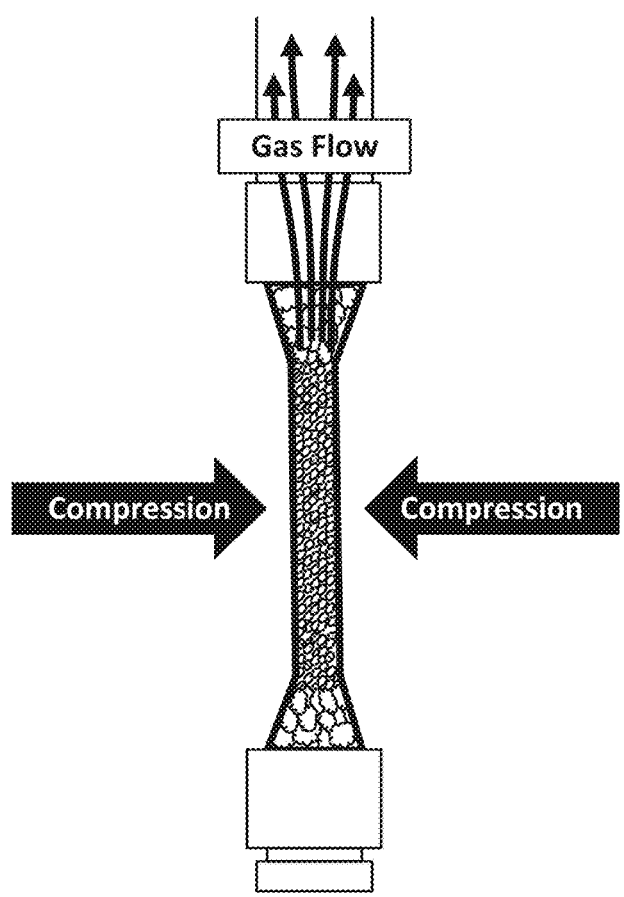

FIG. 13A displays a sealed sample vessel 1302 prepared for gas extraction and FIG. 13B shows the gas extraction process, where the portion of the sealed sample vessel 1302 containing the geologic material 1304 is compressed with a hydraulic press, crushing the sample and enhancing the rate for releasing gases contained within the pore space or fluid inclusions. The sealed sample vessel 1302 may also comprise additional packing materials 1306 (e.g., cotton pellets), and compression fittings 1308. The sealed sample vessel 1302 may be plumbed to a vacuum system experimental apparatus via connector 1310.

Hydrogen can be a labile/reactive chemical in the subsurface and is especially reactive when exposed to atmospheric conditions at the surface. For example, hydrogen is unstable and rapidly oxidized when in the presence of free oxygen (FIG. 6). Therefore, it is critical to limit chemical reactions within the sample vessel that change the composition of the gas mixture released from the hydrogen source rock. An embodiment of the present disclosure relates to the use of a gas preservative or a combination of multiple gas preservatives to completely fill the remaining non-sample filled volume contained within the sample vessel. The preservative(s) and geologic material are added to the sample vessel concurrently and the sample vessel is sealed, ensuring that limited volumes of hydrogen were degraded within the sample vessel in the time frame between sample collection and gas extraction. Some examples of preservatives that can be added to water to displace oxygen-bearing atmospheric gas from the sample vessel include: 1) air-saturated water, 2) de-oxygenated air-saturated water (which also has no dissolved oxygen that may react with present hydrogen), 3) biocide added to de-oxygenated water (which inhibits hydrogen-consuming microbes from populating the sample vessel), and/or 4) inert gas.

An embodiment of the present disclosure relates to the method to extract and detect existing volumes of gas released from crushed hydrogen source rock. The top of the sample vessel is attached to the vacuum line using a gas-tight fitting (e.g., Swagelok® compression fitting nut and ferrule), creating a gas-tight seal. The hydrogen source rock is then pulverized (e.g., using a hydraulic, manual, electronic or other press, ball mill, or other crushing device), releasing any existing volumes of gas contained within the hydrogen source rock. The gas is expanded into a static vacuum (previously evacuated) line and exposed to a cold trap (e.g., nude U-trap) chilled to sufficiently low temperatures (−78 to −20° C.) for some duration of time (e.g., 2 to 10 minutes) to condense/freeze water vapor, while most other gas species (e.g., hydrogen, ammonia, helium, methane, heavier hydrocarbons, nitrogen, oxygen, argon, dihydrogen sulfide, carbon dioxide, other noble gases) remain in the gas phase. The dehydrated gas stream is then introduced to the quadrupole mass spectrometer, where m/z measurements are made and recorded.

An embodiment of the present disclosure relates to processing the raw m/z data produced by and extracted from each quadrupole mass spectrometer to generate relative gas concentration data of targeted species. The computer programming routines are used in analyses such as data processing, reconciliation, interference corrections, and final abundance calculations may include multiple interference corrections and/or multiple stages of interference corrections as necessary to improve or make possible the detection of certain gas species, to include ammonia, based on the methods of chemical separation and/or condensation/cryogenic separation used in the measurement process. Data processing methods presented above are used to remove the atmospheric or inert gas preservative from the gas sourced from the geologic material, and to calculate the moles of hydrogen per unit volume or mass of hydrogen source rock (FIG. 10).

In some embodiments, once the 'mobile' gases have been extracted from the geologic material, the 'immobile' gases (e.g., gases contained within sealed volumes of the geologic material) may then be mobilized by crushing, comminuting, powdering, or other standard methods known in the art, and then extracted from the geological sample. In some embodiments, the 'immobile' gases are extracted from the same geologic material that had already undergone 'mobile' gas extraction and detection. In some embodiments, the 'immobile' gases are extracted from geologic material that has not previously had the 'mobile' gases extracted and detected. In some embodiments, the volume of gases extracted may be measured. In some embodiments, the container may be compressed (e.g., with a hydraulic press).

Figure 14:
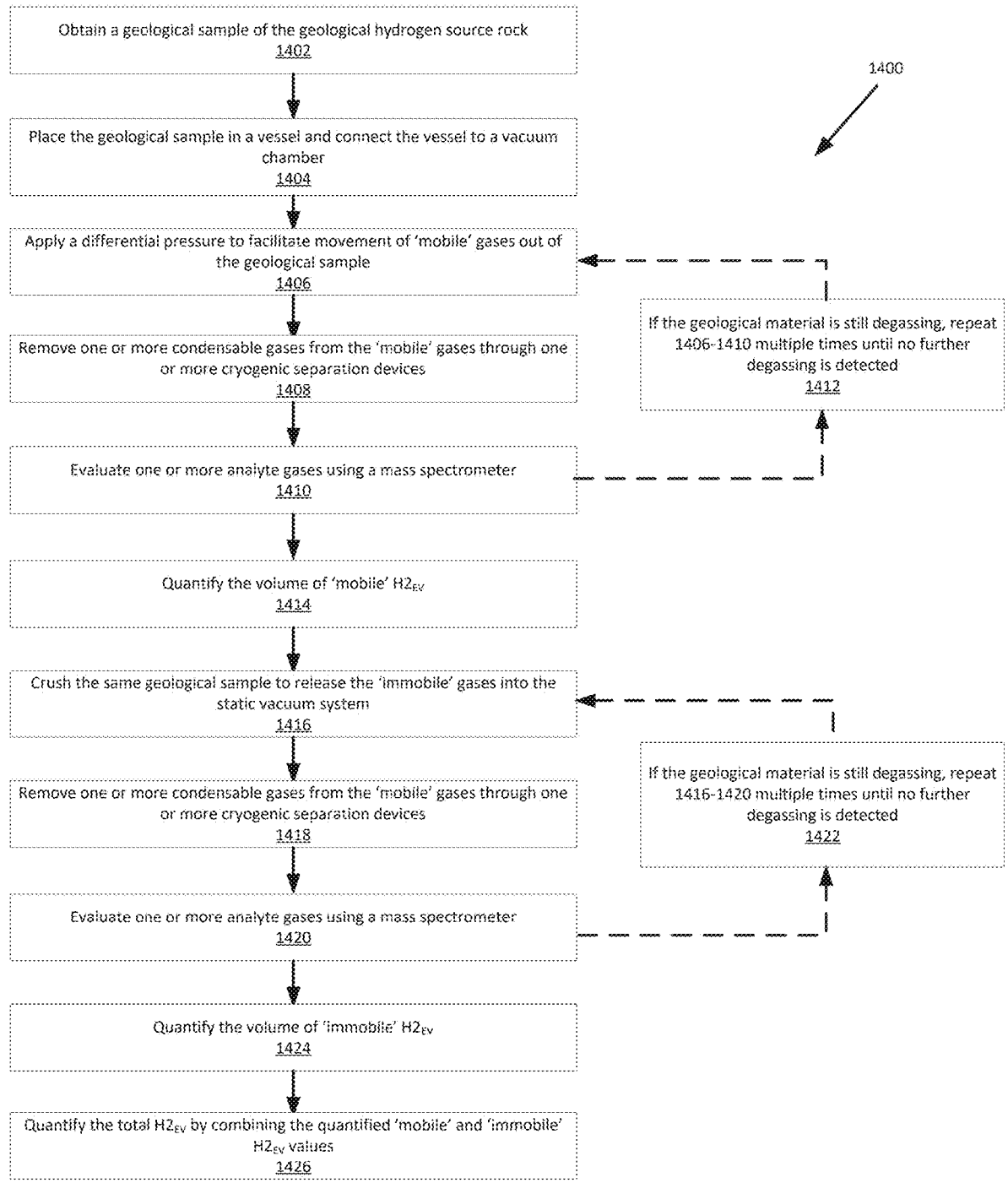
FIG. 14 shows an example flowchart for quantifying the $H2_{EV}$ of a hydrogen source rock using laboratory-based methods that evaluate and sum both the 'mobile' and 'immobile' gas content, in accordance with some example embodiments described herein.

Looking to FIG. 14, procedure 1400 illustrates example operations for extracting and analyzing both 'mobile' and 'immobile' gases from the same geological material sample. Using the methods disclosed herein, the composition of both 'mobile' and 'immobile' gases contained in or bound to individual samples can be assessed quantitatively, allowing for the accurate determination of $H2_{EV}$.

As shown in operation 1402, the method includes collecting and preparing a geologic material sample. In some embodiments, the geological material samples are collected from a borehole, a drill site, or other location of interest. In some embodiments, the geological material samples may be procured from a repository of samples which have been previously collected and stored. The sample may be prepared using any of the methods specified herein. The step of preparing the sample may comprise placing it in an inert, malleable, sample container with or without gas preservative fluids.

As shown in operation 1404, the geological sample is placed in a vessel and the vessel is connected to a vacuum chamber. In some embodiments, the vessel may be sealed with a pierceable seal or other sealing component. In some embodiments, the vessel may be a container which is inert, non-reactive with hydrogen, and/or compressible. In some embodiments, the vessel may be fluidly connected to the vacuum chamber through plumbing, by piercing the seal of the vessel with a needle connected to the vacuum chamber, or by any other standard means.

As shown in operation 1406, a differential pressure is applied to facilitate movement of 'mobile' gases out of the geological sample. In some example embodiments, a pressure gradient may be established by sealing the geological sample in an inert, compressible, container with a pierceable seal, which may additionally contain atmospheric gases, preservatives, or other components which are not part of the analyte gases (e.g., gases contained within or bound to a geological sample), fluidly connecting (e.g., plumbing) the container to an chamber held at a lower pressure that the pressure of gases in the container, and allowing gases from the container to flow into the chamber until an equilibrium pressure is reached between the container and the chamber such that the 'mobile' gases in the container, which were associated with the geological sample, are a part of the bulk gas in the chamber. In some embodiments, geological samples may be subject to extraction of their 'mobile' gases multiple times with or without alteration of the sample.

As shown in operation 1408, one or more condensable gases are removed from the 'mobile' gases through one or more cryogenic separation devices. In some embodiments, cryogenic separation may be accomplished using a cold finger device, a trap submerged in cryogenic fluids, or other devices known in the art. In some embodiments, the ammonia and water are separated by condensing and removed from the device at the completion of the method shown in FIG. 14.

As shown in operation 1410, one or more analyte gases are evaluated using a mass spectrometer. In some embodiments, gases may be flowed into a mass spectrometer without further separation. In some embodiments, gases may be further separated (e.g., chromatographically) prior to entering the mass spectrometer. In some embodiments, the mass spectrometer may be a quadrupole mass spectrometer. In some embodiments, the mass spectrometer may additionally include an ion trap. In some embodiments, data is collected from the mass spectrometer for determining the mass to charge ratio (m/z) of an analyte gas which can be further used to determine the species of the analyte gas, the species of the analyte gas comprising the elemental identity or isotopic identity of the analyte gas.

As shown in operation 1412, the geological sample may be subject to extraction of their 'mobile' gases multiple times. In some embodiments, the geologic material may be subject to extraction and detection of their 'mobile' gases repeatedly until no further degassing is detected, signifying that the 'mobile' gases have been fully extracted.

As shown in operation 1414, a volume of 'mobile' hydrogen previously generated ($H2_{EV}$) is quantified based on the 'mobile' gases extracted from the geologic material. In some embodiments, the volume of 'mobile' hydrogen previously generated ($H2_{EV}$) may be calculated based on the volume of gases extracted from the geological sample and the partial pressure of each constituent gas in the mixture of analyte gases. In some embodiments, the volume of 'mobile' hydrogen previously generated ($H2_{EV}$) may be quantified after multiple rounds of operations 1406-1410 have been performed on a single geological sample.

In some embodiments and shown in operation 1416, once the 'mobile' gases have been fully extracted from the geological sample, the 'immobile' gases (e.g., gases contained in sealed volumes of the geological sample) may then be released from the geological sample by crushing, comminuting, powdering, or other standard methods known in the art, and then extracted to the static vacuum system. In some embodiments, the volume of gases extracted may be measured. In some embodiments, the container may be compressed (e.g., with a hydraulic press).

As shown in operation 1418, one or more condensable gases are removed from the 'immobile' gases through one or more cryogenic separation devices. In some embodiments, cryogenic separation may be accomplished using a cold finger device, a trap submerged in cryogenic fluids, or other devices known in the art. In some embodiments, the ammonia and water are separated by condensing and removed from the device at the completion of the method shown in FIG. 14.

As shown in operation 1420, one or more analyte gases are evaluated using a mass spectrometer. In some embodiments, gases may be flowed into a mass spectrometer without further separation. In some embodiments, gases may be further separated (e.g., chromatographically) prior to entering the mass spectrometer. In some embodiments, the mass spectrometer may be a quadrupole mass spectrometer. In some embodiments, the mass spectrometer may additionally include an ion trap. In some embodiments, data is collected from the mass spectrometer for determining the mass to charge ratio (m/z) of an analyte gas which can be further used to determine the species of the analyte gas, the species of the analyte gas comprising the elemental identity or isotopic identity of the analyte gas.

As shown in operation 1422, the geological sample may be subject to extraction of their 'immobile' gases multiple times. In some embodiments, the geologic sample may be subject to extraction and detection of their 'immobile' gases repeatedly until no further degassing is detected, signifying that the 'mobile' gases have been fully extracted.

As shown in operation 1424, a volume of 'immobile' hydrogen previously generated ($H2_{EV}$) is quantified based on the 'immobile' gases. In some embodiments, the volume of 'immobile' hydrogen previously generated ($H2_{EV}$) may be calculated based on the volume of gases extracted from the geological sample and the partial pressure of each constituent gas in the mixture of analyte gases. In some embodiments, the volume of 'immobile' hydrogen previously generated ($H2_{EV}$) may be quantified after multiple rounds of operations 1416-1420 have been performed on a single geological sample.

As shown in operation 1426, the 'mobile' and 'immobile' $H2_{EV}$ values may be combined to yield the $H2_{EV}$. In some embodiments, the 'mobile' and 'immobile' $H2_{EV}$ values may be compared to evaluate the primary porosity and permeability of the hydrogen source rock. For example, tight geologic formations with low porosity and low permeability (such as a sealing structure within the geological material) may show elevated 'immobile' $H2_{EV}$ and depleted 'mobile' $H2_{EV}$ values.

Laboratory Methods to Estimate the Remaining Potential Volume of Hydrogen ($H2_{RPV}$) in Source Rocks An embodiment relates to evaluating source rock for remaining hydrogen generating potential through carefully controlled laboratory experiments followed by analyses of secondary mineral formation, the evolving chemistry of associated fluids, the volume of gas generated during alteration reactions, and other parameters. In this embodiment, in order to compare the hydrogen gas generated measured through laboratory methodologies with the predicted hydrogen generation potential, the mineralogy, elemental composition, effective surface area, and iron oxidation states of geologic sample material may be measured prior to the laboratory experiments and upon completion of the laboratory experiments, in addition to measurement and quantification of gaseous and liquid reactants and products. Alternatively, in this embodiment, analytical outputs from measurements of the reacted geological sample material (i.e., after completion of the laboratory experiments) may be compared to analyses of fresh unreacted geological sample material from the same bulk source geological sample material. This embodiment may use crushed geological sample material or whole rock samples (e.g., drill cuttings, core) for the laboratory experiments.

In this embodiment, the geological sample material is analyzed before and after the laboratory experiments to measure constituents and properties such as: modal mineralogy (XRD or similar), bulk elemental composition (XRF or similar), magnetic susceptibility, iron oxidation state (Mössbauer spectroscopy or similar), specific surface area (gas adsorption BET or similar), Fe—Mg—Ca solid solution properties, mineral textural properties, and evidence of primary mineral dissolution and secondary mineral formation (SEM-EDS).

In an embodiment, the laboratory measurements may involve optimized reaction conditions (e.g., temperature, pressure, formation fluid chemistry) and yield results which may be used to provide a maximum hydrogen generation potential ($H2_{RPV}$) of the hydrogen source rock.

This embodiment involves the preparation of synthetic idealized fluid to maximize hydrogen generation rates and efficiency in that source rock. The chemistry of the reaction chamber water may vary by pH, Eh, ion concentration, minor and trace element concentration, gas concentration, organic constituent concentration, or other factors. Dissolved oxygen concentration (i.e., oxygen fugacity) may be decreased prior to experimentation by purging ultra-high purity inert gas (e.g., nitrogen) through the water for up to 20 minutes, which reduces the oxygen fugacity content to negligible levels (i.e., 0.01 mmol/L $O_2$(aq)).

This embodiment may also involve exposing geologic materials to one or more periods of set temperature (e.g., 20 to 500° C.) or pressure conditions (e.g., 15 to 15,000 psi) to maximize hydrogen generation rates and efficiency in that source rock. The process may involve holding the pressure or temperature conditions for set periods of time including minutes, hours, or days.

An embodiment may instead involve laboratory measurements that use in-situ temperature, pressure, or formation fluid chemistry conditions by matching those with the geologic province in which the hydrogen source rock exists. These processes may involve using present temperature or pressure conditions (e.g., by using depth data, bottom hole temperature data, or geothermal gradient data). In this embodiment, analyses that utilize current pressure or temperature conditions, or formation fluid chemistry, may be used to quantify how much hydrogen a source rock may generate in its current state. Alternatively, in this embodiment, elevated pressure or temperature conditions may be used in laboratory measurements to identify the ideal reaction conditions for a specific hydrogen source rock. In so doing, exploration workflows can be developed in order to identify similar hydrogen source rocks (e.g., using airborne magnetic techniques and looking for lithologies of similar magnetic susceptibility) within a given geologic province that may exist in more favorable geologic conditions for hydrogen generation (i.e., within more ideal temperature or pressure windows); these measurements can be used to develop estimates of hydrogen generation in alternative areas.

In one embodiment, the fluids used as reactants during the laboratory experiments may be collected during drilling or during a drill stem test (DST), flow test, production test, or other test meant to test specific intervals in the subsurface, or from a producing well, monitoring well, groundwater well, geothermal well, or other well that may produce liquids, measured directly from wireline logging, or measurement while drilling (MWD) tools, or estimated based on available regional subsurface data and geologic history. Alternatively, in this embodiment, the laboratory experiments may use synthetic fluids (e.g., pH, salinity, ion chemistry, gas mixtures) that are representative of the natural fluids that exist in or around the hydrogen source rock formation in its geologic environment. For example, this may include the use of regional groundwater datasets, or pore fluid chemistries from existing wells or boreholes, as frameworks for the synthetic fluid compositions.

An embodiment includes exposing geologic materials to one or more periods of set temperature (e.g., 20 to 500° C.) or pressure conditions (e.g., 15 to 15,000 psi), or multiple stages of temperature or pressure conditions where pressure or temperature, or both, are stepwise increased or decreased. The experiments may involve holding the pressure or temperature conditions for set periods of time that span minutes, hours, days, or months. This embodiment may involve multiple stages of increased or decreased temperature or pressure. In so doing, the differing temperature or pressure conditions may represent changes in the geologic environment within which the hydrogen source rock existed through its evolutionary history. For example, this embodiment may be used to simulate the decrease in temperature associated with the cooling of a magmatic body. As another example, this embodiment may be used to simulate the increase in temperature or pressure related to increased burial in the subsurface, or alternatively, simulate decreasing temperature due to erosion and denudation of material that may have been overlying the hydrogen source rock at some time in the geologic past.

In this embodiment, laboratory experiments may use synthetic formation fluid chemistries representative of the conditions that hydrogen source rock had been subjected to at some time in the geologic past. In this manner, the temperature or pressure conditions or fluid chemistry used during the laboratory experiments may represent in situ conditions in the geologic past, which may be used to quantify the rate of hydrogen generation and the volume of hydrogen that may have been generated by specific source rocks during specific periods in the geologic past. By way of example, the physical and geochemical parameters synthesized within the reaction chamber to represent the in-situ conditions are temperature (20 to 500° C.), pressure (15 to 15,000 psi), water chemistry conditions (e.g., pH, oxygen fugacity, dissolved solute composition), reactive surface area, water/rock ratio, and concentrations of other key reactants such as major salts (e.g., calcium, magnesium, chloride, sulfate) or gases (e.g., nitrogen, carbon dioxide, methane). The methods of evaluating remaining hydrogen generation potential in source rocks are outlined in FIG. 15.

In an embodiment, the sample chamber used for the reactions is gas-tight, inert with respect to hydrogen generation (i.e., cannot contain $Fe^{2+}$, $Fe^0$, or other oxidizable elements under experimental conditions), and is able to withstand the elevated temperature and pressure conditions of the experiment. Appropriate sample chamber materials include gold, titanium, Polytetrafluoroethylene (PTFE), or others.

An example embodiment of a method of completing a laboratory experiment relates to the method of loading the geologic sample material and reactants into the experimental chamber. The source rock may be ground to a powder using a mortar and pestle, automatic mill, or similar apparatus. This finely ground material is homogenized, and grains are physically separated according to their size using multiple sieves of gradually decreasing mesh sizes. During the sieving process, a portion of the rock sample corresponding to the desirable experimental grain size is withheld, while finer material is discarded, and larger material is ground again to obtain the target grain size. An alternative method is also considered where the source rock is not ground to a powder prior to performing the laboratory experiments. The prepared experimental geologic sample material and fluid are added to the experimental chamber at representative water/rock ratios. The chamber containing the rock-water slurry is closed off from the atmosphere and frozen using a cryogenic liquid. After freezing, the chamber is opened to a vacuum line and the headspace atmosphere is evacuated from the chamber. Once sufficiently evacuated (pressure of less than 0.001 torr), the chamber is isolated from the vacuum pump, creating a static vacuum. Gas mixtures representative of the formation pore fluids (e.g., mixtures of hydrogen, carbon dioxide, methane, nitrogen) are introduced to the chamber and fill the headspace at a pressure representative of the hydrogen source rock formation (e.g., 15 to 15,000 psi).

An example embodiment of a method of completing a laboratory experiment relates to the temperature and duration of heating for the experimental chamber. Upon preparing and loading the geologic sample material and reactants into the experimental chamber, the chamber may be heated (e.g., 20 to 500° C. or higher) using a band heater, heating jacket, laser, oven, or other heating devices. The experiment is then allowed to react for an extended period of time (e.g., 1 hour to 30+ days) to quantify changes in mineralogy, gas generation, and water chemistry as the serpentinization reaction and other reactions progress. At the end of the experiment, the chamber is removed from heat and allowed to cool to ambient temperature. An example embodiment relates to numerous identical reactions terminated and analyzed sequentially after some time duration (e.g., daily, biweekly) to calculate changes in kinetic rates through time.

An embodiment relates to the system and methods to extract, detect, and quantify gases contained within the reaction chamber. The chamber is attached to a vacuum line, and a small aliquot of gas is expanded into a static (previously evacuated) vacuum line. The gas stream is exposed to one or multiple cold traps at various temperatures (−196 to −20° C.) and is then analyzed for m/z values using a mass spectrometer residual gas analyzer and processed by computational algorithms to quantify the partial pressure of hydrogen and other relevant gas species. The partial pressure of hydrogen is then converted to total moles using the equations presented above. Aqueous gas concentrations can also be calculated through the combination of the measured gas composition and gas solubility in aqueous solutions equations.

An embodiment involves the methods of quantifying non-gaseous reactants and products following the completion of a laboratory experiment. Following gas analysis, the chamber is opened, and the water is collected and filtered (e.g., using etched membrane filter, 0.2 or 0.4 m) for analysis of major ions (ion chromatography, ICP-OES), minor and trace elements (ICP-OES, ICP-MS), organic compound concentrations (ion chromatography, HPLC, GC-MS), etc. Water may also be sampled directly from the pressurized chamber through a valve connected to a dip tube under the water level and immediately acidified to pH<2 to preserve crucial elements (e.g., iron). Post-experimental rock material is removed from the experimental chamber, gently rinsed with deionized water to remove salt precipitation from experimental fluid, and dried. Mineralogical, chemical, and physical assessments may then be performed, including evaluation of the modal mineralogy (XRD, SEM-EDS or similar), chemical composition (XRF, LA-ICP-MS or similar), magnetic susceptibility, effective surface area (gas adsorption BET or similar), textural analysis (SEM-EDS or similar), or iron oxidation state (Mössbauer spectroscopy or similar).

An embodiment relates to determining the rate of hydrogen generation (moles of hydrogen/unit volume or mass rock/unit time) and $H2_{RPV}$, which can be determined through a series of identical experiments, each of which was terminated after progressively longer durations (e.g., daily, weekly, biweekly). The results also enable an evaluation of the thermodynamic state of the system (water-rock-gas equilibrium), reaction kinetics, relevant mineral formation, changes in mineral texture, and changes in mineral volume. As more $Fe^{2+}$ (and, less commonly $Fe^0$) is oxidized, the rate of the reaction will slow, resulting in a decline curve of new hydrogen generation that occurred at each time step. This decline curve can be used to calculate the rate of hydrogen generation as well as the remaining hydrogen generating potential ($H2_{RPV}$).

An embodiment relates to the evaluation of minerals relevant to hydrogen generation present prior to and after the reaction. The thermodynamic stability of given $H_1$ minerals within the experimental conditions can be evaluated by comparing changes in pre- and post-experimental mineralogical compositions. Dissolution of $H_1$ minerals will occur if the mineral is unstable at the experimental conditions (e.g., based on water volume or chemistry), which can then result in a reaction yielding $H_2$ minerals and hydrogen gas. In comparison, conditions where the $H_1$ minerals are stable will not result in mineral dissolution, therefore indicating the experimental conditions are not suitable for hydrogen generation.

An embodiment relates to determining the reaction kinetics through evaluations of the mineralogic composition prior to, and after the reaction. The kinetics of the reaction can be determined by evaluating mineralogic composition through a series of identical experiments, each of which was terminated after progressively longer durations (e.g., biweekly). Each progressive time step will contain a lesser amount of $H_1$ minerals as they are converted to either $H_{2a}$ or $H_{2b}$ phases through hydrogen generating reactions (e.g., serpentinization). The rate of the conversion will therefore slow after each time step and pairing this information with the reactive surface area and mineralogical analysis can yield the kinetic rate of hydrogen generating reaction of a given hydrogen source rock.

An embodiment relates to determining the reaction kinetics through evaluations of the gas composition prior to and after the reaction. The kinetics of the reaction can be determined by evaluating the gas composition through a series of identical experiments, each of which was terminated after progressively longer durations (e.g., biweekly). Each progressive time step will contain a higher concentration of hydrogen as it is generated during reactions that convert $H_1$ minerals to either $H_{2a}$ or $H_{2b}$ phases through hydrogen generating reactions (e.g., serpentinization). Overtime, however, the $H_1$ minerals will deplete, and the rate of the conversion will slow, which is observable in the gas composition data. This gas composition data can yield the kinetic rate of hydrogen generating reaction of a given hydrogen source rock.

An embodiment of the present disclosure relates to comparing the changes in pre- and post-experimental mineralogical compositions, which can be used to evaluate the reaction efficiency of converting $H_1$ minerals to relevant minerals that have generated hydrogen ($H_{2a}$ and $H_{2b}$) rather than minerals that have not.

An embodiment of the present disclosure relates to comparing the changes in pre- and post-experimental mineral texture, which can provide estimates of the completion of the reaction. For example, the proportion of hydrogen source rock possessing a fibrous mineral texture may be indicative of hydrogen generating reactions, such as serpentinization.

An embodiment of the present disclosure relates to comparing the changes in pre- and post-experimental mineral size to evaluate reaction completion and newly formed porosity. Specifically, serpentinization reactions that lead to hydrogen generation can cause hydrogen source rocks to expand, creating new fractures (potentially unaltered) and hence surface area that can further the completion of the reaction and increase the effective porosity and permeability of the formation.

An embodiment of the present disclosure relates to comparing the changes in pre- and post-experimental valence state of iron ($Fe^{2+}/Fe^{3+}$) in individual minerals. This can be used to evaluate reaction efficiency and extent of reaction completion.

An embodiment of the present disclosure relates to comparing the changes in pre- and post-experimental fluid chemistry. This can be used to evaluate how hydrogen generating reactions change fluid chemistry, which can be incorporated into exploration strategies.

Figure 15:
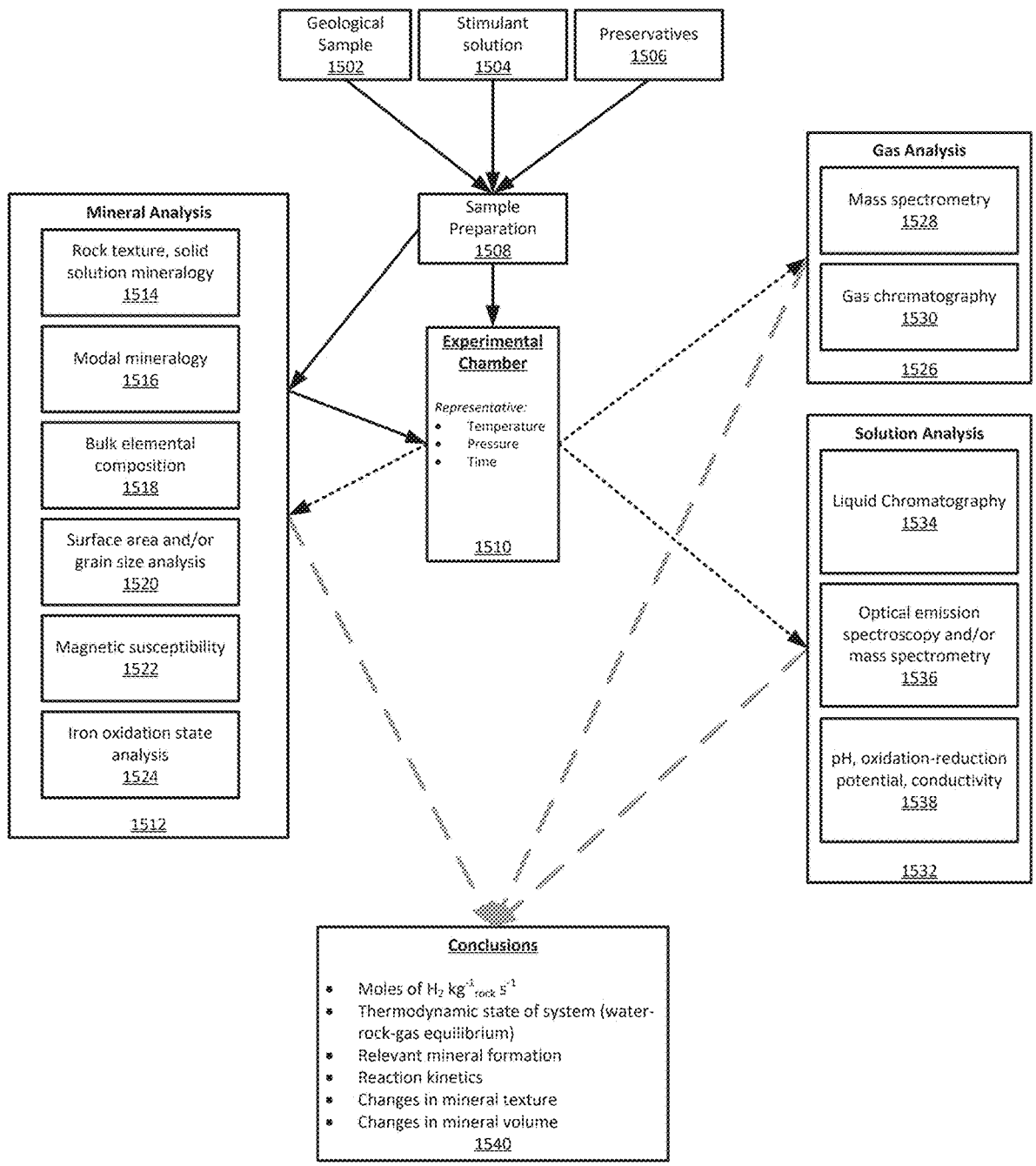
FIG. 15 is an example flow chart of a method for using the disclosed system to analyze changes in the pre- and post-experimental materials contained within the reaction chamber. Examples include changes in gas composition and sample pressures (related to changing volumes of gas released from the sample over time), mineralogic composition and textures, and aqueous chemistry parameters.

As shown in FIG. 15, the techniques above are combined to leverage data with increasing specificity with regards to evaluating hydrogen source rocks by defining the mineralogy through mineral analysis 1512, which may comprise rock texture and solid solution mineralogy 1514, modal mineralogy 1516, bulk elemental composition 1518, surface area and/or grain size analysis 1520, magnetic susceptibility 1522, or iron oxidation state analysis 1524, before and/or after geological sample materials have been subjected to experimental conditions (e.g., within experimental chamber 1510). As described above, a geological sample 1502 may undergo some forms of sample preparation 1508 such as comminuting, crushing, cutting, or other processes. Sample preparation 1508 may also comprise mixing the geological sample 1502 with a stimulant solution 1504 and mixture of preservatives 1506, as described herein. Following sample preparation 1508, samples may either proceed directly to mineral analysis 1512 and then be placed in experimental chamber 1510, or they may proceed directly to the experimental chamber 1510. In some embodiments, as described in the foregoing sections, the experimental chamber 1510 may be subjected to a variety of stimulation times, temperatures, and pressures, representative of potential past, present, future, or engineered subsurface conditions.

Following the stimulation process performed in the experimental chamber 1510, the contents of the experimental chamber 1510 may be analyzed by mineral analysis 1512, gas analysis 1526, and solution analysis 1532. Gas analysis 1526 may comprise mass spectrometry 1528 and/or gas chromatography 1530. Solution analysis 1532 may comprise liquid chromatography 1534, optical emission spectroscopy and/or mass spectrometry 1536, or assessing the solution's pH, oxidation-reduction potential, and/or conductivity 1538. Using the data sets collected from mineral analysis 1512, gas analysis 1526, and solution analysis 1532, the following conclusions 1540 can be made about the geological sample 1502 and the geological source rock corresponding to the geological sample 1502:

Moles of $H_2$ $kg^{-1}_{rock}$ $s^{-1}$

Thermodynamic state of system (water-rock-gas equilibrium)

Relevant mineral formation

Reaction kinetics

Changes in mineral texture

Changes in mineral volume

Figure 16:
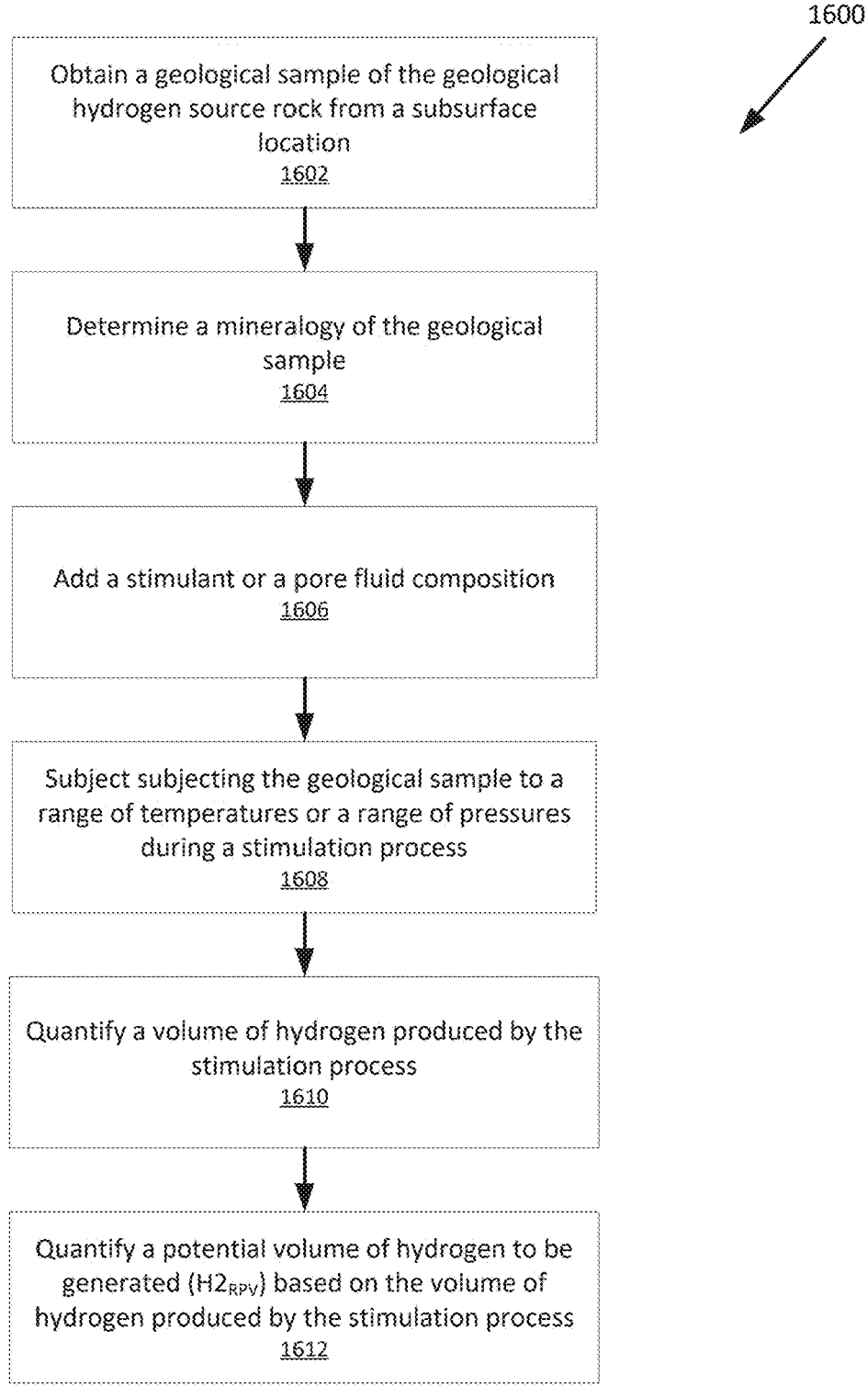
FIG. 16 shows an example flowchart for quantifying $H2_{RPV}$ of a geological sample, in accordance with some example embodiments described herein.

Turning to FIG. 16, procedure 1600 illustrates example embodiments for evaluating a geological source rock to quantify a potential volume of hydrogen ($H2_{RPV}$) to be generated. As described herein, the methods for determining $H2_{RPV}$ are useful for determining the value of a source rock for EHP and related hydrogen exploration processes. These methods are imperative for determining the quality of the source rock and its potential for future hydrogen generation and may provide additional clues as to the ability of a source rock to serve as a location to sequester carbon and/or sulfur through mineralization processes. In some embodiments, the entire method depicted in FIG. 16 may be repeated multiple times on one or more geological samples to determine optimal conditions for hydrogen generation, such as optimal stimulation times, temperatures, pressures, and stimulant fluid parameters, and others. Additionally, some embodiments may comprise subjecting the geological sample to the historic temperature and pressure conditions is used to quantify a rate of hydrogen generation and a volume of hydrogen generated during a specific geologic period of time. In some embodiments, the optimal stimulant fluid composition may first be estimated by data collected during drilling, a formation test, a flow test, or a production test at the time of collecting the geological sample.

As shown in operation 1602, a geological sample of the geological source rock is obtained. In some embodiments, the geological sample obtained could be obtained from a drilling site in the form of core samples, rock cuttings, or other standard sample varieties known in the art.

As shown in operation 1604 a mineralogy of the geological sample is determined. In some embodiments, samples may be used as-is for experimentation or may be processed in some way, such as by crushing, comminuting, and/or powdering. In some embodiments, mineral phases of the geological sample may be separated from one another before or after analysis. In some embodiments, samples may be subjected to one or more forms of analysis before and/or after the samples are processed or subjected to one or more additional analyses. In some embodiments, analyses of the geological sample may comprise powder diffraction techniques, elemental analysis techniques, colorimetric or optical techniques, spectroscopic techniques, surface area determination techniques, mineral dissolution techniques, modal mineralogy techniques, normative mineralogy techniques, or other mineralogy determination methods known in the art. In some embodiments, the mineralogy of a sample may be determined modally or normatively. In some embodiments, minerals may be further classified as belonging to $H_0$, $H_1$, or $H_2$. In some embodiments, minerals in class $H_2$ may be further classified into sub-classes $H_{2a}$ and $H_{2b}$.

As shown in operation 1606, a stimulant or a pore fluid composition is added to the geological sample. In some embodiments, the stimulant solution or pore fluid composition may be added directly to the geological sample in a reaction chamber or other suitable container for the method depicted in FIG. 16. In some embodiments, the stimulant solution or pore fluid composition may comprise a synthetic idealized fluid which may further comprise a fluid mixture with particular pH, Eh, ionic strength, ion concentration, minor and trace element concentration, gas concentration, organic constituent concentration, or other factors. In some embodiments, the oxygen fugacity content may be reduced to negligible levels (i.e., 0.01 mmol/L $O_2$(aq)). In some embodiments, the stimulant or pore fluid composition may include conditions matched to the in situ temperature, pressure, or formation fluid chemistry conditions of the geologic province in which the hydrogen source rock exists. Some embodiments may use synthetic formation fluid chemistries representative of the conditions that hydrogen source rock had been subjected to at some time in the geologic past.

As shown in operation 1608, the geological sample is subjected to a range of temperatures or a range of pressures during a stimulation process. In some embodiment, the selected range of temperatures may be between 20° C. and 500° C. In some embodiments, the range of pressures may be between 15 and 15,000 psi. In some embodiments, the stimulation process may be performed for set periods of time including minutes, hours, or days. Some embodiments may use present temperature or pressure conditions (e.g., by using depth data, bottom hole temperature data, or geothermal gradient data) of a geological source rock. In some embodiments, temperatures and pressures may remain the same or change over the course of a stimulation process.

As shown in operation 1610, a volume of hydrogen produced by the stimulation process is quantified. In some embodiments, at the conclusion of the stimulation process or at any point during the stimulation process, an aliquot of fluids may be removed from the reaction chamber. In some embodiments, the chamber is attached to a vacuum line, and a small aliquot of gas is expanded into a static vacuum line. In some embodiments, selectively removing constituent gases may comprise subjecting the bulk gas to cryogenic temperatures, flowing the bulk gas through a membrane, chromatographic separation, or other gas separation methods known in the art. In some embodiments, evaluating the 'mobile' gases may comprise the use of a mass spectrometer to determine concentrations, elemental identities, isotopic identities, isotopologues, partial pressures, or other qualities of the constituent components of a mixture of gases. In some embodiments, evaluating the 'mobile' gases may comprise processing the data from mass spectrometry measurements to remove contributions from interferences, contaminations, or atmospheric components, such that the composition of the analyte gases is known, including the partial pressures of each constituent gas in the mixture of analyte gases. In some embodiments, the partial pressure of hydrogen may be used to determine an amount of hydrogen which was generated by the stimulation process.

As shown in operation 1612, a potential volume of hydrogen to be generated ($H2_{RPV}$) is quantified based on the volume of hydrogen produced by the stimulation process. In some embodiments, the amount of hydrogen generated by the geological sample as a result of the stimulation process may be used to calculate the amount of hydrogen which may be produced ($H2_{RPV}$) by a geological source rock corresponding to the geological sample. In some embodiments, data from multiple geological samples or multiple stimulation processes may be used to determine the $H2_{RPV}$ of a given geological source rock corresponding to one or more geological samples. In some embodiments, quantifying the $H2_{RPV}$ may comprise multiplying the potential volume of generated hydrogen times a thickness of the geological source rock, an aerial extent of the geological source rock, and an average density of the geological source rock.

Applications of Combined Hydrogen Generation Evaluation Processes

The methods and systems described above can be used in conjunction to evaluate source rock or other components of the hydrogen system. The method(s) and other analyses employed to evaluate a given sample will depend on the source of geologic material (e.g., drill cuttings from active wells, drill cuttings from historic wells, outcrop, subcrop, sediment). Analyzing the 'mobile' gas phase requires recently extracted sampling material and has limited applicability when evaluating data that has been allowed to degas for extended periods of time (e.g., drill cuttings stored in a repository for decades). 'Immobile' gas analysis methods can be run on a wider assortment of samples that include drill cuttings collected immediately after drilling and also other materials collected more than several decades earlier that can be crushed and analyzed.

Given their rapid analysis times and ability to be conducted in the field (e.g., using portable instrumentation, analysis in a laboratory trailer), both the vacuum extraction and crushing extraction methods can be run for samples collected while drilling, allowing for real time drilling decisions to take place (i.e., making decisions to stop drilling, making decisions to continue drilling, evaluation of hydrogen mud gas shows, defining target intervals for drill stem tests or other analyses).

Methods to measure remaining hydrogen generating potential ($H2_{RPV}$) can be conducted on both recently extracted and archived geologic material collected from historic wells and should be completed in conjunction with the vacuum extraction and/or crushing extraction methods.

In addition to conducting the analyses required to obtain $H2_{EV}$ and $H2_{RPV}$, the same geologic material should also be analyzed for mineralogy to determine its relative abundance of $H_0$, $H_1$, and $H_2$ minerals, which is incorporated into normative and modal models to yield $M_1$ and $M_2$. Each of these values is critical to properly evaluate the feasibility of a specific lithologic unit to serve as a target hydrogen source rock within the broader hydrogen system, and the applications of these values is discussed in greater detail below.

Figure 17:
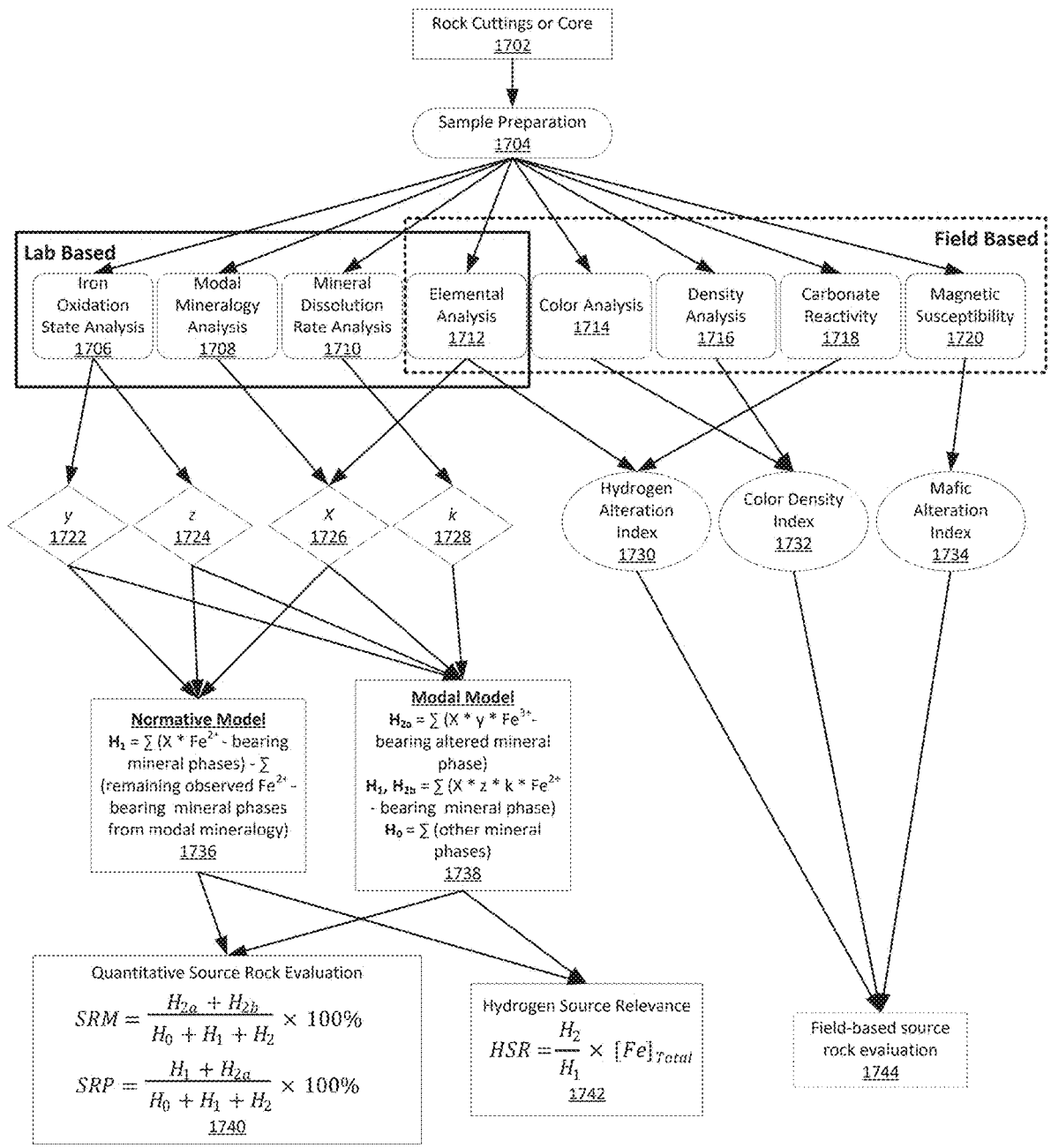
FIG. 17 is a workflow describing the process measuring the elemental composition of a rock, determining the normative mineralogy of the sample, assessing iron content of the minerals, and measuring the $H_1$ and $H_2$ mineral assemblages to assess past and future hydrogen generation potential.

As shown in FIG. 17, the techniques above are combined to leverage data with increasing specificity with regards to evaluating hydrogen source rocks by defining $H_0$, $H_1$, and $H_2$ composition in accordance with the availability of increasingly complete datasets. After sample preparation 1704, field-based assessments 1706-1720 may be performed on samples (e.g., rock cuttings or core 1702) without physical alteration of the samples. These field-based assessments may comprise elemental analysis 1712, color analysis 1714, density analysis 1716, carbonate reactivity 1718, and/or magnetic susceptibility 1720. The data resulting from these analyses can be used to estimate various indices of the rock cuttings or core samples 1702, such as the hydrogen alteration index 1730, color-density index 1732, or mafic alteration index 1734 as described herein. All of these data may be used to form a field-based source rock evaluation 1744 which may be used to grade source rocks or estimate the potential of a rock formation as a source of hydrogen.

Laboratory based methods may require physical alteration of the samples. As described above, laboratory-based assessments may comprise iron oxidation state analysis 1706 (e.g., Mossbauer spectroscopy), modal mineralogy analysis 1708 (e.g., powder diffraction), mineral dissolution rate analysis 1710 (e.g., ICP-OES), or elemental analysis 1712 (e.g., SEM/EDS). From these analyses, several variables may be determined comprising the $Fe^{3+}/Fe_{TOT}$ of the iron endmember of solid solution, y 1722, the $Fe^{2+}/Fe_{TOT}$ of the iron endmember of solid solution, z 1724, the fraction of iron endmember of the solid solution, X 1726, and the dissolution rate of the hydrogen generating mineral phase, k 1728. These variables and other data may then be incorporated into normative model 1736, in order to determine $H_1$, and/or modal model 1738, in order to determine $H_0$, $H_1$, $H_{2a}$, and $H_{2b}$. Following the establishment of normative model 1736 and modal model 1738, quantitative source rock evaluation 1740 may be performed in order to calculate the source rock maturity (SRM) and the source rock potential (SRP). Additionally, these models can be used to calculate hydrogen source relevance 1742.

Source Rocks in Context of the Hydrogen System

The aforementioned discussion describes systems and methods that can be applied separately or in combination to evaluate the quality and purpose of hydrogen source rocks and allow for quantitative scoring of prospective formations or regions. By considering the mineralogy of a source rock (i.e., relative abundances of $H_0$, $H_1$, and $H_2$ minerals), theoretical estimates of the potential hydrogen generation ($M_1$) and completed hydrogen generation ($M_2$) can be compared to the corresponding measurements of existing volumes of hydrogen ($H2_{EV}$) and remaining potential volumes of hydrogen ($H2_{RPV}$) for a given sample that are measured by the analytical methods disclosed herein. When calculated on a per unit mass or per volume basis, the $H2_{EV}$ and $M_2$ values can be considered as metrics of the hydrogen source rock maturity and used to quantitatively score the suitability of the rock to serve as a source rock in a conventional or unconventional hydrogen system. Likewise, the $H2_{RPV}$ and $M_1$ values can be considered as metrics of the hydrogen source rock potential and provide a quantitative score of the suitability of the rock to serve as a source rock for future hydrogen generation under the appropriate geochemical conditions.

In an embodiment, if the mineralogy of a source rock has been determined to be relevant for hydrogen generation (high abundance of $H_1$, $H_{2a}$, and/or $H_{2b}$ minerals), the ratio of its $H2_{EV}$ to $H2_{RPV}$ can be used to assess hydrogen source rock maturity ($H2_{maturity}$):

$$H2_{maturity} = \frac{H2_{EV}}{H2_{RPV}} \times 100\%$$

The higher the value of $H2_{maturity}$, the more the source rock is better suited to conventional or unconventional hydrogen exploration if gases were accumulated or remain in place, where much of the source rock has been altered and generated hydrogen that either accumulates within the source formation itself (unconventional) or migrates and accumulates in an overlying reservoir (conventional). A $H2_{maturity}$ value closer to 0% would instead indicate that the source rock requires different pressure, temperature, and chemistry conditions than those of its past or current geologic settings to generate hydrogen. While it may have limited relevance to conventional/unconventional hydrogen exploration, the source rock may be an ideal stimulation target (e.g., for EHP). Importantly, source rock that is analyzed and determined to be immature (low $H2_{maturity}$ value) may not require engineered stimulation to generate hydrogen but instead production may be possible by exploiting the same source rock elsewhere in the geologic province where it is/was located at a differing depth and exposed to relevant hydrogen generating conditions. Analysis from longitudinal experiments (i.e., a series of pressure and temperature increases) can determine what conditions are necessary for hydrogen generation which can also focus exploration efforts on identifying locations corresponding to these conditions.

Figure 18:
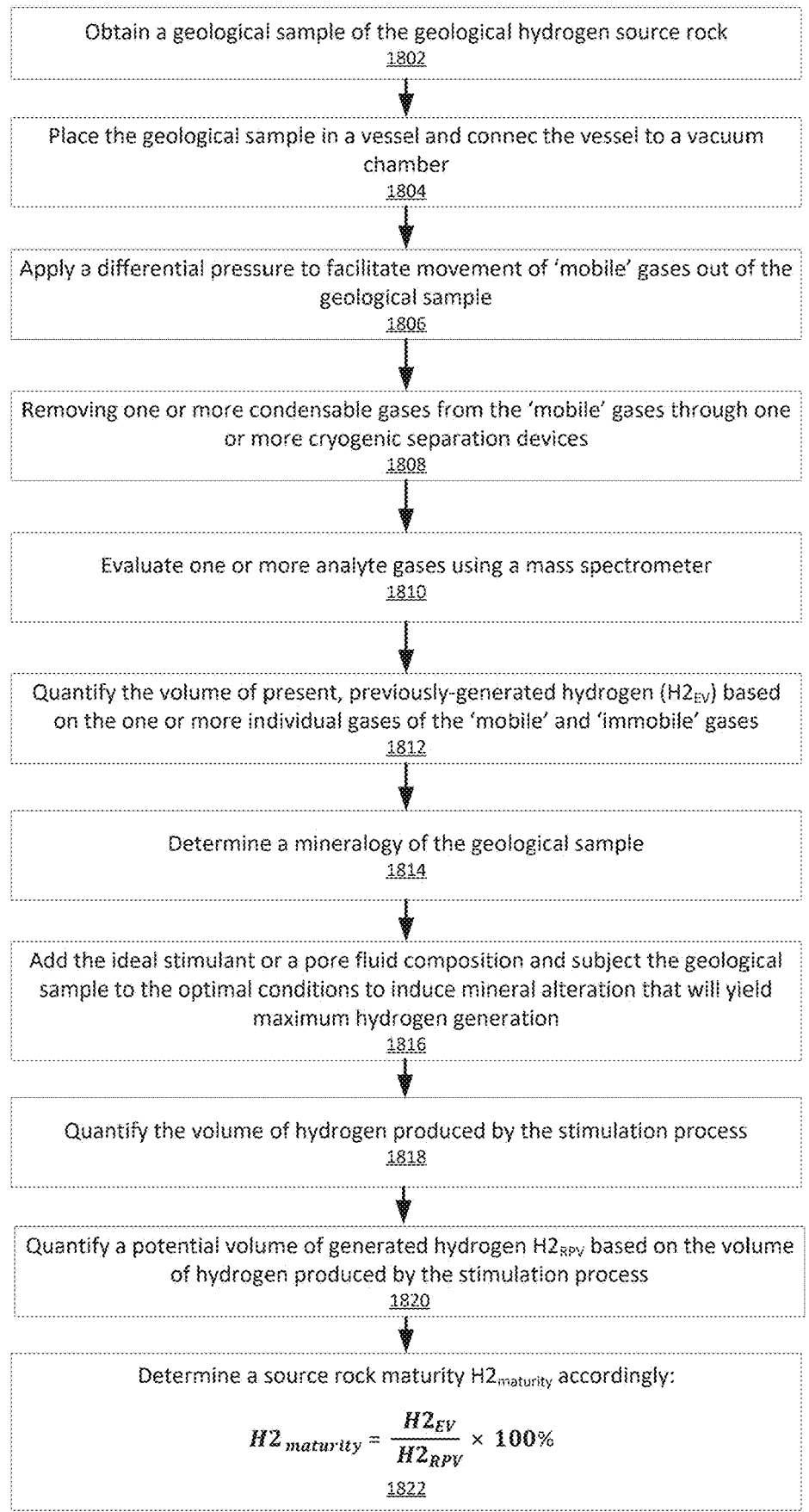
FIG. 18 shows an example flowchart for evaluating a hydrogen source rock, in accordance with some example embodiments described herein.

Turning now to FIG. 18, procedure 1800 illustrates example embodiments for quantifying hydrogen potential of a geological source rock based on the $H2_{EV}$ and $H2_{RPV}$ value of the geological source rock. The $H2_{EV}$, which is able to be determined independent of the geological source rock's mineralogy, serves as an indirect indicator of the past alteration of the geological source rock. The $H2_{RPV}$, as determined experimentally or otherwise, serves as an indicator of the potential future hydrogen producing capacity of the geological source rock. These two values, when taken together, may be used to determine the $H2_{maturity}$ of the geological source rock, using the methods disclosed herein.

As shown in operation 1802, a geological sample of the geological source rock is obtained. In some embodiments, the geological sample could be obtained from a drilling site in the form of core samples, rock cuttings, or other standard sample varieties known in the art. In some embodiments, the geological sample could be obtained from a repository of samples from known locations. In some embodiments, the geological sample could be obtained from or near the surface, such as from a rock outcrop or mining operation.

As shown in operation 1804, the geological sample is placed in a vessel and the vessel is connected to a vacuum chamber. In some embodiments, the vessel may be sealed with a septum or other pierceable seal. In some embodiments, the vessel may be a container which is inert, non-reactive with hydrogen, and/or compressible. In some embodiments, the vessel may be fluidly connected to the vacuum chamber through plumbing, by piercing the seal of the vessel with a needle connected to the vacuum chamber, or by any other standard means.

As shown in operation 1806, a differential pressure is applied to facilitate movement of 'mobile' gases out of the geological sample. In some example embodiments, a pressure gradient may be established by sealing the geological sample in an inert, compressible, container with a pierceable seal, which may additionally contain atmospheric gases, preservatives, or other components which are not part of the analyte gases (e.g., gases contained within or bound to a geological sample), fluidly connecting (e.g., plumbing) the container to an chamber held at a lower pressure that the pressure of gases in the container, and allowing gases from the container to flow into the chamber until an equilibrium pressure is reached between the container and the chamber such that the 'mobile' gases in the container, which were associated with the geological sample, are a part of the bulk gas in the chamber. In some embodiments, geological samples may be subject to extraction of their 'mobile' gases multiple times with or without alteration of the sample. Though not shown in this example, in some embodiments, 'immobile' gases (e.g., gases contained in sealed chambers of the geological sample) may then be mobilized by crushing, comminuting, powdering, or other standard methods known in the art, and then extracted from the geological sample. In some embodiments, the volume of gases extracted may be measured. In some embodiments, the container may be compressed (e.g., with a hydraulic press).

As shown in operation 1808, one or more condensable gases are removed from the 'mobile' gases through one or more cryogenic separation devices. In some embodiments, cryogenic separation may be accomplished using a cold finger device, a trap submerged in cryogenic fluids, or other devices known in the art. In some embodiments, the ammonia and water are separated by condensing and removed from the device at the completion of the method shown in FIG. 18.

As shown in operation 1810, one or more analyte gases are evaluated using a mass spectrometer. In some embodiments, gases may be flowed into a mass spectrometer without further separation. In some embodiments, gases may be further separated (e.g., chromatographically) prior to entering the mass spectrometer. In some embodiments, the mass spectrometer may be a quadrupole mass spectrometer. In some embodiments, the mass spectrometer may additionally include an ion trap. In some embodiments, data is collected from the mass spectrometer for determining the mass to charge ratio (m/z) of an atomic mass unit (AMU)

which can be further used to determine the species of the analyte gas, the species of the analyte gas comprising the elemental identity or isotopic identity of the analyte gas.

As shown in operation 1812, a volume of hydrogen previously generated ($H2_{EV}$) is quantified based on the 'mobile' gases. In some embodiments, the volume of hydrogen previously generated ($H2_{EV}$) may be calculated based on the volume of gases extracted from the geological sample and the partial pressure of each constituent gas in the mixture of analyte gases. In some embodiments, the volume of hydrogen previously generated ($H2_{EV}$) may be quantified after multiple rounds of operations 1802-1810 have been performed on a single geological sample.

As shown in operation 1814, a mineralogy of the geological sample is determined. In some embodiments, samples may be used as-is for experimentation or may be processed in some way, such as by crushing, comminuting, and/or powdering. In some embodiments, mineral phases of the geological sample may be separated from one another before or after analysis. In some embodiments, samples may be subjected to one or more forms of analysis before and/or after the samples are processed or subjected to one or more additional analyses. In some embodiments, analyses of the geological sample may comprise powder diffraction techniques, elemental analysis techniques, colorimetric or optical techniques, spectroscopic techniques, surface area determination techniques, mineral dissolution techniques, modal mineralogy techniques, normative mineralogy techniques, or other mineralogy determination methods known in the art. In some embodiments, the mineralogy of a sample may be determined modally or normatively. In some embodiments, minerals may be further classified as belonging to $H_0$, $H_1$, or $H_2$. In some embodiments, minerals in class $H_2$ may be further classified into sub-classes $H_{2a}$ and $H_{2b}$.

As shown in operation 1816, optimal conditions to induce mineral alteration to yield further potential hydrogen generation are determined. In some embodiments, the stimulant solution or pore fluid composition may be added directly to the geological sample in a reaction chamber or other suitable container for the method depicted in FIG. 18. In some embodiments, the stimulant solution or pore fluid composition may comprise a synthetic idealized fluid which may further comprise a fluid mixture with particular pH, Eh, ionic strength, ion concentration, minor and trace element concentration, gas concentration, organic constituent concentration, or other factors. In some embodiments, the oxygen fugacity content may be reduced to negligible levels (i.e., 0.01 mmol/L $O_{2(aq)}$). In some embodiments include subjecting the geological sample to a range of temperatures or a range of pressures during a stimulation process. In some embodiment, the selected range of temperatures may be between 20° C. and 500° C. In some embodiments, the range of pressures may be between 15 and 15,000 psi. In some embodiments, the stimulation process may be performed for set periods of time including minutes, hours, or days. Some embodiments may use present temperature or pressure conditions (e.g., by using depth data, bottom hole temperature data, or geothermal gradient data) of a geological source rock. In some embodiments, temperatures and pressures may remain the same or change over the course of a stimulation process. Some embodiments include quantifying a volume of hydrogen produced by the stimulation process. In some embodiments, at the conclusion of the stimulation process or at any point during the stimulation process, an aliquot of fluids may be removed from the reaction chamber. In some embodiments, the chamber is attached to a vacuum line, and a small aliquot of gas is expanded into a static vacuum line. In some embodiments, selectively removing constituent gases may comprise subjecting the bulk gas to cryogenic temperatures, flowing the bulk gas through a membrane, chromatographic separation, or other gas separation methods known in the art. In some embodiments, evaluating the mobile gases may comprise the use of a mass spectrometer to determine concentrations, elemental identities, isotopic identities, isotopologues, partial pressures, or other qualities of the constituent components of a mixture of gases. In some embodiments, evaluating the 'mobile' gases may comprise processing the data from mass spectrometry measurements to remove contributions from interferences, contaminations, or atmospheric components, such that the composition of the analyte gases is known, including the partial pressures of each constituent gas in the mixture of analyte gases. In some embodiments, the partial pressure of hydrogen may be used to determine an amount of hydrogen which was generated by the stimulation process. In some embodiments, the process of operation 1816 may be repeated on the same or similar geological sample until an optimal set of conditions is found when maximizes hydrogen generation.

As shown in operations 1818-1820, a potential volume of hydrogen to be generated ($H2_{RPV}$) based on the volume of hydrogen produced by the stimulation process is quantified. In some embodiments, the amount of hydrogen generated by the geological sample as a result of the stimulation process determined in step 1818 is used to calculate the amount of hydrogen which may be produced ($H2_{RPV}$) by a geological source rock corresponding to the geological sample in step 1820. In some embodiments, data from multiple geological samples or multiple stimulation processes may be used to determine the $H2_{RPV}$ of a given geological source rock corresponding to one or more geological samples. In some embodiments, quantifying the $H2_{RPV}$ may comprise multiplying the potential volume of generated hydrogen times a thickness of the geological source rock, an aerial extent of the geological source rock, and an average density of the geological source rock.

As shown in operation 1822, some embodiments include determining a source rock maturity $H2_{maturity}$ accordingly:

$$H2_{maturity} = \frac{H2_{EV}}{H2_{RPV}} \times 100\%.$$

In some embodiments, the $H2_{maturity}$ may indicate that a geological source rock is suitable for conventional or unconventional geologic hydrogen exploration. In some embodiments, the $H2_{maturity}$ may indicate that a geological source rock is suitable for EHP hydrogen exploration.

A source rock with high $H2_{maturity}$ can play significant roles in either conventional or unconventional hydrogen exploration depending on whether the source rock still contains volumes of previously generated hydrogen. Discrepancies between $H2_{EV}$ and $M_2$ may result from several processes described above (e.g., migration of hydrogen out of the system, biological or chemical degradation of hydrogen, accumulation of exogenous hydrogen within the source rock that was generated from other areas and/or depths of the geological province) and allow for further hydrogen source rock evaluation. The $H2_{EV}$ represents the portion of generated hydrogen that remains within the source rock and can be assessed with respect to the total theoretical hydrogen generation to calculate the amount of hydrogen retained by the source rock ($H2_{retained}$):

$$H2_{retained} = \frac{H2_{EV}}{M_2} \times 100\%$$

In some embodiments, $H2_{retained}$ may indicate possible hydrogen migration out of the hydrogen source rock and into conventional reservoirs, and/or biological or chemical degradation of hydrogen ($H2_{retained} \ll 100\%$). In some embodiments, $H2_{retained}$ may indicate the source rock has retained the hydrogen produced in-situ ($H2_{retained} \approx 100\%$). In some embodiments, $H^2_{retained}$ may indicate that the hydrogen source rock has accumulated and retained exogenously sourced hydrogen which was generated elsewhere in the geological province (e.g., at different depths than where the hydrogen source rock was sampled, and/or other areas in a basin, $H2_{retained} > 100\%$).

Source rocks with low $H2_{maturity}$ are unlikely to play a role in either conventional or unconventional hydrogen systems. Instead, these rocks may be able to generate hydrogen if exposed to the appropriate geophysical and geochemical conditions.

Discrepancies between $H2_{RPV}$ and $M_1$ are related to the loss of hydrogen from source rocks by mechanisms determined by workflows not disclosed herein. Alteration of $H_1$ and $H_{2a}$ minerals will never reach 100% completion and thus the calculated $M_1$ is likely to be greater than the measured $H2_{RPV}$. However, the closer the ratio of $H2_{RPV}$ to $M_1$ is to 1, the greater the hydrogen capacity of the source rock ($H2_{capacity}$):

$$H2_{capacity} = \frac{H2_{RPV}}{M_1} \times 100\%$$

Because $H2_{RPV}$ is calculated from experiments that subject the hydrogen source rock to the same in situ chemistry as its current geologic setting, a hydrogen source rock that has a $H2_{capacity}$ close to 100% implies that the rock is capable of hydrogen generation if subjected to higher pressure and/or temperature conditions. On the contrary, if the $H2_{capacity}$ is closer to 0%, the rock sample may not yield any future hydrogen generation in the present conditions; locations with more optimal conditions would need to be identified by other workflows.

The application of this analysis for subsurface carbon sequestration by carbon mineralization or sulfur sequestration by sulfur mineralization is also considered. Minerals associated with carbon or sulfur mineralization reactions (e.g., calcite, pyrite) would need to be categorized into their roles in the sequestration process and the potential for future mineralization would have to be established stoichiometrically. Once determined however, the ratios of mineralized carbon to mineralization potential and mineralized sulfur to mineralization potential can be used to score a source rock's suitability for carbon or sulfur sequestration as well as estimate the potential volumes of carbon or sulfur rich fluids that can be injected.

Figure 19:
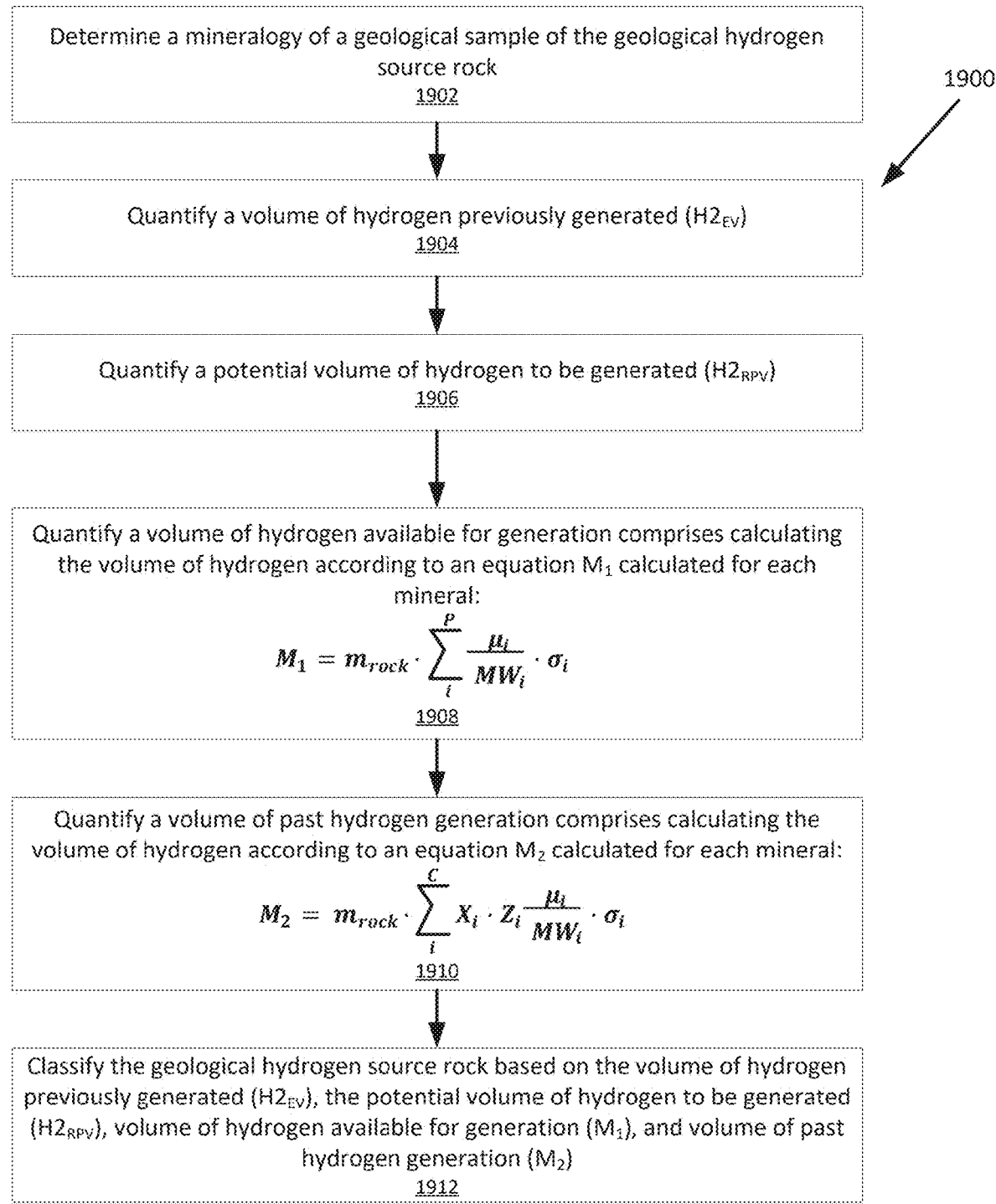
FIG. 19 shows an example flowchart for classifying a geological sample based on its hydrogen-generation characteristics, in accordance with some example embodiments described herein.

As shown in FIG. 19, procedure 1900 illustrates methods for classifying geological source rock based on the volume of hydrogen previously generated ($H2_{EV}$), the potential volume of hydrogen to be generated ($H2_{RPV}$), volume of hydrogen available for generation ($M_1$), and volume of past hydrogen generation ($M_2$) which have been determined for the geological source rock under investigation. The method begins by using the analytical methods described herein to determine the mineralogy of a geological sample of the geological source rock, as shown in operation 1902. Using the methods and apparatuses described above, the $H2_{EV}$ of the geological sample is determined in operation 1904 and the $H2_{RPV}$ is determined in operation 1906. Using the data collected in operation 1902, the volume of hydrogen available for generation is quantified in operation 1908 and comprises calculating the volume of hydrogen according to an equation $M_1$ calculated for each mineral according to the equation for $M_1$ provided above. Using the data collected in operation 1902, the volume of past hydrogen generation is quantified in operation 1910 and comprises calculating the volume of hydrogen according to an equation $M_2$ calculated for each mineral according to the equation for $M_2$ provided above. In operation 1912, the calculated $M_1$ and $M_2$ values, and the determined $H2_{EV}$ and $H2_{RPV}$ values are used to classify the geological source rock, as described above.

Regional Scale Evaluation of Source Rock

While these analyses and scores are established for individual samples of hydrogen source rock, the results can be extrapolated to other parts of a geologic province if data suggest there are similar characteristics throughout the geologic province or if reasonable inferences can be made about source rock quality and pressure and temperature conditions in other areas. As an example, a high-quality source rock identified through the embodiments described above could be extrapolated if the aeromagnetic and aerogravity signatures tied to a given well are observed throughout a contiguous region. This allows for the assessment of a larger scale hydrogen system based on the evaluation of a representative hydrogen source rock within a given geologic province (e.g., on the prospect, block, or basin scale). This requires several assumptions to be meaningful but provides an initial framework that can be applied to multiple regions to define an objective ranking system that ranks candidate hydrogen exploration targets. First, the rock sample analyzed must be assumed to be representative of the source rock for the entire region. Because the lithologies may exhibit varying amounts of heterogeneity, multiple samples can be analyzed to get averages and uncertainties that can better describe the lithologic distribution across the region. Second, the source formation is assumed to be contiguous with a constant thickness across the region. Finally, the density of the formation is assumed to be constant so that molar calculations can be determined based on rock volume.

If the geometry of the prospect is known, the potential volume of hydrogen generation for a prospect can be calculated as:

$$P_{potential} = H2_{RPV} \times h_{form} \times A_{form} \times \rho_{form}$$

where $H2_{RPV}$ is the moles of hydrogen that can be generated by altering the source rock (on a per mass basis), $h_{form}$ is the thickness of the formation, $A_{form}$ is the areal extent of the formation, and $\rho_{form}$ is the average density of the formation. When source rocks can be imaged using geophysical data and interpretations from a given region, $h_{form}$ and $A_{form}$ can be replaced by volumetric estimates $V_{form}$. Similarly, the existing volume of hydrogen in a prospect can be calculated as:

$$P_{existing} = H2_{EV} \times h_{form} \times A_{form} \times \rho_{form}$$

where $H2_{EV}$ is the moles of hydrogen that have already been generated from the source rock (on a per mass basis), $h_{form}$ is the thickness of the formation, $A_{form}$ is the areal extent of the formation, and $\rho_{form}$ is the average density of the formation. When source rocks can be imaged using geophysical data and interpretations from a given region, $h_{form}$ and $A_{form}$ can be replaced by volumetric estimates $V_{form}$.

These two estimates are akin to estimating total volumes of gas generated for a particular region and can be improved by incorporating uncertainty in various components (e.g., geometry, mineralogy) and depth-depending characteristics (e.g., temperature, pressure, expansion factors) to yield initial estimates for the potential gas-in-place for various aspects of the natural hydrogen system. If applied uniformly, the actual values from different prospects can be compared and therefore the prospects can be ranked based on their volumetric hydrogen and/or potential for future generation via stimulation. Additionally, the relative proportions of $P_{potential}$ and $P_{existing}$ can categorize the hydrogen exploration method (natural hydrogen exploration in conventional or unconventional reservoirs as compared to EHP). These outputs can also be divided by area to provide an estimate of hydrogen on a per acre basis to improve economic valuation of the prospect.

Low Carbon Intensity Hydrogen

There is a significant focus today on the decarbonization of energy and chemical industries to positively impact climate change. In response, companies and individuals are actively working to produce cost-effective "clean" or "green" hydrogen and other chemicals. Hydrogen is labelled as "green" when its production results in significantly lower greenhouse gas emissions compared to the production of other energy sources. Governments have recently begun to categorize hydrogen by assessing the emissions intensity of the production plant or system from which the hydrogen is sourced. Specifically, components or portions of the hydrogen gas production process, including the hydrogen feedstock from a wellhead as well as the hydrogen gas product, can be assigned a carbon intensity (CI) score according to the greenhouse gas emissions resulting from the particular component or portion. The CI scores referenced herein are provided in kg $CO_2$ equivalent greenhouse gases per kg $H_2$ produced (kg $CO_2$eq/kg $H_2$).

In some embodiments, the methods and systems described herein are used to quantify hydrogen produced, or generated and subsequently produced within a drilled well or borehole and collected as feedstock. Feedstock extracted from boreholes into the subsurface from wellheads may be of a sufficient composition that it can be subsequently separated and/or purified to between about 90% and about 99.9999% purity, meeting the needs of the hydrogen markets.

In some examples, the feedstock includes primarily hydrogen gas. The feedstock may also include additional gas constituents such as nitrogen, carbon dioxide, methane and noble gases such as helium, neon, argon, krypton, xenon, or radon. In some examples, the feedstock has a CI score of less than 4.0 kg $CO_2$eq/kg $H_2$, or less than 3.0 kg $CO_2$eq/kg $H_2$, or less than 1.5 kg $CO_2$eq/kg $H_2$, or less than 0.45 kg $CO_2$eq/kg $H_2$. For example, a feedstock that includes at least 50 mol %, 60 mol %, 70 mol %, 75 mol %, 80 mol %, 85 mol %, 90 mol %, 95 mol %, 98 mol %, or 99% mol % hydrogen, less than 15 mol %, 12.5 mol %, 10 mol %, 9 mol %, 8 mol %, 7 mol %, 6 mol %, 5 mol %, 4 mol %, 3 mol %, 2 mol %, 1 mol %, 0.5 mol %, or 0.1% mol % carbon dioxide, less than 12.5 mol %, 10 mol %, 9 mol %, 8 mol %, 7 mol %, 6 mol %, 5 mol %, 4 mol %, 3 mol %, 2 mol %, 1 mol %, 0.5 mol %, 0.1 mol % methane ($CH_4$), and up to 50 mol %, 45 mol %, 40 mol %, 35 mol %, 30 mol %, 25 mol %, 20 mol %, 15 mol %, 12.5 mol %, 10 mol %, 9 mol %, 8 mol %, 7 mol %, 6 mol %, 5 mol %, 4 mol %, 3 mol %, 2 mol %, or 1 mol % nitrogen provides a CI score of less than 4.0, 3.0, 1.5, or 0.45 kg $CO_2$eq/kg $H_2$. In such cases, the hydrogen produced or obtained from these geological sources may be classified as low carbon intensity hydrogen.

Conclusions

It is noted that there is no requirement to provide or address the theory underlying the novel and groundbreaking systems, methods, performance or other beneficial features and properties that are the subject of, or associated with, embodiments of the present disclosure. Nevertheless, various theories are provided in this specification to further advance the art in this critical area, and in particular the important area of hydrogen, dihydrogen sulfide, carbon dioxide, and helium exploration, production and downstream conversion or utilization. These theories put forth in this specification, and unless expressly stated otherwise, in no way limit, restrict or narrow the scope of protection to be afforded the claimed embodiments. It is further understood that the present disclosure may lead to new, and heretofore unknown theories to explain the conductivities, drainages, resource production, chemistries, and function-features of embodiments of the methods, articles, materials, devices, and system of the present disclosure and that such later developed theories shall not limit the scope of protection afforded the present disclosure. Other embodiments than those specifically disclosed herein may be included without departing from its spirit or essential characteristics.

Further, the various embodiments of devices, systems, activities, methods, and operations set forth in this specification may be used with each other in different and various combinations. Thus, the configurations provided in the various embodiments of this specification may be used with each other. For example, the components of an embodiment having A, A', and B and the components of an embodiment having A", C, and D can be used with each other in various combinations (e.g., A, C, D, and A; A", C, and D; etc.) in accordance with the teaching of this specification. Thus, the scope of protection afforded by the present inventions should not be limited to a particular embodiment, configuration or arrangement that is set forth in a particular embodiment, example, or in an embodiment in a particular figure.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of classifying geological source rock, the method comprising:
   obtaining a geological sample of the geological source rock;
   placing the geological sample in a vessel and connecting the vessel to a vacuum chamber;
   applying a differential pressure to facilitate movement of 'mobile' gases out of the geological sample;
   directing a first gas stream of the 'mobile' gases through a first cryogenic device, wherein at least water is removed from the first gas stream of the 'mobile' gases by the first cryogenic device;
   directing a second gas stream of the 'mobile' gases through a second cryogenic device, wherein at least nitrogen is removed from the second gas stream of the 'mobile' gases by the second cryogenic device;
   evaluating the first gas stream and the second gas stream using a mass spectrometer;
   reconciling data from the mass spectrometer of the first gas stream and data from the mass spectrometer of the second gas stream to determine a bulk gas composition;
   quantifying a volume of hydrogen previously generated ($H2_{EV}$) based on the bulk gas composition;
   determining a mineralogy of the geological sample of the geological source rock, wherein the mineralogy includes one or more of the following:
      primary minerals $H_1$ involved in hydrogen generation; and
      secondary minerals $H_2$ that previously generated hydrogen, wherein the secondary minerals $H_2$ include a subset $H_{2a}$ of minerals capable of generating further hydrogen and a subset $H_{2b}$ of minerals incapable of generating hydrogen; and
   quantifying a volume of past hydrogen generation comprises calculating the volume of hydrogen according to an equation wherein $M_2$ is calculated for each mineral in a set of minerals i–C:

$$M_2 = m_{rock} \cdot \sum_i^C X_i \cdot Z_i \frac{\mu_i}{MW_i} \cdot \sigma_i$$

wherein $m_{rock}$ is a mass of sample being analyzed, $\mu_i$ is a relative abundance of mineral i in the sample, $X_i$ is an iron concentration of each mineral i, $Z_i$ is a ratio of $Fe^{3+}/Fe_{total}$ of iron in mineral i, $MW_i$ is a molecular weight of mineral i in kg/mol, and $\sigma_i$ is a stoichiometric ratio of moles of hydrogen generated from moles of mineral i, and wherein the equation $M_2$ is calculated for each $H_{2a}$ and $H_{2b}$ mineral of the geological sample; and
   classifying the geological source rock based on the volume of hydrogen previously generated ($H2_{EV}$) and volume of past hydrogen generation ($M_2$).

2. The method of claim 1, further comprising:
   adding a stimulant or a pore fluid composition to the geological sample;
   subjecting the geological sample to a range of temperatures or a range of pressures during a stimulation process;
   quantifying a volume of hydrogen produced by the stimulation process;
   quantifying a potential volume of hydrogen that may be generated ($H2_{RPV}$) based on the volume of hydrogen produced by the stimulation process;
   quantifying a volume of hydrogen available for generation comprises calculating the volume of hydrogen according to an equation wherein $M_1$ is calculated each mineral in a set of minerals i–P:

$$M_1 = m_{rock} \cdot \sum_i^P \frac{\mu_i}{MW_i} \cdot \sigma_i$$

where $m_{rock}$ is the mass of sample being analyzed, $\mu_i$ is the relative abundance of mineral i in the sample, $MW_i$ is the molecular weight of mineral i in kg/mol, and $\sigma_i$ is the stoichiometric ratio of moles of hydrogen generated from moles of mineral i, and wherein the equation $M_1$ is calculated for each $H_1$ and $H_{2a}$ minerals of the geological sample; and
   classifying the geological source rock based on the volume of hydrogen previously generated ($H2_{EV}$), the potential volume of hydrogen that may be generated ($H2_{RPV}$), volume of hydrogen available for generation ($M_1$), and volume of past hydrogen generation ($M_2$).

3. The method of claim 2, wherein classifying the geological source rock comprises classifying the geological source rock as an unaltered source rock suitable for enhanced hydrogen production (EHP), carbon mineralization, or sulfur mineralization.

4. The method of claim 2, wherein the mineralogy includes one or more minerals $H_0$ unrelated to hydrogen generation.

5. The method of claim 4, wherein the geological source rock is classified as a non-source rock for hydrogen when the mineralogy is dominantly $H_0$, the $H2_{EV}$ is low, and the $H2_{RPV}$ is low.

6. The method of claim 2, wherein the geological source rock is classified as an unconventional source rock-reservoir when the mineralogy is predominantly $H_{2a}$ and $H_{2b}$, the $H2_{EV}$ is high, and the $H2_{RPV}$ is low.

7. The method of claim 2, wherein the geological source rock is classified as an accumulation in unconventional source rock-reservoir when the mineralogy is dominantly $H_1$ or dominantly $H_{2a}$ and $H_{2b}$, and the $H2_{EV}$ is high.

8. The method of claim 2, wherein the geological source rock is classified as a source rock for conventional accumulation when the mineralogy is dominantly $H_{2a}$ and $H_{2b}$, the $H2_{EV}$ is low, and the $H2_{RPV}$ is low.

9. The method of claim 2, wherein the geological source rock is classified as an unaltered source rock for EHP or mineralization when the mineralogy is dominantly $H_1$, the $H2_{EV}$ is low, and the $H2_{RPV}$ is high.

10. The method of claim 2, wherein classifying the geological source rock comprises classifying the geological source rock as a non-source rock for hydrogen when the $M_1$ and $M_2$ are zero.

11. The method of claim 2, wherein determining the mineralogy comprises determining if the geological sample includes an abundant volume of hydrogen previously generated ($H2_{EV}$) with limited potential volume of hydrogen that may be generated ($H2_{RPV}$).

12. The method of claim 1, wherein classifying the geological source rock comprises classifying the geological source rock as hydrogen accumulation within the geological source rock when the volume of hydrogen previously generated ($H2_{EV}$) is greater than the volume of past hydrogen generation ($M_2$).

13. The method of claim 1, wherein classifying the geological source rock comprises classifying the geological source rock as an unconventional source rock-reservoir within the geological source rock when the volume of hydrogen previously generated ($H2_{EV}$) is about equivalent to the volume of past hydrogen generation ($M_2$).

14. The method of claim 1, wherein the volume of hydrogen previously generated ($H2_{EV}$) is less than the volume of past hydrogen generation ($M_2$).

15. The method of claim 14, wherein classifying the geological source rock comprises classifying the geological source rock as a source rock for conventional accumulations.

16. The method of claim 1, further comprising determining if the geological sample includes abundant altered minerals and no hydrogen gas.

17. The method of claim 16, wherein a determination of abundant altered minerals and no hydrogen gas indicates that hydrogen gas has migrated to other lithologic formations or has been consumed through subsurface chemical or biological processes.

18. The method of claim 16, wherein classifying the geological source rock comprises classifying the geological source rock as a source rock for a conventional hydrogen system with prospective accumulation in porous reservoirs.

19. The method of claim 1, further comprising evaluating the mineralogy.

20. The method of claim 19, wherein evaluating the mineralogy comprises determining whether the geological sample includes abundant primary minerals and no hydrogen gas.

* * * * *